(12) United States Patent
Jolly et al.

(10) Patent No.: US 11,060,112 B2
(45) Date of Patent: *Jul. 13, 2021

(54) PRODUCER CELLS FOR REPLICATION COMPETENT RETROVIRAL VECTORS

(71) Applicant: DENOVO BIOPHARMA LLC, San Diego, CA (US)

(72) Inventors: Douglas J. Jolly, Encinitas, CA (US); Carlos Ibanez, San Diego, CA (US)

(73) Assignee: DENOVO BIOPHARMA LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/431,626

(22) Filed: Jun. 4, 2019

(65) Prior Publication Data

US 2019/0352667 A1    Nov. 21, 2019

Related U.S. Application Data

(63) Continuation of application No. 13/376,827, filed as application No. PCT/US2010/038996 on Jun. 17, 2010, now Pat. No. 10,316,333.

(60) Provisional application No. 61/218,063, filed on Jun. 17, 2009.

(51) Int. Cl.
    *C12N 15/86*   (2006.01)
    *C12N 15/867*  (2006.01)

(52) U.S. Cl.
    CPC .... *C12N 15/86* (2013.01); *C12N 2740/13043* (2013.01); *C12N 2740/13051* (2013.01); *C12N 2740/13052* (2013.01)

(58) Field of Classification Search
    None
    See application file for complete search history.

(56) References Cited

U.S. PATENT DOCUMENTS

| | | |
|---|---|---|
| 5,324,645 A | 6/1994 | Takahara et al. |
| 6,410,313 B1 | 6/2002 | Kasahara et al. |
| 6,410,316 B1 | 6/2002 | Sheridan et al. |
| 6,451,304 B1 | 9/2002 | Friedmann et al. |
| 6,576,463 B1 | 6/2003 | Kasahara et al. |
| 6,712,612 B1 | 3/2004 | Tung |
| 6,899,871 B2 | 5/2005 | Kasahara et al. |
| 8,722,867 B2 | 5/2014 | Gruber et al. |
| 8,829,173 B2 | 9/2014 | Gruber et al. |
| 9,320,738 B2 | 4/2016 | Gruber et al. |
| 9,642,921 B2 | 5/2017 | Rubbins et al. |
| 9,663,834 B2 | 5/2017 | Jolly et al. |
| 9,669,049 B2 | 6/2017 | Gruber et al. |
| 9,732,326 B2 | 8/2017 | Gruber et al. |
| 9,889,133 B2 | 2/2018 | Gruber et al. |
| 10,035,983 B2 | 7/2018 | Gruber et al. |
| 2005/0084928 A1 | 4/2005 | Birch et al. |
| 2008/0008685 A1 | 1/2008 | Kasahara |
| 2008/0293141 A1 | 11/2008 | Chono et al. |
| 2011/0217267 A1 | 9/2011 | Gruber et al. |
| 2011/0287020 A1 | 11/2011 | Gruber et al. |

FOREIGN PATENT DOCUMENTS

| | | |
|---|---|---|
| CA | 2306634 A1 | 5/1999 |
| CN | 1277631 A | 12/2000 |
| CN | 1898379 A | 1/2007 |
| CN | 101031651 | 9/2007 |
| EP | 1795601 A1 | 6/2007 |
| JP | 6-500923 | 2/1994 |
| WO | 9921967 | 5/1999 |
| WO | 03/060101 A2 | 7/2003 |
| WO | 2004007753 A2 | 1/2004 |
| WO | 2005063970 A1 | 7/2005 |
| WO | 2005116225 A1 | 12/2005 |
| WO | 2006058231 A2 | 6/2006 |
| WO | 2010036986 A2 | 4/2010 |

OTHER PUBLICATIONS

Deleu, Laurent, Extended European Search Report, Application No. 19156480.6, European Patent Office, dated Aug. 30, 2019.

Logg, Christopher R. et al., "Tissue-specific transcriptional targeting of a replication-competent retroviral vector", Journal of Virology, vol. 76, No. 24, Dec. 2002, pp. 12783-12791.

Aim V, "Serum-Free Medium" (http://www.lifetechnologies.com/us/en/home/life-science/cell-culture/mammalian-cell-culture/specialty-media/t-cell-media/aim-v-medium.html), publication date unspecified.

Andreasen PA et al., "Plasminogen activator inhibitor type 1 biosynthesis and mRNA level are increased by dexamethasone in human fibrosarcoma cells", Mol. Cell Biol., Aug. 1987;7(8);3021-5.

Baranick, Brian Thomas, "Replication Kinetics and Genomic Stability of Three Replication-Competent Retroviral Vectors", Characterization and Utilization of Simple Replication-Competent Retroviral Vectors, 2007, University of California, Los Angeles, pp. 93-119.

Becamel, Philippe, International Preliminary Report on Patentability and Written Opinion, PCT/US2010/038996, The International Bureau of WIPO, dated Dec. 20, 2011.

Benedict, William F et al., "Tumorigenicity of Human HT1080 Fibrosarcoma X Normal Fibroblast Hybrids: Chromosome Dosage Dependency", Cancer Research, 44, 3471-3479, Aug. 1984.

Cepko, Constance, "Preparation of a Specific Retrovirus Producer Cell Line" Current Protocols in Molecular Biology, Jan. 1, 2001, John Wiley & Sons, Inc., Hoboken, NJ.

Cho, Jeong Han, International Search Report and Written Opinion, PCT/US10/38996, Korean Intellectual Property Office, dated Mar. 22, 2011.

Deleu, Laurent, Extended European Search Report issued in European Patent Application No. 10790193.6, dated Oct. 15, 2012.

(Continued)

*Primary Examiner* — Nianxiang Zou

(74) *Attorney, Agent, or Firm* — Rimon, P.C.

(57) ABSTRACT

The disclosure provide cell lines and methods for the production of vectors and viral particles useful in gene therapy.

12 Claims, 35 Drawing Sheets

Specification includes a Sequence Listing.

(56) References Cited

OTHER PUBLICATIONS

Deleu, Laurent, Office Action issued in European Patent Application No. 10790193.6, dated Jun. 10, 2013.
Deleu, Laurent, Office Action issued in European Patent Application No. 10790193.6, dated Jan. 31, 2014.
Deleu, Laurent, Communication Pursuant to Article 94(3) EPC, European Patent Application No. 10790193.6, dated Jun. 12, 2015.
Fan, Ying, Office Action issued in Chinese Patent Application No. 201080032354.4, dated Oct. 8, 2012.
Fan, Ying, Office Action issued in Chinese Patent Application No. 201080032354.4, dated Mar. 10, 2014.
Fan, Ying, Decision of Final Rejection, Chinese Patent Application No. 20100032354.4, dated May 21, 2015.
Finger et al., "Replicating retroviral vectors mediating continuous production and secretion of therapeutic gene products from cancer cells", Cancer Gene Therapy, Jan. 2005, 12, 464-474.
Genbank: AAG33626.1, published on Nov. 21, 2000, pp. 1-2, http://www.ncbi.nlm.nih.gov/protein/11245466.
Gerin PA et al., "Production of retroviral vectors for gene therapy with the human packaging cell line FLYRD18", Biotechnol. Prog., Sep.-Oct. 1999; 15(5):941-8.
Gerin et al., "Improved Production of Retroviral Vectors Under Serum-Free Conditions for the Application of Gene Therapy", Animal Cell Technology: Challenges for the 21st Century, 2002, pp. 193-197.
Ghani, K et al., "Generation of a high-titer packaging cell line for the production of retroviral vectors in suspension and serum-free media", Gene Therapy, 2007, 14, 1705-1711.
Gutjahr, Thorsten S., "Neuartige retrovirale Vektorsysteme fur die Gentherapie: Entwicklung in Suspension wachsender Verpackungszellinien", Mar. 16, 2000, pp. 1-114, Retrieved from the internet: http://elib.uni-stuttgart.de/ppus/volltexte/2000/601/pdf/gutjahrt_promotion.pdf.
Hartl et al., "Library-based selection of retroviruses selectively spreading through matrix metalloprotease-positive cells", Gene Ther., Jun. 2005; 12(11):918-926.
1Hiraoka K et al., "Tumor-selective gene expression in a hepatic metastasis model after locoregional delivery of a replication-competent retrovirus vector", Clin Cancer Res., Dec. 1, 2006; 12(23); 7108-16.
Jin Y, Cowan JA, "Targeted cleavage of HIV rev response element RNA by metallopeptide complexes", Am Chem Soc, Jan. 18, 2006; 128(2);410-1.
Klarissza Domokos, Written Opinion, Singapore Patent Application No. 201109341-6, dated Sep. 16, 2015.
Lao, W.D., Animal Cell Engineering and Transgenic Animal Pharmaceutics, Dec. 31, 2003, (See Chapter 4, Section 4.1.1. "Suspension Culture").
Lisheng, XU et al., "Preliminary study of maintaining in floating-culture system and screening side population in human breast cancer cell line MCF-7", Chinese Journal of Cancer Prevention and Treatment, 14(10): 736-740, May 2007.
Logg et al., "Adaptive Evolution of a Tagged Chimeric Gammaretrovirus: Identification of Novel cis-Acting Elements that Modulate Splicing", J. Mol. Biol., 2007, 369, 1214-1229.
Metzl C. et al., "Tissue- and Tumor-Specific Targeting of Murine Leukemia Virus-Based Replication-Competent Retroviral Vectors", J. Virol., Jul. 2006, vol. 80, No. 14, pp. 7070-7078.
Miyagi et al., "Gene therapy for prostate cancer using the cytosine deaminase/ uracil phosphoribosyltransferase suicide system", J. Gene Med., Jan. 2003; 5(1):30-7.
Mullen et al., "Tumors Expressing the Cytosine Deaminase Suicide Gene can be Eliminated in Vivo with Fluorocytosine and Induce Protective Immunity to Wild Type Tumor", Cancer Research, 54, 1503-1506, Mar. 15, 1994.
Oh et al., "Long-term microcamer suspension cultures of human embryonic stem cells", Stem Cell Research, 2009, 2, 219-230.
Paar et al., "Influence of vector design and host cell on the mechanism of recombination and emergence of mutant subpopulations of replicating retroviral vectors", BMC Molecular Biology, 2009, 10:1-14.
Pang, J.L., Cell Engineering, Dec. 31, 2007.
Rahman et al., "Effects of Storage Conditions on the Morphology and Titer of Lentiviral Vectors", Tex. J. Microsc., 44, 2013, pp. 30-36.
SFM for Animal Cell Culture in Suspension / Protocol, http://www.bioind.com/ page_13784.
Smith, Andrew D. et al., "Tissue-specific regulatory elements in mammalian promoters", Molecular Systems Biology, 2007, 3:1-8.
Tai et al., "Single-Shot, Multicycle Suicide Gene Therapy by Replication-Competent Retrovirus Vectors Achieves Long-Term Survival Benefit in Experimental Glioma", Molecular Therapy, vol. 12, No. 5, Nov. 2005, pp. 842-851.
Wang et al., "Insertion of human IL-2 gene into rat fibrosarcoma cells using retrovirus as a vector", Practical Oncology Journal, 1993, 1.
Wang et al., "Highly Efficient and Tumor-Restricted Gene Transfer to Malignant Gliomas by Replication-Competent Retroviral Vectors", Human Gene Therapy, 2003, 14:117-127.
Wu et al., Diagnostic and Therapeutic Manual for Blood Diseases, Dec. 31, 2000.
First Office Action for Chinese patent application CN201710168480.6, dated Feb. 5, 2020, 10 pages with extra 9 pages of English language equivalent or summary.
Response to First Office Action for Chinese patent application CN201710168480.6, dated Sep. 14, 2020, 13 pages.
Second Office Action for Chinese patent application CN201710168480.6, dated Feb. 5, 2021, 7 pages with extra 3 pages of English language equivalent or summary.
Junlan Pang (Chief Editor), Cell Engineering, Higher Education Press, 1st Edition, pp. 247-249, publication date: Jun. 2007 ISBN 978-7-04-021756-8.
Hiraoka et al., "Tumor-Selective Gene Expression in a Hepatic Metastasis Model after Locoregional Delivery of a Replication-Competent Retrovirus Vector," Clin Cancer Res 2006;12(23):7108-7116 http://clincancerres.aacrjournals.org/content/12/23/7108.

```
     CMV Promotor (1-582)>>>
     |
1    TAGTTATTAATAGTAATCAATTACGGGGTCATTAGTTCATAGCCCATATATGGAGTTCCG  60
     ATCAATAATTATCATTAGTTAATGCCCCAGTAATCAAGTATCGGGTATATACCTCAAGGC 61   CGTTACATAACTTACGGTAAATGGCCCGCCTGGCTGACCGCCCAACGACCCCCGCCCATT 120
     GCAATGTATTGAATGCCATTTACCGGGCGGACCGACTGGCGGGTTGCTGGGGGCGGGTAA 121  GACGTCAATAATGACGTATGTTCCCATAGTAACGCCAATAGGGACTTTCCATTGACGTCA 180
     CTGCAGTTATTACTGCATACAAGGGTATCATTGCGGTTATCCCTGAAAGGTAACTGCAGT 181  ATGGGTGGAGTATTTACGGTAAACTGCCCACTTGGCAGTACATCAAGTGTATCATATGCC 240
     TACCCACCTCATAAATGCCATTTGACGGGTGAACCGTCATGTAGTTCACATAGTATACGG 241  AAGTACGCCCCTATTGACGTCAATGACGGTAAATGGCCCGCCTGGCATTATGCCCAGTA 300
     TTCATGCGGGGATAACTGCAGTTACTGCCATTTACCGGGCGGACCGTAATACGGGTCAT Eco105I
                                           |
                                           SnaBI
                                           |
                                           BstSNI
                                           |
301  CATGACCTTATGGGACTTTCCTACTTGGCAGTACATCTACGTATTAGTCATCGCTATTAC 360
     GTACTGGAATACCCTGAAAGGATGAACCGTCATGTAGATGCATAATCAGTAGCGATAATG 361  CATGGTGATGCGGTTTTGGCAGTACATCAATGGGCGTGGATAGCGGTTTGACTCACGGGG 420
     GTACCACTACGCCAAAACCGTCATGTAGTTACCCGCACCTATCGCCAAACTGAGTGCCCC 421  ATTTCCAAGTCTCCACCCCATTGACGTCAATGGGAGTTTGTTTTGGCACCAAAATCAACG 480
     TAAAGGTTCAGAGGTGGGGTAACTGCAGTTACCCTCAAACAAAACCGTGGTTTTAGTTGC 481  GGACTTTCCAAAATGTCGTAACAACTCCGCCCCATTGACGCAAATGGGCGGTAGGCGTGT 540
     CCTGAAAGGTTTTACAGCATTGTTGAGGCGGGGTAACTGCGTTTACCCGCCATCCGCACA R region (583-650)>>>
                                                 |
541  ACGGTGGGAGGTCTATATAAGCAGAGCTGGTTTAGTGAACCGGCGCCAGTCCTCCGATTG 600
     TGCCACCCTCCAGATATATTCGTCTCGACCAAATCACTTGGCCGCGGTCAGGAGGCTAAC
```

FIGURE 3E

U5 region (651-1202)>>>

601  ACTGAGTCGCCCGGGTACCCGTGTATCCAATAAACCCTCTTGCAGTTGCATCCGACTTGT 660
     TGACTCAGCGGGCCCATGGGCACATAGGTTATTTGGGAGAACGTCAACGTAGGCTGAACA

661  GGTCTCGCTGTTCCTTGGGAGGGTCTCCTCTGAGTGATTGACTACCCGTCAGCGGGGGTC 720
     CCAGAGCGACAAGGAACCCTCCCAGAGGAGACTCACTAACTGATGGGCAGTCGCCCCAG

721  TTTCATTTGGGGGCTCGTCCGGGATCGGGAGACCCCTGCCCAGGGACCACCGACCCACCA 780
     AAAGTAAACCCCGAGCAGGCCCTAGCCCTCTGGGACGGGTCCTGGTGGCTGGGTGGT

5'SS (788)

781  CCGGGAGGTAAGCTGGCCAGCAACTTATCTGTGTCTGTCCGATTGTCTAGTGTCTATGAC 840
     GGCCCTCCATTCGACCGGTCGTTGAATAGACACAGACAGGCTAACAGATCACAGATACTG

841  TGATTTTATGCGCCTGCGTCGGTACTAGTTAGCTAACTAGCTCTGTATCTGGCGGACCCG 900
     ACTAAAATACGCGGACGCAGCCATGATCAATCGATTGATCGAGACATAGACCGCCTGGGC

901  TGGTGGAACTGACGAGTTCGGAACACCCGGCCGCAACCCTGGGAGCGTCCCAGGGACTT 960
     ACCACCTTGACTGCTCAAGCCTTGTGGGCCGGCGTTGGGACCCTCTGCAGGGTCCCTGAA

961  CGGGGGCCGTTTTTGTGGCCCGACCTGAGTCCAAAAATCCCGACGTTTTGGACTCTTTG 1020
     GCCCCGGCAAAAACACCGGGCTGGACTCAGGTTTTTAGGGCTAGCAAAACCTGAGAAAC

1021 GTGCACCCCCTTAGAGGAGGGATAGGTGGTTCTGGTAGGAGACGAGAACCTAAAACAGT 1080
     CACGTGGGGGAATCTCCTCCCTATACCACCAAGACCATCCTCTGCTCTTGGATTTTGTCA

1081 TCCGCCTCCGTCTGAATTTTGCTTTGGTTTGGGACCGAAGCCGCCGCCGCGTCTTG 1140
     AGGCGGAGGCAGACTTAAAAACGAAAGCCAAACCTGGCTTCGCGCGGCGCGCAGAC

1141 TCTGCTGCAGCATCGTCTGTGGTGTCTCTGTCTGACTGTGTTTCTGTATTGTCTGAGA 1200
     AGACGACGTCGTAGCAAGACACAACAGACAGACTGACACAAAGCATAAACAGACTCT gag(1203,2819)>>>

1201 ATATGGGCCAGACTGTTACCACTCCCTTAAGTTTGACCTTAGGTCACTGGAAAGATGTCG 1260
     TATACCCGGTCTGACAATGGTGAGGGAATTCAAACTGGAATCCAGTGACCTTTCTACAGC

1261 AGGGATCGCTCACAACCAGTCGGTAGATGTCAAGAAGACGTTGGTTACCTTCTGCT 1320
     TCCCTAGCGAGTGTTGGTCAGCCATCTACAGTTCTTCTGCAACCAATGGAAGACGA

1321 CTGCAGAATGGCCAACCTTTAACGTCGGATGCCGCAACGTGACCTTTAACCGAGACC 1380
     GACGTCTTACCGGTTGGAAATTGCAGCCTACCGCGGTCTGCGTGGAAATTGGCTCTGG

1381 TCATCACCCAGGTTAAGATCAAGGTCTTTTCACTTGGCCCGCATGGACACCCAGACCAGG 1440
     AGTAGTGGGTCCAATTCTAGTTCCAGAAAAGTGGACCGGGGTACCTGTGGGTCTGGTCC

1441 TCCCCTACATCGTTGACCTGGAAGCCTTGGCCTTTGACCCCCTTCCTGGGTCAAGCCCT 1500
     AGGGGATGTAGCACTGGACCCTTTCGGAACCGGAAACTGGGGGAGGGACCCAGTTCGGA

FIGURE 3E (cont'd)

1501 TTGTACACCCTAAGCCTCCGCCTCCTCTTCCTCCATCCGCCCCGTCTCTCCCCCTTGAAC 1560
     AACATGTGGGATTCGGAGGCGGAGGAGAAGGAGGTAGGCGGGGCAGAGAGGGGGAACTTG

1561 CTCCTCGTTCGACCCCGCCTCGATCCTCCCTTTATCCAGCCCTCACTCCTTCTCTAGGCG 1620
     GAGGAGCAAGCTGGGGCGGAGCTAGGAGGGAAATAGGTCGGGAGTGAGGAAGAGATCCGC

1621 CCAAACCTAAACCTCAAGTTCTTTCTGACAGTGGGGGGCCGCTCATCGACCTACTTACAG 1680
     GGTTTGGATTTGGAGTTCAAGAAAGACTGTCACCCCCGGCGAGTAGCTGGATGAATGTC

1681 AAGACCCCCGCCTTATAGGGACTCAAGACCACCCCCTTCCGACAGGGACGGAAATGGTG 1740
     TTCTGGGGGCGGAATATCCCTGGGTTCTGGTGGGGAAGGCTGTCCCTGCCTTTACCAC

1741 GAGAAGCGACCCCTGCGGGAGAGGCACCGGACCCCTCCCCAATGGCATCTCGCCTACGTG 1800
     CTCTTCGCTGGGGACGCCCTCTCCGTGGCCTGGGGAGGGGTTACCGTAGAGCGGATGCAC

1801 GGAGACGGGAGCCCCCTGTGGCCGACTCCACTACCTCGCAGGCATTCCCCCTCCGCGCAG 1860
     CCTCTGCCCTCGGGGGACACCGGCTGAGGTGATGGAGCGTCCGTAAGGGGAGGCGCGTC

1861 GAGGAAACGGACAGCTTCAATACTGGCCGTTCTCCTCTTCTGACCTTTACAACTGGAAAA 1920
     CTCCTTTGCCTGTCGAAGTTATGACCGGCAAGAGGAGAAGACTGGAAATGTTGACCTTTT

1921 ATAATAACCTTCTTTTTCTGAAGATCCAGGTAAACTGACAGCTCTGATCGAGTCTGTTC 1980
     TATTATTGGAAGAAAAAGACTTCTAGGTCCATTTGACTGTCGAGACTAGCTCAGACAAG

1981 TCATCACCCATCAGCCCACCTGGGACGACTGTCAGCAGCTGTTGGGGACTCTGCTGACCG 2040
     AGTAGTGGGTAGTCGGGTGGACCCTGCTGACAGTCGTCGACAACCCCTGAGACGACTGGC

3121 ACTTTGAGGGATCAGGAGCCCAGGTTATGGGACCAATGGGGCAGCCCCTGCAAGTGTTGA 3180
     TGAAACTCCCTAGTCCTCGGGTCCAATACCCTGGTTACCCCGTCGGGGACGTTCACAACT

3181 CCCTAAATATAGAAGATGAGCATCGGCTACATGAGACCTCAAAAGAGCCAGATGTTTCTC 3240
     GGGATTTATATCTTCTACTCGTAGCCGATGTACTCTGGAGTTTTCTCGGTCTACAAAGAG

3241 TAGGGTCCACATGGCTGTCTGATTTTCCTCAGGCCTGGGCGGAAACCGGGGCATGGGAC 3300
     ATCCCAGGTGTACCGACAGACTAAAAGGAGTCCGGACCCGCCTTTGGCCCCCGTACCCTG

3'SS (3314)

3301 TGGCAGTTCGCCAAGCTCCTCTGATCATACCTCTGAAAGCAACCTCTACCCCGTGTCCA 3360
     ACCGTCAAGCGGTTCGAGGAGACTAGTATGGAGACTTTCGTTGGAGATGGGGCACAGGT

3361 TAAAACAATACCCCATGTCACAAGAAGCCAGACTGGGGATCAAGCCCCACATACAGAGAC 3420
     ATTTTGTTATGGGGTACAGTGTTCTTCGGTCTGACCCCTAGTTCGGGGTGTATGTCTCTG

3421 TGTTGGACCAGGGAATACTGGTACCCTGCCAGTCCCCCTGGAACACGCCCCTGCTACCCG 3480
     ACAACCTGGTCCCTTATGACCATGGGACGGTCAGGGGGACCTTGTGCGGGGACGATGGGC

3481 TTAAGAAACCAGGGACTAATGATTATAGGCCTGTCCAGGATCTGAGAGAAGTCAACAAGC 3540
     AATTCTTTGGTCCCTGATTACTAATATCCGGACAGGTCCTAGACTCTCTTCAGTTGTTCG

FIGURE 3E (cont'd)

```
3541 GGGTGGAAGACATCCACCCCACCGTGCCCAACCCTTACAACCTCTTGAGCGGGCTCCCAC 3600
     CCCACCTTCTGTAGGTGGGGTGGCACGGGTTGGGAATGTTGGAGAACTCGCCCGAGGGTG

3601 CGTCCCACCAGTGGTACACTGTGCTTGATTTAAAGGATGCCTTTTTCTGCCTGAGACTCC 3660
     GCAGGGTGGTCACCATGTGACACGAACTAAATTTCCTACGGAAAAAGACGGACTCTGAGG

PfeI
                                                           |
                                                          TflI
                                                           |
3661 ACCCCACCAGTCAGCCTCTCTTCGCCTTTGAGTGGAGAGATCCAGAGATGGGAATCTCAG 3720
     TGGGGTGGTCAGTCGGAGAAGCGGAAACTCACCTCTCTAGGTCTCTACCCTTAGAGTC

MfeI
        |
       MunI
        |
3721 GACAATTGACCTGGACCAGACTCCCACAGGGTTTCAAAAACAGTCCCACCCTGTTTGATG 3780
     CTGTTAACTGGACCTGGTCTGAGGGTGTCCCAAAGTTTTTGTCAGGGTGGGACAAACTAC

MroI
                           |
                          BseAI
                           |
                          Bsp13I
                           |
                          BspEI
                           |
                          Kpn2I
                           |
                          AccIII
                           |
3781 AGGCACTGCACAGAGACCTAGCAGACTTCCGGATCCAGCACCCAGACTTGATCCTGCTAC 3840
     TCCGTGACGTGTCTCTGGATCGTCTGAAGGCCTAGGTCGTGGGTCTGAACTAGGACGATG

3841 AGTACGTGGATGACTTACTGCTGGCCGCCACTTCTGAGCTAGACTGCCAACAAGGTACTC 3900
     TCATGCACCTACTGAATGACGACCGGCGGTGAAGACTCGATCTGACGGTTGTTCCATGAG

3121 ACTTTGAGGGATCAGGAGCCCAGGTTATGGGACCAATGGGGCAGCCCCTGCAAGTGTTGA 3180
     TGAAACTCCCTAGTCCTCGGGTCCAATACCCTGGTTACCCCGTCGGGGACGTTCACAACT

3181 CCCTAAATATAGAAGATGAGCATCGGCTACATGAGACCTCAAAAGAGCCAGATGTTTCTC 3240
     GGGATTTATATCTTCTACTCGTAGCCGATGTACTCTGGAGTTTTCTCGGTCTACAAAGAG

3241 TAGGGTCCACATGGCTGTCTGATTTTCCTCAGGCCTGGGCGGAAACCGGGGCATGGGAC 3300
     ATCCCAGGTGTACCGACAGACTAAAAGGAGTCCGGACCCGCCTTTGGCCCCGTACCCTG
```

3301 TGGCAGTTCGCCAAGCTCCTCTGATCATACCTCTGAAAGCAACCTCTACCCCGTGTCCA 3360
     ACCGTCAAGCGGTTCGAGGAGACTAGTATGGAGACTTTCGTTGGAGATGGGGGCACAGGT

3361 TAAACAATACCCCATGTCACAAGAAGCCAGACTGGGGATCAAGCCCCACATACAGAGAC 3420
     ATTTTGTTATGGGGTACAGTGTTCTTCGGTCTGACCCCTAGTTCGGGGTGTATGTCTCTG

3421 TGTTGGACCAGGGAATACTGGTACCCTGCCAGTCCCCCTGGAACACGCCCCTGCTACCCG 3480
     ACAACCTGGTCCCTTATGACCATGGGACGGTCAGGGGGACCTTGTGCGGGGACGATGGGC

3481 TTAAGAAACCAGGGACTAATGATTATAGGCCTGTCCAGGATCTGAGAGAAGTCAACAAGC 3540
     AATTCTTTGGTCCCTGATTACTAATATCCGGACAGGTCCTAGACTCTCTTCAGTTGTTCG

3541 GGGTGGAAGACATCCACCCCACCGTGCCCAACCCTTACAACCTCTTGAGCGGGCTCCCAC 3600
     CCCACCTTCTGTAGGTGGGGTGGCACGGGTTGGGAATGTTGGAGAACTCGCCCGAGGGTG

3601 CGTCCCACCAGTGGTACACTGTGCTTGATTTAAAGGATGCCTTTTTCTGCCTGAGACTCC 3660
     GCAGGGTGGTCACCATGTGACACGAACTAAATTTCCTACGGAAAAAGACGGACTCTGAGG

PfeI
                                                            |
                                                           TfiI
                                                            |
3661 ACCCCACCAGTCAGCCTCTCTTCGCCTTTGAGTGGAGAGATCCAGAGATGGGAATCTCAG 3720
     TGGGGTGGTCAGTCGGAGAGAAGCGGAAACTCACCTCTCTAGGTCTCTACCCTTAGAGTC

MfeI
      |
     MunI
      |
3721 GACAATTGACCTGGACCAGACTCCCACAGGGTTTCAAAAACAGTCCCACCCTGTTTGATG 3780
     CTGTTAACTGGACCTGGTCTGAGGGTGTCCCAAAGTTTTTGTCAGGGTGGGACAAACTAC

MroI
                         |
                        BseAI
                         |
                        Bsp13I
                         |
                        BspEI
                         |
                        Kpn2I
                         |
                        AccIII
                         |
3781 AGGCACTGCACAGAGACCTAGCAGACTTCCGGATCCAGCACCCAGACTTGATCCTGCTAC 3840
     TCCGTGACGTGTCTCTGGATCGTCTGAAGGCCTAGGTCGTGGGTCTGAACTAGGACGATG

FIGURE 3E (cont'd)

```
3841  AGTACGTGGATGACTTACTGCTGGCCGCCACTTCTGAGCTAGACTGCCAACAAGGTACTC 3900
      TCATGCACCTACTGAATGACGACCGGCGGTGAAGACTCGATCTGACGGTTGTTCCATGAG

3901  GGGCCCTGTTACAAACCCTAGGGAACCTCGGGTATCGGGCCTCGGCCAAGAAAGCCCAAA 3960
      CCCGGGACAATGTTTGGGATCCCTTGGAGCCCATAGCCCGGAGCCGGTTCTTTCGGGTTT

3961  TTTGCCAGAAACAGGTCAAGTATCTGGGGTATCTTCTAAAAGAGGGTCAGAGATGGCTGA 4020
      AAACGGTCTTTGTCCAGTTCATAGACCCCATAGAAGATTTTCTCCCAGTCTCTACCGACT

4021  CTGAGGCCAGAAAAGAGACTGTGATGGGGCAGCCTACTCCGAAGACCCCTCGACAACTAA 4080
      GACTCCGGTCTTTTCTCTGACACTACCCCGTCGGATGAGGCTTCTGGGGAGCTGTTGATT

4081  GGGAGTTCCTAGGGACGGCAGGCTTCTGTCGCCTCTGGATCCCTGGGTTTGCAGAAATGG 4140
      CCCTCAAGGATCCCTGCCGTCCGAAGACAGCGGAGACCTAGGGACCCAAACGTCTTTACC

4141  CAGCCCCCTTGTACCCTCTCACCAAAACGGGGACTCTGTTTAATTGGGGCCCAGACCAAC 4200
      GTCGGGGAACATGGGAGAGTGGTTTTGCCCCTGAGACAAATTAACCCCGGGTCTGGTTG

4201  AAAAGGCCTATCAAGAAATCAAGCAAGCTCTTCTAACTGCCCCAGCCCTGGGGTTGCCAG 4260
      TTTTCCGGATAGTTCTTTAGTTCGTTCGAGAAGATTGACGGGGTCGGGACCCCAACGGTC

SalI
                                    |
4261  ATTTGACTAAGCCCTTTGAACTCTTGTCGACGAGAAGCAGGGCTACGCCAAAGGTGTCC 4320
      TAAACTGATTCGGGAAACTTGAGAACAGCTGCTCTTCGTCCCGATGCGGTTTCCACAGG

4321  TAACGCAAAAACTGGGACCTTGGCGTCGGCCGGTGGCCTACCTGTCCAAAAAGCTAGACC 4380
      ATTGCGTTTTTGACCCTGGAACCGCAGCCGGCCACCGGATGGACAGGTTTTTCGATCTGG

4381  CAGTAGCAGCTGGGTGGCCCCCTTGCCTACGGATGGTAGCAGCCATTGCCGTACTGACAA 4440
      GTCATCGTCGACCCACCGGGGGAACGGATGCCTACCATCGTCGGTAACGGCATGACTGTT

4441  AGGATGCAGGCAAGCTAACCATGGGACAGCCACTAGTCATTCTGGCCCCCATGCAGTAG 4500
      TCCTACGTCCGTTCGATTGGTACCCTGTCGGTGATCAGTAAGACCGGGGGGTACGTCATC

4501  AGGCACTAGTCAAACAACCCCCGACCGCTGGCTTTCCAACGCCCGGATGACTCACTATC 4560
      TCCGTGATCAGTTTGTTGGGGGGCTGGCGACCGAAAGGTTGCGGGCCTACTGAGTGATAG

4561  AGGCCTTGCTTTTGGACACGGACCGGGTCCAGTTCGGACCGGTGGTAGCCCTGAACCCGG 4620
      TCCGGAACGAAAACCTGTGCCTGGCCCAGGTCAAGCCTGGCCACCATCGGGACTTGGGCC

4621  CTACGCTGCTCCCACTGCCTGAGGAAGGGCTGCAACACAACTGCCTTGATATCCTGGCCG 4680
      GATGCGACGAGGGTGACGGACTCCTTCCCGACGTTGTGTTGACGGAACTATAGGACCGGC

4681  AAGCCCACGGAACCCGACCCGACCTAACGGACCAGCCGCTCCCAGACGCCGACCACACCT 4740
      TTCGGGTGCCTTGGGCTGGGCTGGATTGCCTGGTCGGCGAGGGTCTGCGGCTGGTGTGGA

4741  GGTACACGGATGGAAGCAGTCTCTTACAAGAGGGACAGCGTAAGGCGGGAGCTGCGGTGA 4800
      CCATGTGCCTACCTTCGTCAGAGAATGTTCTCCCTGTCGCATTCCGCCCTCGACGCCACT
```

FIGURE 3E (cont'd)

```
                                                            BlpI
                                                            |
                                                            CelII
                                                            |
                                                            Bpu1102I
                                                            |
                                                            Bsp1720I
                                                            |
4801  CCACCGAGACCGAGGTAATCTGGGCTAAAGCCCTGCCAGCCGGACATCCGCTCAGCGGG  4860
      GGTGGCTCTGGCTCCATTAGACCCGATTTCGGGACGGTCGGCCCTGTAGGCGAGTCGCCC

4861  CTGAACTGATAGCACTCACCCAGGCCCTAAAGATGGCAGAAGGTAAGAAGCTAAATGTTT  4920
      GACTTGACTATCGTGAGTGGGTCCGGGATTTCTACCGTCTTCCATTCTTCGATTTACAAA

4921  ATACTGATAGCCGTTATGCTTTTGCTACTGCCCATATCCATGGAGAAATATACAGAAGGC  4980
      TATGACTATCGGCAATACGAAAACGATGACGGGTATAGGTACCTCTTTATATGTCTTCCG

4981  GTGGGTTGCTCACATCAGAAGGCAAAGAGATCAAAAATAAAGACGAGATCTTGGCCCTAC  5040
      CACCCAACGAGTGTAGTCTTCCGTTTCTCTAGTTTTTATTTCTGCTCTAGAACCGGGATG

5041  TAAAAGCCCTCTTTCTGCCCAAAAGACTTAGCATAATCCATTGTCCAGGACATCAAAAGG  5100
      ATTTTCGGGAGAAAGACGGGTTTTCTGAATCGTATTAGGTAACAGGTCCTGTAGTTTTCC

5101  GACACAGCGCCGAGGCTAGAGGCAACCGGATGGCTGACCAAGCGGCCCGAAAGGCAGCCA  5160
      CTGTGTCGCGGCTCCGATCTCCGTTGGCCTACCGACTGGTTCGCCGGGCTTTCCGTCGGT

5161  TCACAGAGACTCCAGACACCTCTACCCTCCTCATAGAAAATTCATCACCCTACACCTCAG  5220
      AGTGTCTCTGAGGTCTGTGGAGATGGGAGGAGTATCTTTTAAGTAGTGGGATGTGGAGTC

5221  AACATTTTCATTACACAGTCACTGATATAAAGGACCTAACCAAGTTGGGGGCCATTTATG  5280
      TTGTAAAAGTAATGTGTCACTGACTATATTTCCTGGATTGGTTCAACCCCCGGTAAATAC

5281  ATAAAACAAAGAAGTATTGGGTCTACCAAGGAAAACCTGTGATGCCTGACCAGTTTACTT  5340
      TATTTTGTTTCTTCATAACCCAGATGGTTCCTTTTGGACACTACGGACTGGTCAAATGAA

5341  TTGAATTATTAGACTTTCTTCATCAGCTGACTCACCTCAGCTTCTCAAAAATGAAGGCTC  5400
      AACTTAATAATCTGAAAGAAGTAGTCGACTGACTGGAGTCGAAGAGTTTTACTTCCGAG

5401  TCCTAGAGAGAAGCCACAGTCCCTACTACATGCTGAACCCGGATCGAACACTCAAAAATA  5460
      AGGATCTCTCTTCGGTGTCAGGGATGATGTACGACTTGGGCCTAGCTTGTGAGTTTTTAT

5461  TCACTGAGACCTGCAAAGCTTGTGCACAAGTCAACGCCAGCAAGTCTGCCGTTAAACAGG  5520
      AGTGACTCTGGACGTTTCGAACACGTGTTCAGTTGCGGTCGTTCAGACGGCAATTTGTCC

SacII
      |
      SgrBI
      |
      Cfr42I
      |
      Sfr303I
      |
      KspI
      |
```

FIGURE 3E (cont'd)

5521 GAACTAGGGTCCGCGGGCATCGGCCCGGCACTCATTGGGAGATCGATTTCACCGAGATAA 5580
     CTTGATCCCAGGCGCCCGTAGCCGGGCCGTGAGTAACCCTCTAGCTAAAGTGGCTCTATT

5581 AGCCCGGATTGTATGGCTATAAATATCTTCTAGTTTTTATAGATACCTTTCTGGCTGGA 5640
     TCGGGCCTAACATACCGATATTTATAGAAGATCAAAAATATCTATGGAAAAGACCGACCT

5641 TAGAAGCCTTCCCAACCAAGAAAGAAACCGCCAAGGTCGTAACCAAGAAGCTACTAGAGG 5700
     ATCTTCGGAAGGGTTGGTTCTTTCTTTGGCGGTTCCAGCATTGGTTCTTCGATGATCTCC

PaeI
                           |
                          BbuI
                           |
                          SpaHI
                           |
                          SphI
                           |
5701 AGATCTTCCCCAGGTTCGGCATGCCTCAGGTATTGGGAACTGACAATGGGCCTGCCTTCG 5760
     TCTAGAAGGGGTCCAAGCCGTACGGAGTCCATAACCCTTGACTGTTACCCGGACGGAAGC

6901 CTTCCAAGGGGCTACTCGAGGGGGCAGATGCAACCCTCTAGTCCTAGAATTCACTGATGC 6960
     GAAGGTTCCCCGATGAGCTCCCCCGTCTACGTTGGGAGATCAGGATCTTAAGTGACTACG

6961 AGGAAAAAAGGCTAACTGGGACGGGCCCAAATCGTGGGGACTGAGACTGTACCGGACAGG 7020
     TCCTTTTTTCCGATTGACCCTGCCCGGGTTTAGCACCCCTGACTCTGACATGGCCTGTCC

7021 AACAGATCCTATTACCATGTTCTCCCTGACCCGGCAGGTCCTTAATGTGGGACCCCGAGT 7080
     TTGTCTAGGATAATGGTACAAGAGGGACTGGGCCGTCCAGGAATTACACCCTGGGGCTCA

7081 CCCCATAGGGCCCAACCCAGTATTACCCGACCAAAGACTCCCTTCCTCACCAATAGAGAT 7140
     GGGGTATCCCGGGTTGGGTCATAATGGGCTGGTTTCTGAGGGAAGGAGTGGTTATCTCTA

7141 TGTACCGGCTCCACAGCCACCTAGCCCCCTCAATACCAGTTACCCCCCTTCCACTACCAG 7200
     ACATGGCCGAGGTGTCGGTGGATCGGGGGAGTTATGGTCAATGGGGGAAGGTGATGGTC

7201 TACACCCTCAACCTCCCCTACAAGTCCAAGTGTCCTACAGCCACCCCCAGGAACTGGAGA 7260
     ATGTGGGAGTTGGAGGGATGTTCAGGTTCACAGGGTGTCGGTGGGGTCCTTGACCTCT

7261 TAGACTACTAGCTCTAGTCAAAGGAGCCTATCAGGCGCTTAACCTCACCAATCCCGACAA 7320
     ATCTGATGATCGAGATCAGTTTCCTCGGATAGTCCGCGAATTGGAGTGGTTAGGGCTGTT

7321 GACCCAAGAATGTTGGCTGTGCTTAGTGTCGGGACCTCCTTATTACGAAGGAGTAGCGGT 7380
     CTGGGTTCTTACAACCGACACGAATCACAGCCCTGGAGGAATAATGCTTCCTCATCGCCA

7381 CGTGGGCACTTATACCAATCATTCCACCGCTCCGGCCAACTGTACGGCCACTTCCCAACA 7440
     GCACCCGTGAATATGGTTAGTAAGGTGGCGAGGCCGGTTGACATGCCGGTGAAGGGTTGT

```
                                EcoT22I
                                  |
                                 NsiI
                                  |
                                Mph1103I
                                  |
                                 Zsp2I
                                  |
                                 BfrBI
                                  | |
7441   TAAGCTTACCCTATCTGAAGTGACAGGACAGGGCCTATGCATGGGGGCAGTACCTAAAAC 7500
       ATTCGAATGGGATAGACTTCACTGTCCTGTCCCGGATACGTACCCCGTCATGGATTTTG

NaeI
                                  |
                                 PdiI
                                  |
                                 MroNI
                                  | |
                                 NgoMIV
                                  | |
7501   TCACCAGGCCTTATGTAACACCACCCAAAGCGCCGGCTCAGGATCCTACTACCTTGCAGC 7560
       AGTGGTCCGGAATACATTGTGGTGGGTTTCGCGGCCGAGTCCTAGGATGATGGAACGTCG

AleI
                                                               |
                                                              OliI
                                                               |
7561   ACCCGCCGGAACAATGTGGGCTTGCAGCACTGGATTGACTCCCTGCTTGTCCACCACGGT 7620
       TGGGCGGCCTTGTTACACCCGAACGTCGTGACCTAACTGAGGGACGAACAGGTGGTGCCA

7621   GCTCAATCTAACCACAGATTATTGTGTATTAGTTGAACTCTGGCCCAGAGTAATTTACCA 7680
       CGAGTTAGATTGGTGTCTAATAACACATAATCAACTTGAGACCGGGTCTCATTAAATGGT

6901   CTTCCAAGGGGCTACTCGAGGGGCAGATGCAACCCTCTAGTCCTAGAATTCACTGATGC 6960
       GAAGGTTCCCCGATGAGCTCCCCCGTCTACGTTGGGAGATCAGGATCTTAAGTGACTACG

6961   AGGAAAAAAGGCTAACTGGGACGGGCCCAAATCGTGGGGACTGAGACTGTACCGGACAGG 7020
       TCCTTTTTTCCGATTGACCCTGCCCGGGTTTAGCACCCCTGACTCTGACATGGCCTGTCC

7021   AACAGATCCTATTACCATGTTCTCCCTGACCCGGCAGGTCCTTAATGTGGGACCCCGAGT 7080
       TTGTCTAGGATAATGGTACAAGAGGGACTGGGCCGTCCAGGAATTACACCCTGGGGCTCA
```

FIGURE 3E (cont'd)

```
7081  CCCCATAGGGCCCAACCCAGTATTACCCGACCAAAGACTCCCTTCCTCACCAATAGAGAT  7140
      GGGGTATCCCGGGTTGGGTCATAATGGGCTGGTTTCTGAGGGAAGGAGTGGTTATCTCTA

7141  TGTACCGGCTCCACAGCCACCTAGCCCCCTCAATACCAGTTACCCCCCTTCCACTACCAG  7200
      ACATGGCCGAGGTGTCGGTGGATCGGGGGAGTTATGGTCAATGGGGGGAAGGTGATGGTC

7201  TACACCCTCAACCTCCCCTACAAGTCCAAGTGTCCCACAGCCACCCCCAGGAACTGGAGA  7260
      ATGTGGGAGTTGGAGGGGATGTTCAGGTTCACAGGGTGTCGGTGGGGTCCTTGACCTCT

7261  TAGACTACTAGCTCTAGTCAAAGGAGCCTATCAGGCGCTTAACCTCACCAATCCCGACAA  7320
      ATCTGATGATCGAGATCAGTTTCCTCGGATAGTCCGCGAATTGGAGTGGTTAGGGCTGTT

7321  GACCCAAGAATGTTGGCTGTGCTTAGTGTCGGGACCTCCTTATTACGAAGGAGTAGCGGT  7380
      CTGGGTTCTTACAACCGACACGAATCACAGCCCTGGAGGAATAATGCTTCCTCATCGCCA

7381  CGTGGGCACTTATACCAATCATTCCACCGCTCCGGCCAACTGTACGGCCACTTCCCAACA  7440
      GCACCCGTGAATATGGTTAGTAAGGTGGCGAGGCCGGTTGACATGCCGGTGAAGGGTTGT
```

```
                              EcoT22I
                                |
                              NsiI
                                |
                              Mph1103I
                                |
                              Zsp2I
                                |
                              BfrBI
                              | |
```

```
7441  TAAGCTTACCCTATCTGAAGTGACAGGACAGGGCCTATGCATGGGGGCAGTACCTAAAAC  7500
      ATTCGAATGGGATAGACTTCACTGTCCTGTCCCGGATACGTACCCCCGTCATGGATTTTG
```

```
                              NaeI
                                |
                              PdiI
                                |
                              MroNI
                              | |
                              NgoMIV
                              | |
```

```
7501  TCACCAGGCCTTATGTAACACCACCCAAAGCGCCGGCTCAGGATCCTACTACCTTGCAGC  7560
      AGTGGTCCGGAATACATTGTGGTGGGTTTCGCGGCCGAGTCCTAGGATGATGGAACGTCG
```

FIGURE 3E (cont'd)

```
                                                              AleI
                                                               |
                                                              OliI
                                                               |
7561  ACCCGCCGGAACAATGTGGGCTTGCAGCACTGGATTGACTCCCTGCTTGTCCACCACGGT  7620
      TGGGCGGCCTTGTTACACCCGAACGTCGTGACCTAACTGAGGGACGAACAGGTGGTGCCA

7621  GCTCAATCTAACCACAGATTATTGTGTATTAGTTGAACTCTGGCCCAGAGTAATTTACCA  7680
      CGAGTTAGATTGGTGTCTAATAACACATAATCAACTTGAGACCGGGTCTCATTAAATGGT

7681  CTCCCCCGATTATATGTATGGTCAGCTTGAACAGCGTACCAAATATAAAAGAGAGCCAGT  7740
      GAGGGGGCTAATATACATACCAGTCGAACTTGTCGCATGGTTTATATTTTCTCTCGGTCA

7741  ATCATTGACCCTGGCCCTTCTACTAGGAGGATTAACCATGGGAGGGATTGCAGCTGGAAT  7800
      TAGTAACTGGGACCGGGAAGATGATCCTCCTAATTGGTACCCTCCCTAACGTCGACCTTA

7801  AGGGACGGGGACCACTGCCTTAATTAAAACCCAGCAGTTTGAGCAGCTTCATGCCGCTAT  7860
      TCCCTGCCCCTGGTGACGGAATTAATTTTGGGTCGTCAAACTCGTCGAAGTACGGCGATA

7861  CCAGACAGACCTCAACGAAGTCGAAAAGTCAATTACCAACCTAGAAAAGTCACTGACCTC  7920
      GGTCTGTCTGGAGTTGCTTCAGCTTTTCAGTTAATGGTTGGATCTTTTCAGTGACTGGAG

7921  GTTGTCTGAAGTAGTCCTACAGAACCGCAGAGGCCTAGATTTGCTATTCCTAAAGGAGGG  7980
      CAACAGACTTCATCAGGATGTCTTGGCGTCTCCGGATCTAAACGATAAGGATTTCCTCCC

7981  AGGTCTCTGCGCAGCCCTAAAAGAAGAATGTTGTTTTATGCAGACCACACGGGGCTAGT  8040
      TCCAGAGACGCGTCGGGATTTTCTTCTTACAACAAAAATACGTCTGGTGTGCCCCGATCA

8041  GAGAGACAGCATGGCCAAATTAAGAGAAAGGCTTAATCAGAGACAAAAACTATTTGAGAC  8100
      CTCTCTGTCGTACCGGTTTAATTCTCTTTCCGAATTAGTCTCTGTTTTTGATAAACTCTG

NspV
                      |
                     BstBI
                      |
                     Bsp119I
                      |
                     AsuII
                      |
                     Csp45I
                      |
                     SfuI
                      |
                     Bpu14I
                      |
                     BspT104I
                      |
8101  AGGCCAAGGATGGTTCGAAGGGCTGTTTAATAGATCCCCCTGGTTTACCACCTTAATCTC  8160
      TCCGGTTCCTACCAAGCTTCCCGACAAATTATCTAGGGGGACCAAATGGTGGAATTAGAG
```

FIGURE 3E (cont'd)

```
8161  CACCATCATGGGACCTCTAATAGTACTCTTACTGATCTTACTCTTTGGACCTTGCATTCT 8220
      GTGGTAGTACCCTGGAGATTATCATGAGAATGACTAGAATGAGAAACCTGGAACGTAAGA

8221  CAATCGATTGGTCCAATTTGTTAAAGACAGGATCTCAGTGGTCCAGGCTCTGGTTTTGAC 8280
      GTTAGCTAACCAGGTTAAACAATTTCTGTCCTAGAGTCACCAGGTCCGAGACCAAAACTG

IRES reg(8327,8876)>>>
                                              |
                                              MluI(8325)
                                              | |
8281  TCAGCAATATCACCAGCTAAAACCCATAGAGTACGAGCCATGAACGCGTTACTGGCCGAA 8340
      AGTCGTTATAGTGGTCGATTTTGGGTATCTCATGCTCGGTACTTGCGCAATGACCGGCTT ires_emcv reg(8378,8876)>>>
                                         |
8341  GCCGCTTGGAATAAGGCCGGTGTGCGTTTGTCTATATGTTATTTTCCACCATATTGCCGT 8400
      CGGCGAACCTTATTCCGGCCACACGCAAACAGATATACAATAAAAGGTGGTATAACGGCA 8401  CTTTTGGCAATGTGAGGGCCCGGAAACCTGGCCCTGTCTTCTTGACGAGCATTCCTAGGG 8460
      GAAAACCGTTACACTCCCGGGCCTTTGGACCGGGACAGAAGAACTGCTCGTAAGGATCCC 8461  GTCTTTCCCCTCTCGCCAAAGGAATGCAAGGTCTGTTGAATGTCGTGAAGGAAGCAGTTC 8520
      CAGAAAGGGGAGAGCGGTTTCCTTACGTTCCAGACAACTTACAGCACTTCCTTCGTCAAG 8521  CTCTGGAAGCTTCTTGAAGACAAACAACGTCTGTAGCGACCCTTTGCAGGCAGCGGAACC 8580
      GAGACCTTCGAAGAACTTCTGTTTGTTGCAGACATCGCTGGGAAACGTCCGTCGCCTTGG 8581  CCCCACCTGGCGACAGGTGCCTCTGCGGCCAAAAGCCACGTGTATAAGATACACCTGCAA 8640
      GGGGTGGACCGCTGTCCACGGAGACGCCGGTTTTCGGTGCACATATTCTATGTGGACGTT 8641  AGGCGGCACAACCCCAGTGCCACGTTGTGAGTTGGATAGTTGTGGAAAGAGTCAAATGGC 8700
      TCCGCCGTGTTGGGGTCACGGTGCAACACTCAACCTATCAACACCTTTCTCAGTTTACCG 8701  TCTCCTCAAGCGTATTCAACAAGGGGCTGAAGGATGCCCAGAAGGTACCCCATTGTATGG 8760
      AGAGGAGTTCGCATAAGTTGTTCCCCGACTTCCTACGGGTCTTCCATGGGGTAACATACC 8761  GATCTGATCTGGGGCCTCGGTGCACATGCTTTACATGTGTTTAGTCGAGGTTAAAAAAAC 8820
      CTAGACTAGACCCCGGAGCCACGTGTACGAAATGTACACAAATCAGCTCCAATTTTTTTG
```

FIGURE 3E (Cont'd)

```
                                                          yCD2 (8877,9353)>>>
                                                          |
                                                          PsiI(8874)
                                                          | |
8821  GTCTAGGCCCCCGAACCACGGGGACGTGGTTTTCCTTTGAAAAACACGATTATAAATGG  8880
      CAGATCCGGGGGCTTGGTGCCCCTGCACCAAAAGGAAACTTTTTGTGCTAATATTTACC

8881  TGACCGGCGGCATGGCCTCCAAGTGGGATCAAAAGGGCATGGATATCGCTTACGAGGAGG  8940
      ACTGGCCGCCGTACCGGAGGTTCACCCTAGTTTTCCCGTACCTATAGCGAATGCTCCTCC

8941  CCCTGCTGGGCTACAAGGAGGGCGGCGTGCCTATCGGCGGCTGTCTGATCAACAACAAGG  9000
      GGGACGACCCGATGTTCCTCCCGCCGCACGGATAGCCGCCGACAGACTAGTTGTTGTTCC

9001  ACGGCAGTGTGCTGGGCAGGGGCCACAACATGAGGTTCCAGAAGGGCTCCGCCACCCTGC  9060
      TGCCGTCACACGACCCGTCCCCGGTGTTGTACTCCAAGGTCTTCCCGAGGCGGTGGGACG

9061  ACGGCGAGATCTCCACCCTGGAGAACTGTGGCAGGCTGGAGGGCAAGGTGTACAAGGACA  9120
      TGCCGCTCTAGAGGTGGGACCTCTTGACACCGTCCGACCTCCCGTTCCACATGTTCCTGT

9121  CCACCCTGTACACCACCCTGTCCCCTTGTGACATGTGTACCGGCGCTATCATCATGTACG  9180
      GGTGGGACATGTGGTGGGACAGGGGAACACTGTACACATGGCCGCGATAGTAGTACATGC

9181  GCATCCCTAGGTGTGTGATCGGCGAGAACGTGAACTTCAAGTCCAAGGGCGAGAAGTACC  9240
      CGTAGGGATCCACACACTAGCCGCTCTTGCACTTGAAGTTCAGGTTCCCGCTCTTCATGG

9241  TGCAAACCAGGGGCCACGAGGTGGTGGTTGTTGACGATGAGAGGTGTAAGAAGCTGATGA  9300
      ACGTTTGGTCCCCGGTGCTCCACCACCAACAACTGCTACTCTCCACATTCTTCGACTACT

NotI(9356)
                                                          |
                                                          CciNI
                                                          |
9301  AGCAGTTCATCGACGAGAGGCCTCAGGACTGGTTCGAGGATATCGGCGAGTAAGCGGCCG  9360
      TCGTCAAGTAGCTGCTCTCCGGAGTCCTGACCAAGCTCCTATAGCCGCTCATTCGCCGGC

U3 Region(9405,9854)>>>
                                                          |
9361  CAGATAAAATAAAAGATTTTATTTAGTCTCCAGAAAAAGGGGGGAATGAAAGACCCCACC  9420
      GTCTATTTTATTTTCTAAAATAAATCAGAGGTCTTTTTCCCCCCTTACTTTCTGGGGTGG BmtI
                    |
                    NheI
                    | |
                    AsuNHI      5_LTR2 other(9447,9998)>>>>
                    | |         |
9421  TGTAGGTTTGGCAAGCTAGCTTAAGTAACGCCATTTTGCAAGGCATGGAAAAATACATAA  9480
      ACATCCAAACCGTTCGATCGAATTCATTGCGGTAAAACGTTCCGTACCTTTTTATGTATT
```

FIGURE 3E (cont'd)

```
9481 CTGAGAATAGAGAAGTTCAGATCAAGGTCAGGAACAGATGGAACAGCTGAATATGGGCCA 9540
     GACTCTTATCTCTTCAAGTCTAGTTCCAGTCCTTGTCTACCTTGTCGACTTATACCCGGT

9541 AACAGGATATCTGTGGTAAGCAGTTCCTGCCCCGGCTCAGGGCCAAGAACAGATGGAACA 9600
     TTGTCCTATAGACACCATTCGTCAAGGACGGGGCCGAGTCCCGGTTCTTGTCTACCTTGT

9601 GCTGAATATGGGCCAAACAGGATATCTGTGGTAAGCAGTTCCTGCCCCGGCTCAGGGCCA 9660
     CGACTTATACCCGGTTTGTCCTATAGACACCATTCGTCAAGGACGGGGCCGAGTCCCGGT

9661 AGAACAGATGGTCCCCAGATGCGGTCCAGCCCTCAGCAGTTTCTAGAGAACCATCAGATG 9720
     TCTTGTCTACCAGGGGTCTACGCCAGGTCGGGAGTCGTCAAAGATCTCTTGGTAGTCTAC

9721 TTTCCAGGGTGCCCCAAGGACCTGAAATGACCCTGTGCCTTATTTGAACTAACCAATCAG 9780
     AAAGGTCCCACGGGGTTCCTGGACTTTACTGGGACACGGAATAAACTTGATTGGTTAGTC
```

```
                                              SacI
                                               |
                                              SstI
                                               |
                         PauI                 Pspl24BI
                          |                    |
                         BsePI                EcoICRI
                          |                    | |
                         BssHII               Ecl136II
                          |                    | |
9781 TTCGCTTCTCGCTTCTGTTCGCGCGCTTCTGCTCCCGAGCTCAATAAAAGAGCCCACAA 9840
     AAGCGAAGAGCGAAGACAAGCGCGCGAAGACGAGGGGCTCGAGTTATTTTCTCGGGTGTT
```

```
            R Region(9855,9921)>>>>
             |
9841 CCCCTCACTCGGGGCGCCAGTCCTCCGATTGACTGAGTCGCCCGGGTACCCGTGTATCCA 9900
     GGGGAGTGAGCCCCGCGGTCAGGAGGCTAACTGACTCAGCGGGCCCATGGGCACATAGGT U5 Region(9922,9998)>>>>
             |
9901 ATAAACCCTCTTGCAGTTGCATCCGACTTGTGGTCTCGCTGTTCCTTGGGAGGGTCTCCT 9960
     TATTTGGGAGAACGTCAACGTAGGCTGAACACCAGAGCGACAAGGAACCCTCCCAGAGGA 9961 CTGAGTGATTGACTACCCGTCAGCGGGGGTCTTTCATTACATGTGAGCAAAAGGCCAGCA 10020
     GACTCACTAACTGATGGGCAGTCGCCCCAGAAAGTAATGTACACTCGTTTTCCGGTCGT pBR322 origin(10045,10664)<<<
                          |
10021 AAAGGCCAGGAACCGTAAAAAGGCCGCGTTGCTGGCGTTTTTCCATAGGCTCCGCCCCC 10080
      TTTCCGGTCCTTGGCATTTTTCCGGCGCAACGACCGCAAAAAGGTATCCGAGGCGGGGG 10081 TGACGAGCATCACAAAAATCGACGCTCAAGTCAGAGGTGGCGAAACCCGACAGGACTATA 10140
      ACTGCTCGTAGTGTTTTAGCTGCGAGTTCAGTCTCCACCGCTTTGGGCTGTCCTGATAT 10141 AAGATACCAGGCGTTTCCCCCTGGAAGCTCCCTCGTGCGCTCTCCTGTTCCGACCCTGCC 10200
      TTCTATGGTCCGCAAAGGGGGACCTTCGAGGGAGCACGCGAGAGGACAAGGCTGGGACGG
```

FIGURE 3E (cont'd)

```
10201 GCTTACCGGATACCTGTCCGCCTTTCTCCCTTCGGGAAGCGTGGCGCTTTCTCAATGCTC 10260
      CGAATGGCCTATGGACAGGCGGAAAGAGGGAAGCCCTTCGCACCGCGAAAGAGTTACGAG

10261 ACGCTGTAGGTATCTCAGTTCGGTGTAGGTCGTTCGCTCCAAGCTGGGCTGTGTGCACGA 10320
      TGCGACATCCATAGAGTCAAGCCACATCCAGCAAGCGAGGTTCGACCCGACACACGTGCT

10321 ACCCCCCGTTCAGCCCGACCGCTGCGCCTTATCCGGTAACTATCGTCTTGAGTCCAACCC 10380
      TGGGGGGCAAGTCGGGCTGGCGACGCGGAATAGGCCATTGATAGCAGAACTCAGGTTGGG

10381 GGTAAGACACGACTTATCGCCACTGGCAGCAGCCACTGGTAACAGGATTAGCAGAGCGAG 10440
      CCATTCTGTGCTGAATAGCGGTGACCGTCGTCGGTGACCATTGTCCTAATCGTCTCGCTC

10441 GTATGTAGGCGGTGCTACAGAGTTCTTGAAGTGGTGGCCTAACTACGGCTACACTAGAAG 10500
      CATACATCCGCCACGATGTCTCAAGAACTTCACCACCGGATTGATGCCGATGTGATCTTC

10501 GACAGTATTTGGTATCTGCGCTCTGCTGAAGCCAGTTACCTTCGGAAAAAGAGTTGGTAG 10560
      CTGTCATAAACCATAGACGCGAGACGACTTCGGTCAATGGAAGCCTTTTTCTCAACCATC

10561 CTCTTGATCCGGCAAACAAACCACCGCTGGTAGCGGTGGTTTTTTTGTTTGCAAGCAGCA 10620
      GAGAACTAGGCCGTTTGTTGGTGGCGACCATCGCCACCAAAAAAACAAACGTTCGTCGT

10621 GATTACGCGCAGAAAAAAAGGATCTCAAGAAGATCCTTTGATCTTTTCTACGGGGTCTGA 10680
      CTAATGCGCGTCTTTTTTTCCTAGAGTTCTTCTAGGAAACTAGAAAAGATGCCCCAGACT

10681 CGCTCAGTGGAACGAAAACTCACGTTAAGGGATTTTGGTCATGAGATTATCAAAAAGGAT 10740
      GCGAGTCACCTTGCTTTTGAGTGCAATTCCCTAAAACCAGTACTCTAATAGTTTTTCCTA

10741 CTTCACCTAGATCCTTTTAAATTAAAAATGAAGTTTTAAATCAATCTAAAGTATATATGA 10800
      GAAGTGGATCTAGGAAAATTTAATTTTTACTTCAAAATTTAGTTAGATTTCATATATACT amp marker(10819,11679)<<<

10801 GTAAACTTGGTCTGACAGTTACCAATGCTTAATCAGTGAGGCACCTATCTCAGCGATCTG 10860
      CATTTGAACCAGACTGTCAATGGTTACGAATTAGTCACTCCGTGGATAGAGTCGCTAGAC

10861 TCTATTTCGTTCATCCATAGTTGCCTGACTCCCCGTCGTGTAGATAACTACGATACGGGA 10920
      AGATAAAGCAAGTAGGTATCAACGGACTGAGGGGCAGCACATCTATTGATGCTATGCCCT

10921 GGGCTTACCATCTGGCCCCAGTGCTGCAATGATACCGCGAGACCCACGCTCACCGGCTCC 10980
      CCCGAATGGTAGACCGGGGTCACGACGTTACTATGGCGCTCTGGGTGCGAGTGGCCGAGG

10981 AGATTTATCAGCAATAAACCAGCCAGCCGGAAGGGCCGAGCGCAGAAGTGGTCCTGCAAC 11040
      TCTAAATAGTCGTTATTTGGTCGGTCGGCCTTCCCGGCTCGCGTCTTCACCAGGACGTTG
```

FIGURE 3E (cont'd)

```
11041 TTTATCCGCCTCCATCCAGTCTATTAATTGTTGCCGGGAAGCTAGAGTAAGTAGTTCGCC 11100
      AAATAGGCGGAGGTAGGTCAGATAATTAACAACGGCCCTTCGATCTCATTCATCAAGCGG

11101 AGTTAATAGTTTGCGCAACGTTGTTGCCATTGCTGCAGGCATCGTGGTGTCACGCTCGTC 11160
      TCAATTATCAAACGCGTTGCAACAACGGTAACGACGTCCGTAGCACCACAGTGCGAGCAG

11161 GTTTGGTATGGCTTCATTCAGCTCCGGTTCCCAACGATCAAGGCGAGTTACATGATCCCC 11220
      CAAACCATACCGAAGTAAGTCGAGGCCAAGGGTTGCTAGTTCCGCTCAATGTACTAGGGG

11221 CATGTTGTGCAAAAAGCGGTTAGCTCCTTCGGTCCTCCGATCGTTGTCAGAAGTAAGTT 11280
      GTACAACACGTTTTTTCGCCAATCGAGGAAGCCAGGAGGCTAGCAACAGTCTTCATTCAA

11281 GGCCGCAGTGTTATCACTCATGGTTATGGCAGCACTGCATAATTCTCTTACTGTCATGCC 11340
      CCGGCGTCACAATAGTGAGTACCAATACCGTCGTGACGTATTAAGAGAATGACAGTACGG

11341 ATCCGTAAGATGCTTTTCTGTGACTGGTGAGTACTCAACCAAGTCATTCTGAGAATAGTG 11400
      TAGGCATTCTACGAAAAGACACTGACCACTCATGAGTTGGTTCAGTAAGACTCTTATCAC

11401 TATGCGGCGACCGAGTTGCTCTTGCCCGGCGTCAACACGGGATAATACCGCGCCACATAG 11460
      ATACGCCGCTGGCTCAACGAGAACGGGCCGCAGTTGTGCCCTATTATGGCGCGGTGTATC

11461 CAGAACTTTAAAAGTGCTCATCATTGGAAAACGTTCTTCGGGGCGAAAACTCTCAAGGAT 11520
      GTCTTGAAATTTTCACGAGTAGTAACCTTTTGCAAGAAGCCCCGCTTTTGAGAGTTCCTA

11521 CTTACCGCTGTTGAGATCCAGTTCGATGTAACCCACTCGTGCACCCAACTGATCTTCAGC 11580
      GAATGGCGACAACTCTAGGTCAAGCTACATTGGGTGAGCACGTGGGTTGACTAGAAGTCG

11581 ATCTTTTACTTTCACCAGCGTTTCTGGGTGAGCAAAAACAGGAAGGCAAAATGCCGCAAA 11640
      TAGAAAATGAAAGTGGTCGCAAAGACCCACTCGTTTTTGTCCTTCCGTTTTACGGCGTTT

11641 AAAGGGAATAAGGGCGACACGGAAATGTTGAATACTCATACTCTTCCTTTTTCAATATTA 11700
      TTTCCCTTATTCCCGCTGTGCCTTTACAACTTATGAGTATGAGAAGGAAAAAGTTATAAT amp prom(11721,11749)<<<

11701 TTGAAGCATTTATCAGGGTTATTGTCTCATGAGCGGATACATATTTGAATGTATTTAGAA 11760
      AACTTCGTAAATAGTCCCAATAACAGAGTACTCGCCTATGTATAAACTTACATAAATCTT

11761 AAATAAACAAATAGGGGTTCCGCGCACATTTCCCCGAAAAGTGCCACCTGACGTCTAAGA 11820
      TTTATTTGTTTATCCCCAAGGCGCGTGTAAAGGGGCTTTTCACGGTGGACTGCAGATTCT

11821 AACCATTATTATCATGACATTAACCTATAAAAATAGGCGTATCACGAGGCCCTTTCGTCT 11880
      TTGGTAATAATAGTACTGTAATTGGATATTTTTATCCGCATAGTGCTCCGGGAAAGCAGA

11881 TCAAGAATTCAT 11892
      AGTTCTTAAGTA
```

FIGURE 3E (cont'd)

1 - U87 + AC3-yCD2 (V)
2 - U87 + ACE-yCD (V)
3 - U87 (uninfected)
4 - Molecular Weight Standards

PRODUCER CELLS FOR REPLICATION COMPETENT RETROVIRAL VECTORS

CROSS REFERENCE TO RELATED APPLICATIONS

This application is a continuation of U.S. patent application Ser. No. 13/376,827, filed Dec. 7, 2011, which application is a U.S. Nation Phase application claiming priority to International Application No. PCT/US2010/038996, filed Jun. 17, 2010, which application claims priority under 35 U.S.C. § 119 from Provisional Application Ser. No. 61/218,063, filed Jun. 17, 2009, the disclosures of which are incorporated herein by reference.

TECHNICAL FIELD

The disclosure relates to methods for producing recombinant replication competent retroviral vectors, cell lines useful for producing such vectors, and methods of making and using the cell lines.

BACKGROUND

The life cycle of retroviruses involves a stage when the virus' genetic material is inserted into the genome of a host cell. This step is essential because the inserted viral nucleic acid, the provirus, is replicated through the host cell machinery.

As part of this process the RNA genome of the retrovirus is replicated through a double-stranded DNA intermediate prior to insertion into the genome of the host cell. The initial conversion of the viral RNA molecule into a double-stranded DNA (dsDNA) molecule is performed by a reverse-transcriptase. The dsDNA is then integrated into the hose cell genome by an integrase to further be replicated by the host cellular machinery. The reverse transcriptase and the integrase required for the conversion of the RNA into dsDNA and for the integration into the host genome are carried within the viral particle during infection. The proviral DNA is finally transcribed using the host machinery into multiple RNA copies. These RNA molecules are then translated into viral peptides or proteins or integrated into viral particles which are released from the cell into the medium or extracellular milieu.

A retroviral RNA genome usually comprises 6 typical regions leading to the expression of multiple proteins. These region include the gag, pol and env gene sequences associated with a packaging signal, a psi (ψ) signal and flanked by 5' and/or 3' long terminal repeats (LTR) regions. The gag gene leads to the expression of the protein components of the nucleoprotein core of the virus, while the pol gene products are involved in the synthesis polynucleotides and recombination. The env gene codes for the envelope components of the retrovirus particle. 5' and 3' LTR regions include promoters and assist in the integration of the viral genome into the chromosomal DNA of the host cell. The psi signal refers to the retroviral packaging signal that controls the efficient packaging of the RNA into the viral particle.

Because of their ability to form proviruses, retroviruses are useful to modify the genome of a target or host cell and various modifications have been made to retroviruses for use in gene therapy. Gene therapy using retroviral vectors is generally performed by adding a heterologous polynucleotide to the viral genome which encodes or produces a polypeptide or transcript of interest, packaging the recombinant genome into a viral particle and infecting a target host cell. The target cell will then incorporate the exogenous gene as being a part of a provirus.

Most retroviral vectors have been rendered "defective" to avoid uncontrolled spread and production of virions. However, little is reported about the development of replication competent retroviral vector systems.

SUMMARY

The disclosure provides cell lines and viral particle producing cells useful for producing recombinant replication competent retroviral vectors for gene therapy.

The disclosure provides retrovirus producing cell line for the production of a replication competent retrovirus particle, the cell line comprising a fibrosarcoma, an osteosarcoma or a thymoma cell line, said cell line stably expressing a recombinant retroviral genome comprising a gag gene, pol gene, env gene, a heterologous polynucleotide, and retroviral psi (Ψ) factor for the assembly of the recombinant retroviral genome. In one embodiment, the replication competent retrovirus particle is stably expressed. In another embodiment, the half life is greater than 7 days at 2-8° C. In yet another embodiment, viral particles produced from the cell line show no loss of infectivity after 12 months of storage of the cell line at 65 C. In yet another embodiment, the vector produced is approximately 100% stable for 3 months or longer and the same vector produced from a cell line transiently transfected with the same replication competent retrovirus loses at least five-fold activity at 2 to 8 weeks under the same storage conditions, compared to initial titers. In yet another embodiment the replication competent retrovirus comprises: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising an internal ribosome entry site (IRES) or regulatory nucleic acid domain operably linked to a heterologous polynucleotide, wherein the cassette is positioned 5' to the 3' LTR and 3' to the env nucleic acid domain encoding the retroviral envelope; and cis-acting sequences necessary for reverse transcription, packaging and integration in a target cell, wherein the RCR maintains higher replication competency after 6 passages compared to a pACE vector. In one embodiment, the retroviral polynucleotide sequence is derived from murine leukemia virus (MLV), Moloney murine leukemia virus (MoMLV), or Gibbon ape leukemia virus (GALV), murine mammary tumor virus (MuMTV), Rous Sarcoma Virus (RSV), Gibbon ape leukemia virus (GALV), baboon endogenous virus (BEV), and the feline virus RD114. In a further embodiment, the MLV is an amphotropic MLV. In yet another embodiment, retrovirus is a gammaretrovirus. In one embodiment, the promoter sequence is associated with a growth regulatory gene. In yet another embodiment, the nucleic acid regulatory domain comprises a pol II promoter. In yet another embodiment, the promoter sequence comprises a tissue-specific promoter sequence such as an androgen response element. In one embodiment, the androgen response element is derived from a probasin promoter.

The retroviral vector produced by the producer cell line comprise various domain. For example, the promoter comprises a CMV promoter having a sequence as set forth in SEQ ID NO:19, 20 or 22 from nucleotide 1 to about nucleotide 582 and may include modification to one or more nucleic acid bases and which is capable of directing and initiating transcription; a CMV-R-U5 domain polynucleotide comprises a sequence as set forth in SEQ ID NO:19, 20 or 22 from about nucleotide 1 to about nucleotide 1202 or sequences that are at least 95% identical to a sequence as set forth in SEQ ID NO:19, 20 or 22, wherein the polynucleotide promotes transcription of a nucleic acid molecule operably linked thereto; the gag nucleic acid domain comprises a sequence from about nucleotide number 1203 to about nucleotide 2819 of SEQ ID NO: 19 or 22 or a sequence having at least 95%, 98%, 99% or 99.8% identity thereto; the pol domain comprises a sequence from about nucleotide number 2820 to about nucleotide 6358 of SEQ ID NO:19 or 22 or a sequence having at least 95%, 98%, 99% or 99.9% identity thereto; the env domain comprises a sequence from about nucleotide number 6359 to about nucleotide 8323 of SEQ ID NO:19 or 22 or a sequence having at least 95%, 98%, 99% or 99.8% identity thereto; the IRES comprises a sequence from about nucleotide number 8327 to about nucleotide 8876 of SEQ ID NO:19 or 22 or a sequence having at least 95%, 98%, or 99% identity thereto; and the heterologous nucleic acid comprises a polynucleotide having a sequence as set forth in SEQ ID NO:3, 5, 11, 13, 15 or 17.

The disclosure also provides a cell free preparation comprising viral particles obtained from the retrovirus producing cell line described herein. In some embodiments a pharmaceutical preparation is prepared from the isolated viral particles.

The disclosure also provides a method of producing a vector producing cell line described herein comprising transforming a 293 cell line with a plasmid encoding a retroviral vector comprising from 5' to 3': a CMV-R-U5 fusion of the immediate early promoter from human cytomegalovirus to an MLV R-U5 region; a PBS, primer binding site for reverse transcriptase; a 5' splice site; ψ packaging signal; a gag coding sequence for MLV group specific antigen; a pol coding sequence for MLV polymerase polyprotein; a 3' splice site; a 4070A env coding sequence for envelope protein of MLV strain 4070A; an internal ribosome entry site (IRES) from encephalomyocarditis virus or a nucleic acid regulatory domain; a modified cytosine deaminase coding sequence; a polypurine tract; and a U3-R-U5 MLV long terminal repeat; culturing the 293 cell to produce viral particles; isolating the viral particles; infecting an HT1080 cell line with the viral particles thereby producing the viral particle producing cell line. The disclosure also provides a cell line generated by the foregoing method.

The disclosure also provides a method for producing a composition for gene therapy comprising culturing the cell line described herein to produce viral particles and substantially purifying the viral particles.

The disclosure also provides a cell bank comprising the cell line of the disclosure. In some embodiments, the cell line of the disclosure is grown in suspension. In some embodiment, the cell line of the disclosure is grown in serum free medium. In some embodiment, the cell line is grown in suspension in serum free medium.

An electronic copy of a sequence listing is submitted herewith and is incorporated herein in its entirety.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

Figure 3D:
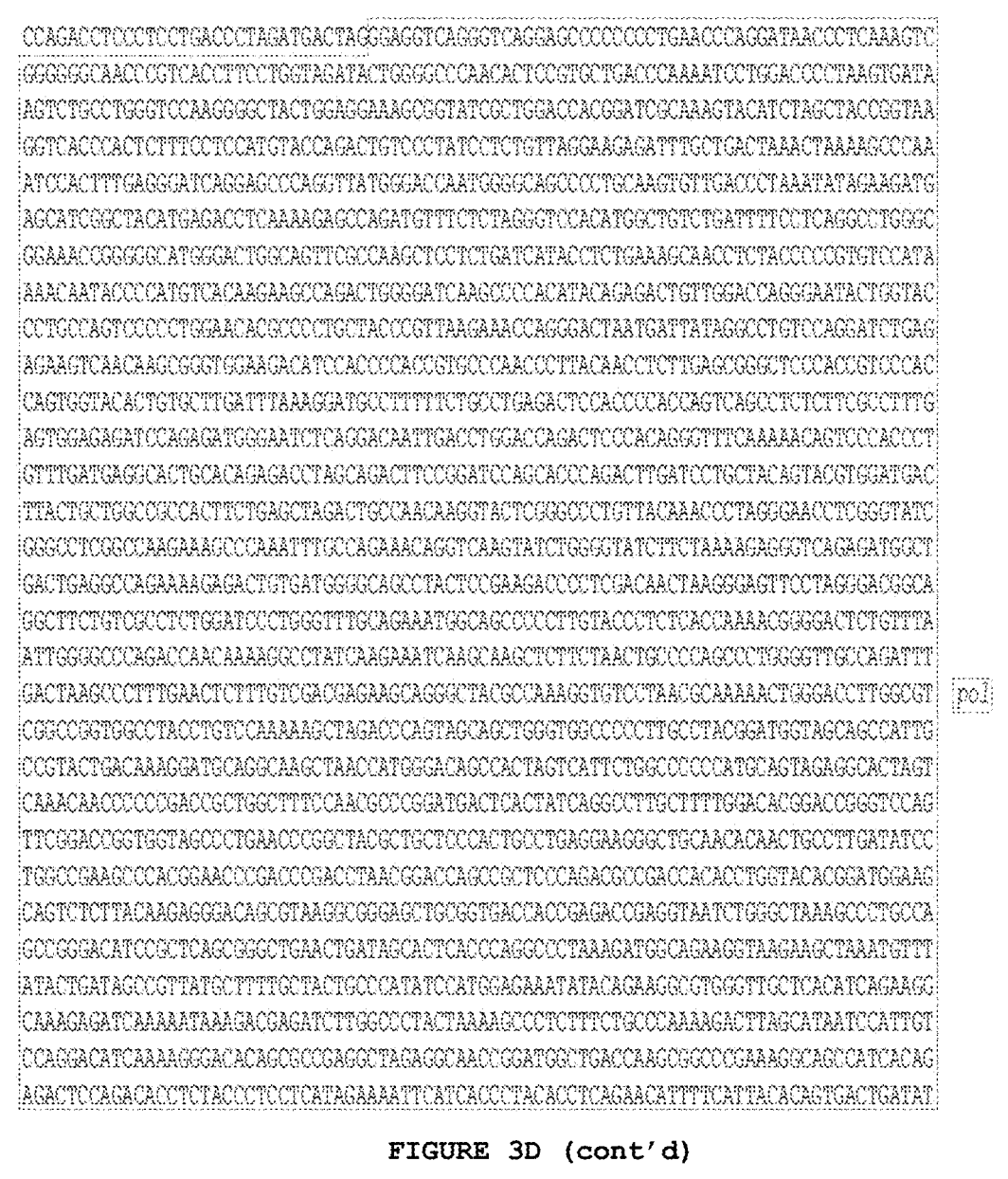

FIG. 3A-F shows (a) a schematic of a recombinant retroviral vector of the disclosure; (b and c) a plasmid map of a polynucleotide of the disclosure (CMV Promotor:1-582; R:583-650; U5:651-1202; Primer binding site (PBS):728-776; 5' slicing site:788-789; gag:1203-2819; pol:2820-6358; 3'splicing site:3314-3315; 4070A env: 6359-8323; EMCV IRES:8327-8876; yCD2:8877-9353; Poly purine tract (PPT):9386-9404; U3:9405-9854; R:9855-9921; U5:9922-9998; (d and e) a sequence of a polynucleotide of the disclosure (SEQ ID NO:19); (f) a schematic of a first and second generation RCR of the disclosure.

DETAILED DESCRIPTION

Figure 1:
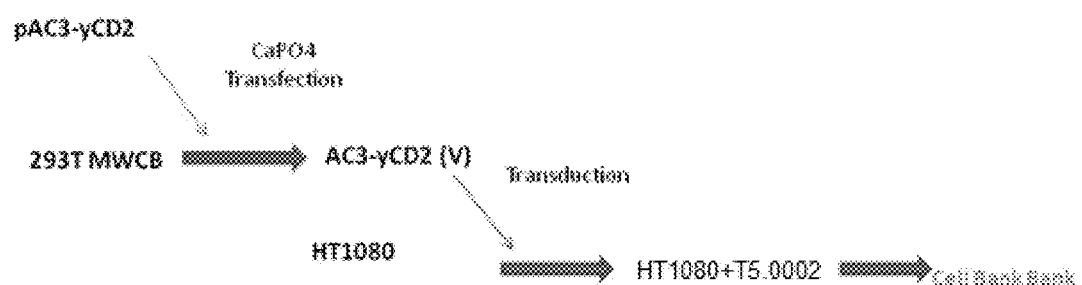
FIG. 1 shows a general process of producing a producer cell line and bank of the disclosure.
Figure 2:
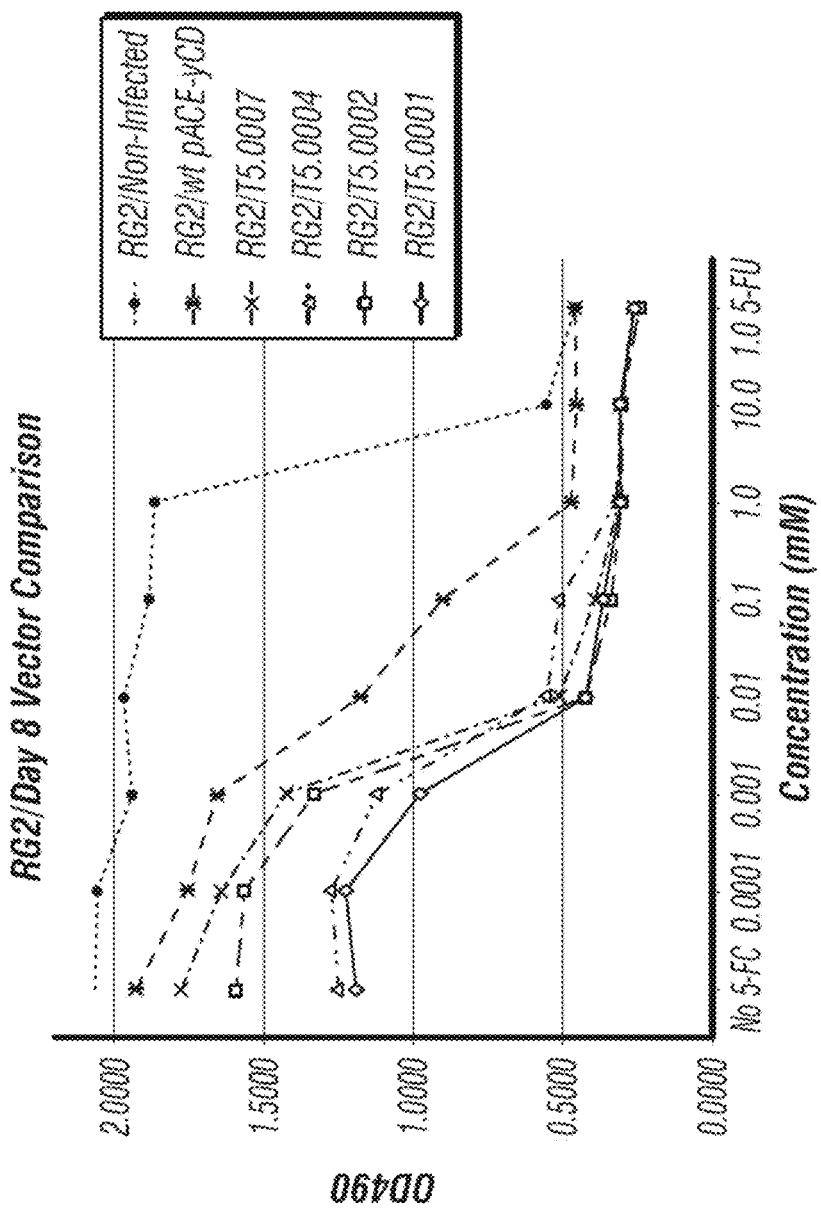
FIG. 2 shows a graph of cell killing data showing that modified vectors are more effective compared to the original wildtype CD. The graph also shows that the modified backbone (T5.0007) is more effective at killing than the backbone of pACE-CD. Also shown is a table cataloguing the various vector constructs and their names.
Figures 2, 3A:
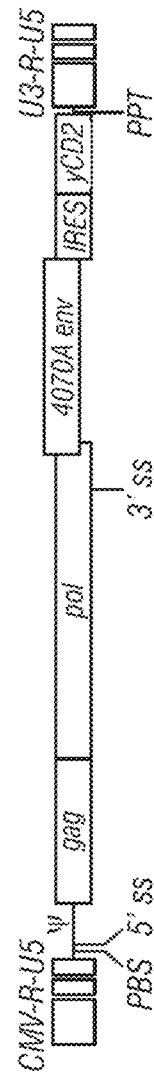
Figure 3B:
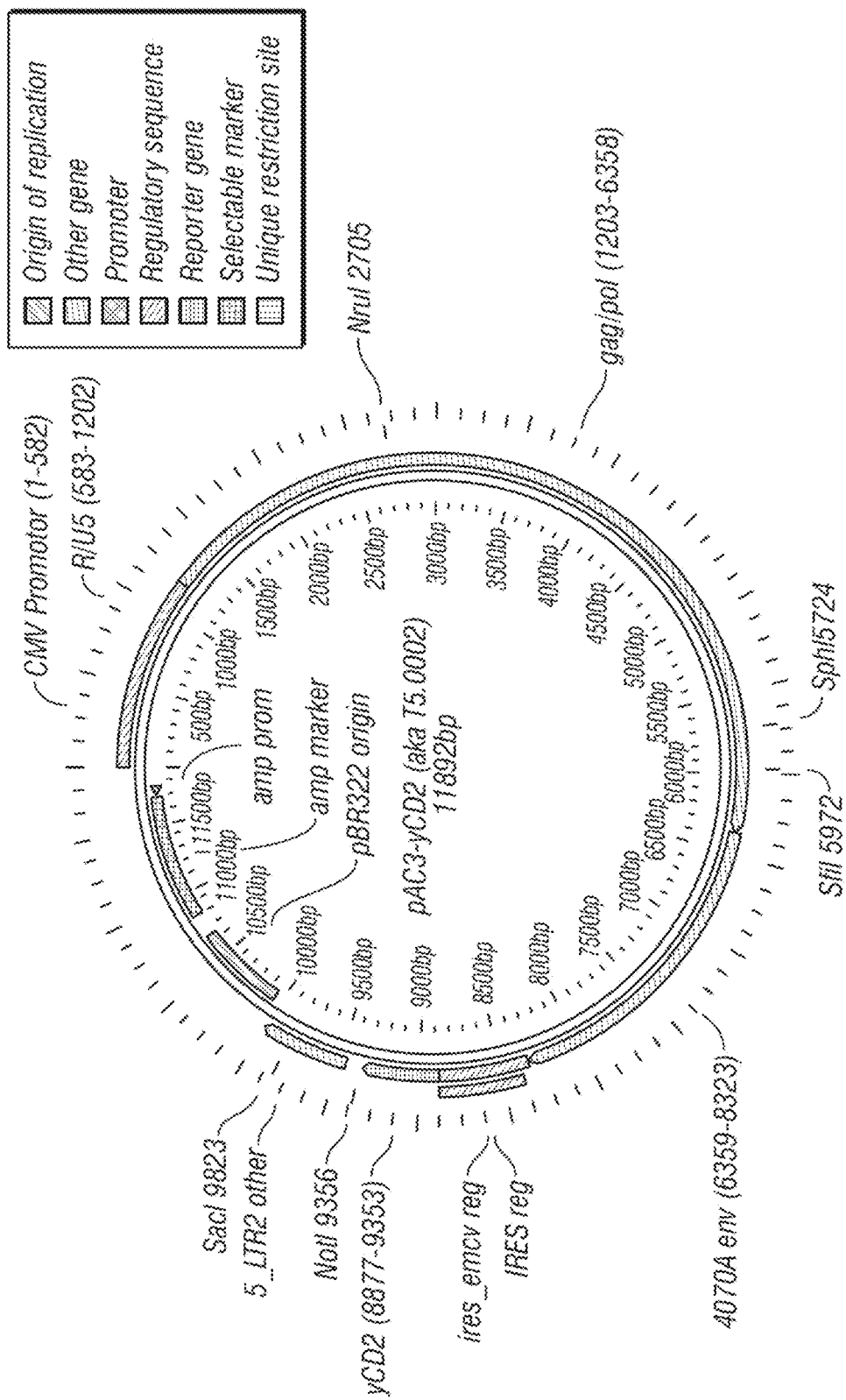
Figure 3C:
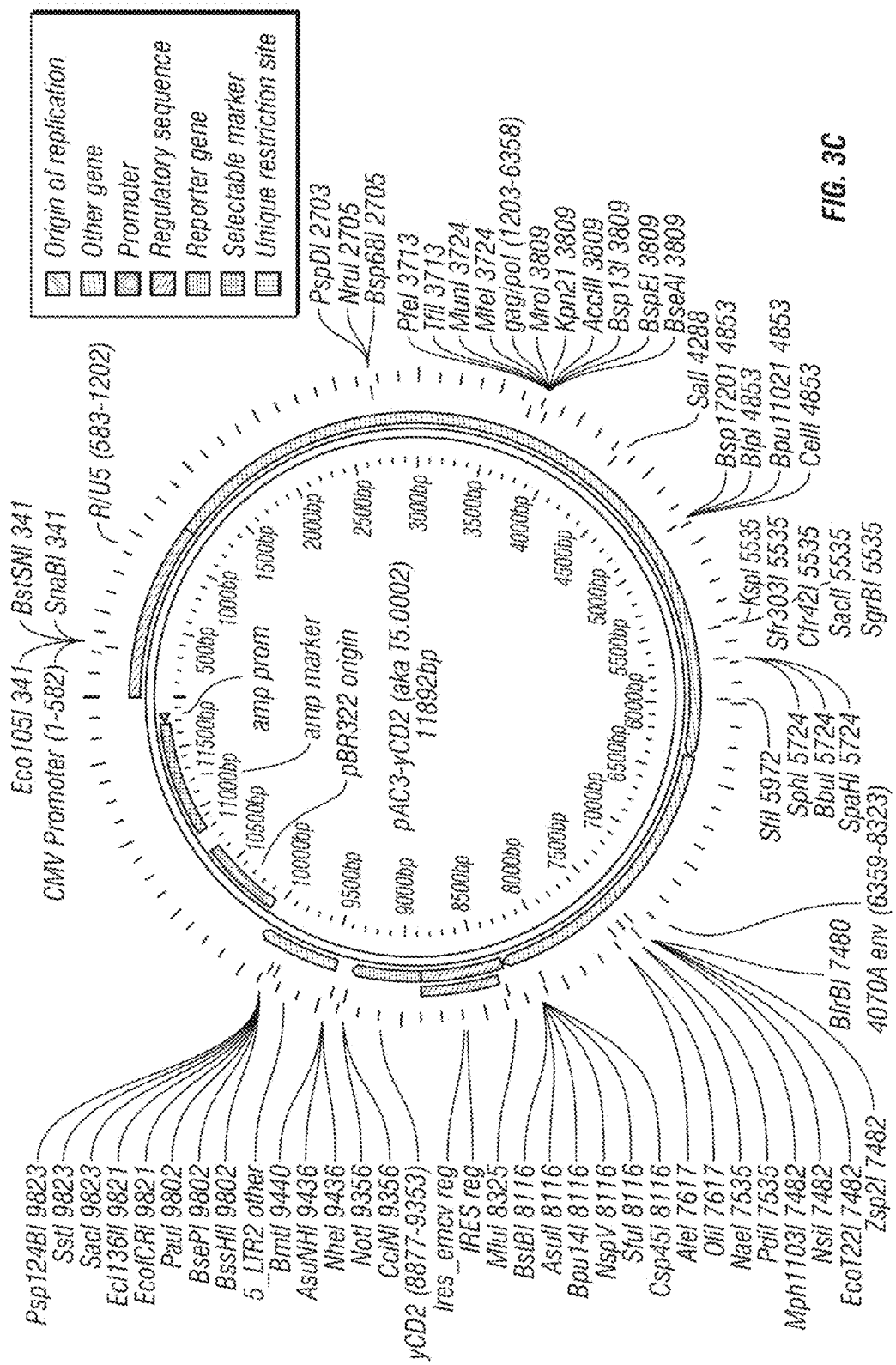
Figure 3F:
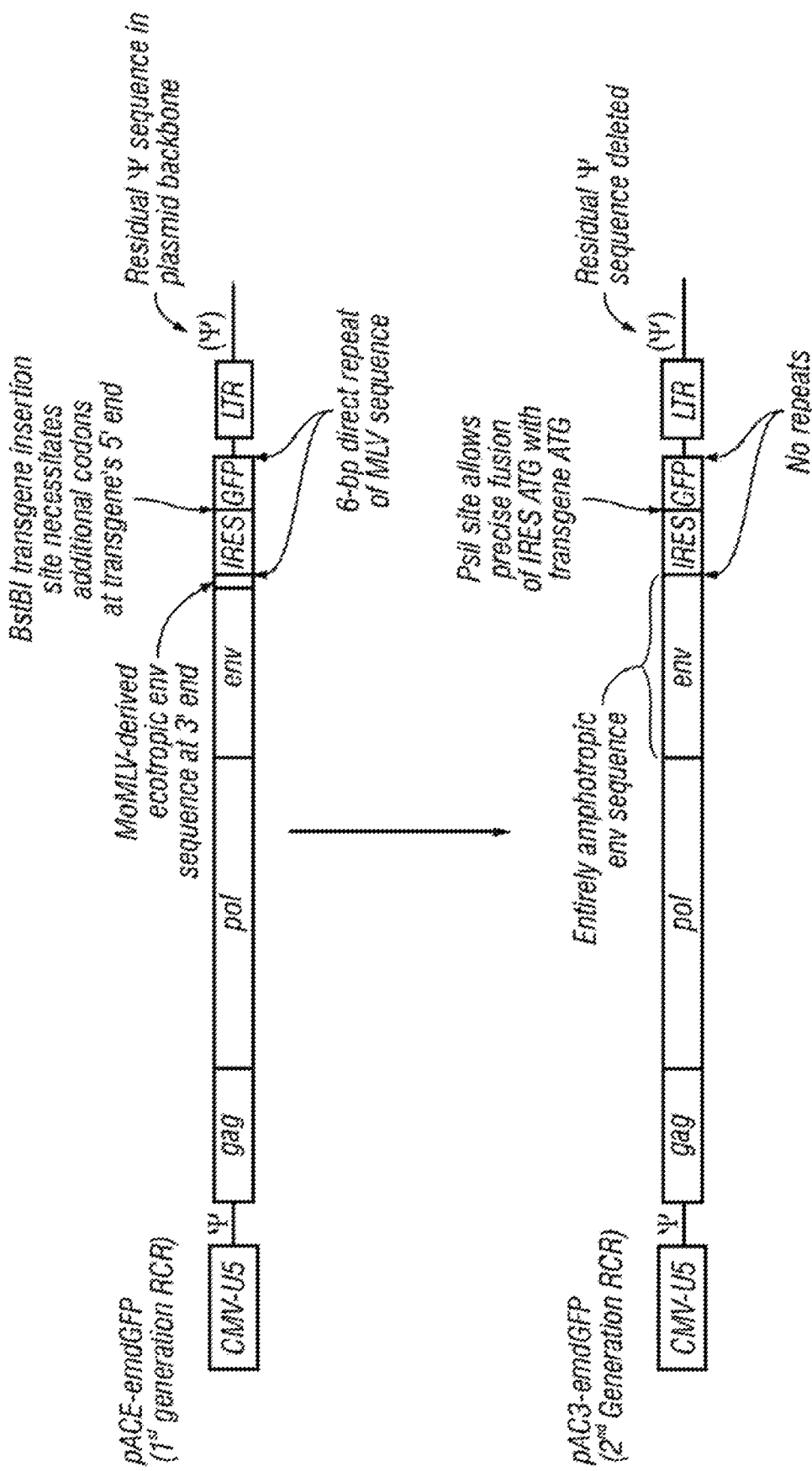
Figure 4:
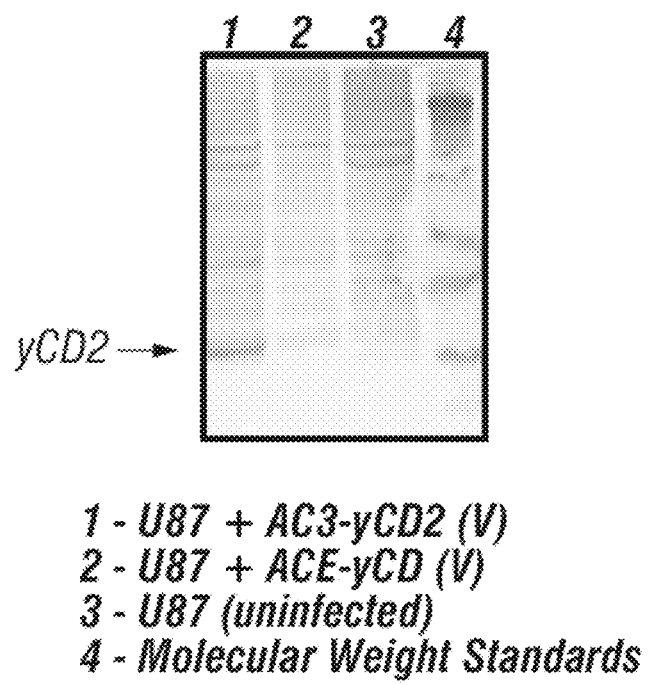
FIG. 4 shows that higher levels of yCD2 protein are observed compared to wild type yCD protein in infected U-87 cells.

As used herein and in the appended claims, the singular forms "a," "and," and "the" include plural referents unless the context clearly dictates otherwise. Thus, for example, reference to "a cell" includes a plurality of such cells and reference to "the vector" includes reference to one or more vectors, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The term "RCR" as used herein is intended to mean a replication-competent retrovirus (RCR). A replication-competent virus is a viral particle that has the capacity to replicate by itself in a host cell.

As used herein, the term "RCR plasmid vector" means a plasmid which includes all or part of a retroviral genome including 5' and 3' retroviral long-term repeat (LTR) sequences, a packaging signal (ψ), and may include one or more polynucleotides encoding a protein(s) or polypeptide (s) of interest, such as a therapeutic agent or a selectable marker. The term "therapeutic" is used in a generic sense and includes treating agents, prophylactic agents, and replacement agents.

The terms "transfecting" or "transfection" as used herein are intended to mean the transfer of at least one exogenous nucleic acid into a cell. The nucleic acid may be RNA, DNA or a combination of both. The exogenous nucleic acid refers to nucleic that is not found as a result of host cell division or host cell multiplication.

The term "virus" as used herein is intended to mean the physical virus or retrovirus particle.

The term "cell line" as used herein refers to cultured cells that can be passed (divided) more than once. The disclosure relates to cell lines that can be passed more than 2 times, up to 200 times, or more and includes any integer therebetween.

The expressions "stable expression" and "stably expressing" as used herein are intended to mean that the genetic material that is being stably expressed and/or is integrated permanently and stably in the genome of the host cell, and thus has the same expression potential over time as the native genetic material of the host cell.

The expressions "transient expression" and "transiently expressing" as used herein are intended to mean that the genetic material temporal expression period and/or is not integrated permanently and stably in the genome of the host cell, and thus does not have the same expression potential over time as the native genetic material of the host cell.

As used herein, the term "heterologous" nucleic acid sequence or transgene refers to (i) a sequence that does not normally exist in a wild-type retrovirus, (ii) a sequence that originates from a foreign species, or (iii) if from the same species, it may be substantially modified from its original form. Alternatively, an unchanged nucleic acid sequence that is not normally expressed in a cell is a heterologous nucleic acid sequence.

The term "therapeutic" as used herein refers to an action that prevents, reverses, or slows the natural course of a disease, or its symptoms. A therapeutic action can be preventive, curative or merely palliative, and does not mean that the affected human or animal patient will not die from the disease.

In one embodiment, a producer cell line of the disclosure is capable of growth in suspension or in a serum-free medium. The producer cell line can also be grown both in serum-free medium and suspension simultaneously. Although serum-free medium and the capacity to grow in suspension are the typical conditions, cells of the disclosure (e.g., 293T cells) can be cultured in an adherent manner with regular serum-containing medium to achieve particular purposes. Such purposes can be, for example, to facilitate transfection of cells or to select cell clones.

The type of producer cells used to generate the retrovirus (described more fully below) is useful for the production replication competent viral particles for gene delivery and gene therapy.

The disclosure provides a method of generating a producer cell line comprising transforming or transfecting a first mammalian cell type with an RCR plasmid vector of the disclosure, culturing the first cell type to produce retroviral particles, obtaining a cell free media from the first cell type producing the retroviral particles, wherein the cell free media comprises retroviral particles, contacting a second mammalian cell type with the media to infect the second cell type and culturing the second cell type to produce a producer cell line that produces a replication competent retroviral vector for use in transforming mammalian cells. The first cell type can be almost any mammalian cell type that is capable of producing virus after transfection and may include HeLa, COS, Chinese Hamster Ovary (CHO), and HT1080 cells, and the transfection can be with calcium phosphate or other agents such as lipid formulations known to those skilled in the art as useful for transfection.

In one embodiment, the first cell type is a human embryonic kidney cell. In another embodiment, the human embryonic kidney cell is a 293 cell (also often referred to as HEK 293 cells, 293 cells, or less precisely as HEK cells), which are a cell line originally derived from human embryonic kidney cells grown in tissue culture. HEK 293 cells were generated by transformation of cultures of normal human embryonic kidney cells with sheared adenovirus 5 DNA.

HEK 293 cells are easy to grow and transfect very readily and have been widely-used in cell biology research for many years. They are also used by the biotechnology industry to produce therapeutic proteins and viruses for gene therapy.

In another embodiment, the first cell type is a mammalian cell transformed with an SV40 Large T-antigen. In a particular embodiment, 293T HEK cells are used. An important variant of this cell line is the 293T cell line which contains the SV40 Large T-antigen allowing for episomal replication of transfected plasmids containing the SV40 origin of replication. This allows for amplification of transfected plasmids and extended temporal expression of the desired gene products.

The term "human 293 cell" as used herein includes the HEK 293T cell line, the human 293 cell line (ATCC No. CRL 1573) (Graham, et al., J. Gen. Virol., Vol. 36, pgs. 59-72 (1977)), or a cell line formed by transfecting 293 cells with one or more expression vehicles (e.g., plasmid vectors) including polynucleotides encoding various gag, pol, and env proteins. The envelope may be an amphotropic envelope, an ecotropic envelope, a xenotropic envelope, a GALV envelope, an RD114 envelope, an FeLV envelope or other retroviral envelope. The envelope may also be an envelope from a heterologous source such as an alphavirus envelope. Such cells also may include other polynucleotides such as, for example, polynucleotides encoding selectable markers. Examples of such cell lines include, but are not limited to, 293T/17 (ATCC No. CCRL 11268); Anjou 65 (ATCC No. CCRL 11269); Bosc 23 (CCRL 11270); and CAK8, also known as the Bing cell line (ATCC No. CCRL 11554).

The first cell type (e.g., HEK 293T cells) may be transformed with an RCR plasmid vector of the disclosure in any number of means including calcium phosphate and the like. Typical culture conditions for mammalian cells, particularly human 293 cells are known in the art.

Once transformed the first cell type is cultured under conditions for production of viral particles. Such conditions typically include refeeding cells in appropriate media, $CO_2$, and humidity. The culture conditions may also include the addition of antibiotics, anti-fungals, growth factors and the like. Typically the refed medium is harvested after 24, 48, 72, or 96 hours, and such a procedure is known as a transient expression transfection procedure.

The media from the cultured cells above may be used directly in further culturing. Alternatively, the viral particles in the media of cultured cells may be isolated using any number of techniques known in the art including centrifugation, size exclusion techniques, anion exchange chromatography and the like.

Where the media is used directly, the media can be added to media used in the culture of the second cell type. Where the viral particles are first substantially purified, the particles may be washed or resuspended in an appropriate buffer or media or at particular concentration for infectivity before addition to the second cell type, leading to the generation of a stable expression producer cell line.

In one embodiment, the second cell type is a human fibroscarcoma cell line. In a specific embodiment, the cell line is an HT1080 cell line or a derivative thereof. HT1080 human fibrosarcoma cell line (ATCC, Catalog #CCL-121) can be obtained directly from the American Type Culture Collection (P.O. Box 1549, Manassas, Va.). The method includes infecting the HT1080 cells with an RCR of the disclosure to provide a stably transfected host cell. The stably transfected host cell may be cultured to produce viral particles for use in gene therapy or gene delivery or may be "banked" for later use, and may be a pool of transfected cells, or a cloned cell line. The banked cells may be frozen and stored using techniques known in the art.

Typically the cells will be cultured in serum-free media. In one embodiment, the cells are culture in an animal free media or a defined media used for preparation of biologics for delivery to humans.

Unexpectedly the process described above yield viral particles for gene therapy from the stable expression producer cell line that have increased stability compared to viral particle produced by a transient expression procedure.

RCR viral particle (e.g., AC3-yCD2 (V)) can be substantially purified from the media of the HT1080+T5.002 cells. The purified vector can be washed, diluted and resuspended in an appropriate pharmaceutically acceptable carrier. Alternatively, the purified vector may be stored either by freezing of lypholization.

In one embodiment, AC3-yCD2 (V) will be administered as retroviral particles in solution. The final filled vector formulation is referred to as Toca 511, and will be supplied as an aqueous sterile solution containing the following formulation excipients (in mg/mL): sucrose 10.0, mannitol 10.0, NaCl 5.3, Human Serum Albumin (HSA, Baxter) 1.0, and ascorbic acid 0.10.

As described further herein, any number of retroviral vectors of the disclosure may be used with the producer cell line and process described herein.

In specific examples provided herein, TOCA 511 is used to demonstrate the methods and compositions of the invention. As described herein, TOCA 511 refers to a replication competent retroviral vector encoded in a plasmid designated as pAC3-yCD2 (a.k.a T5.0002). The viral vector is comprised of a replication-competent retrovirus derived from a murine leukemia virus (MLV) encoding all retroviral components (gag, pol and env) required for viral replication, with the original ecotropic envelope replaced with the amphotropic envelope from the 4070A virus.

Figure 5:
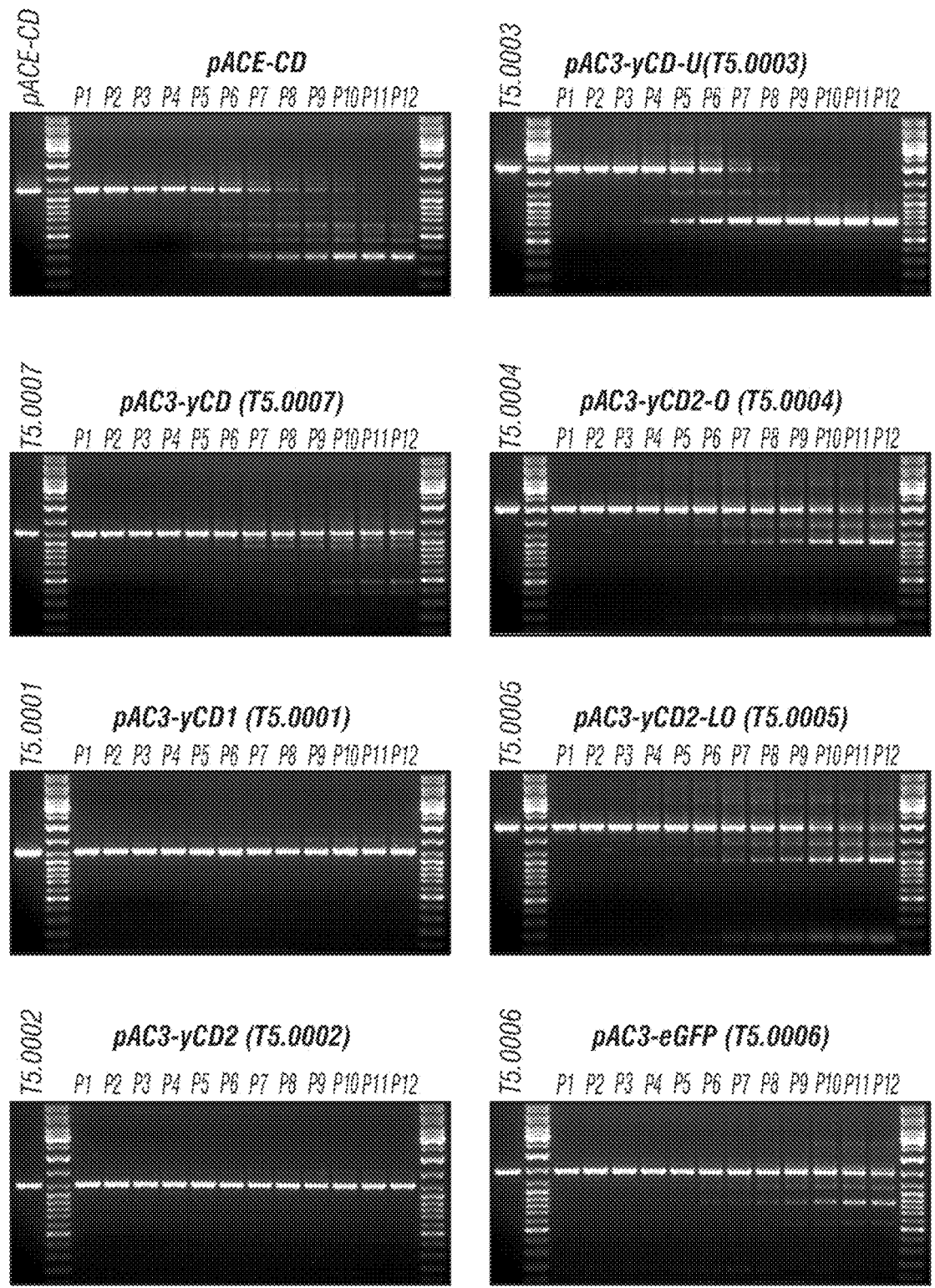
FIG. 5 shows that a vector of the disclosure is genetically stable after 12 cycles of viral passages as assessed using PCR amplification. The figure also demonstrates that the vectors of the disclosure are more stable after longer passages compared to the vector pACE-CD (Kasahara et al.). In particular pAC3-CD is more stable than pACE-CD, demonstrating that the changed backbone has made the vector more stable. In addition pACE-yCD1 (T5.0001) and -yCD2 (T5.0002) are more stable than pAC-yCD.
Figure 6A:
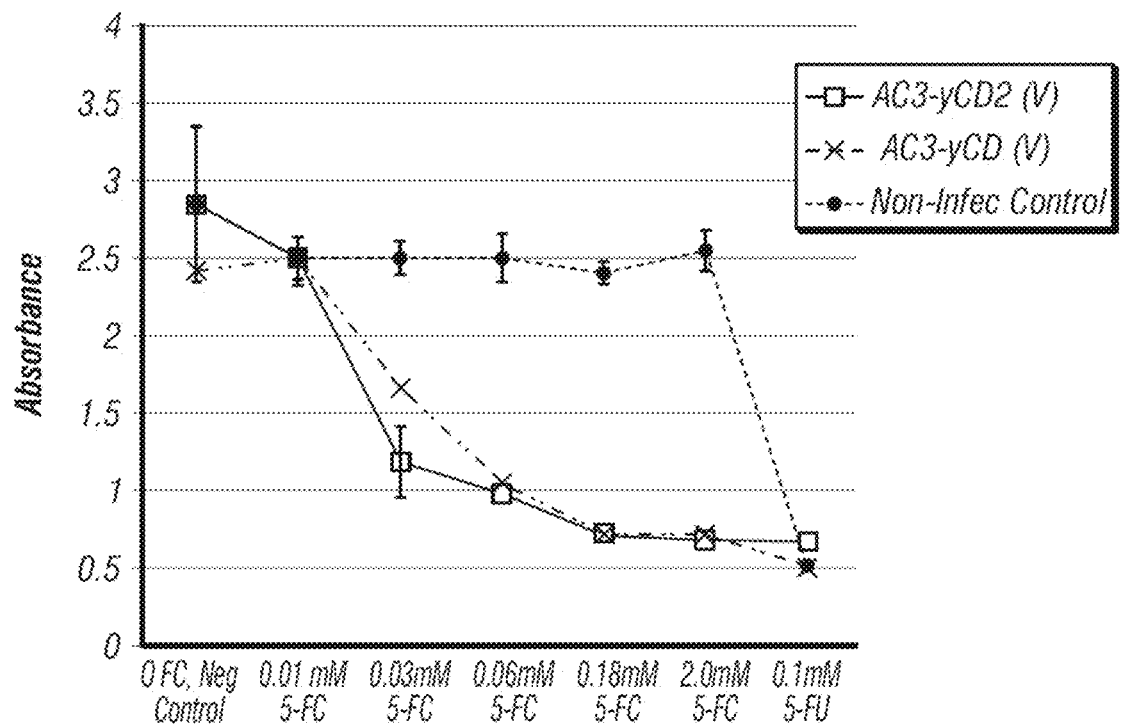
FIG. 6A-B shows cell killing activity. (A) cell killing assays; and (B) cytosine deaminase specific activity of cells in fected with different vectors. (A) shows that cytosine deaminase and vector of the disclosure kill infected cells at least as well and perhaps better than the original pACE-CD when U87 infected cells are exposed to increasing levels of 5-FC. (B) shows that the specific CD activity of the disclosure (T5.0007, T5.0001 and T5.0002) are all increased compared to pACE-CD (T5.0000), and is in the order T5.0000<T5.0007<T5.0001<T5.0002.
Figure 6B:
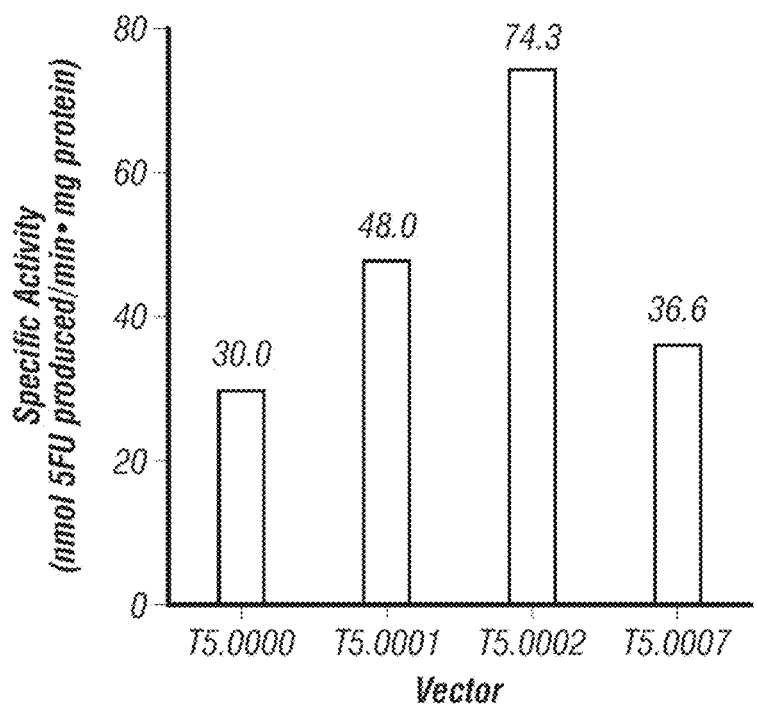
Figure 7:
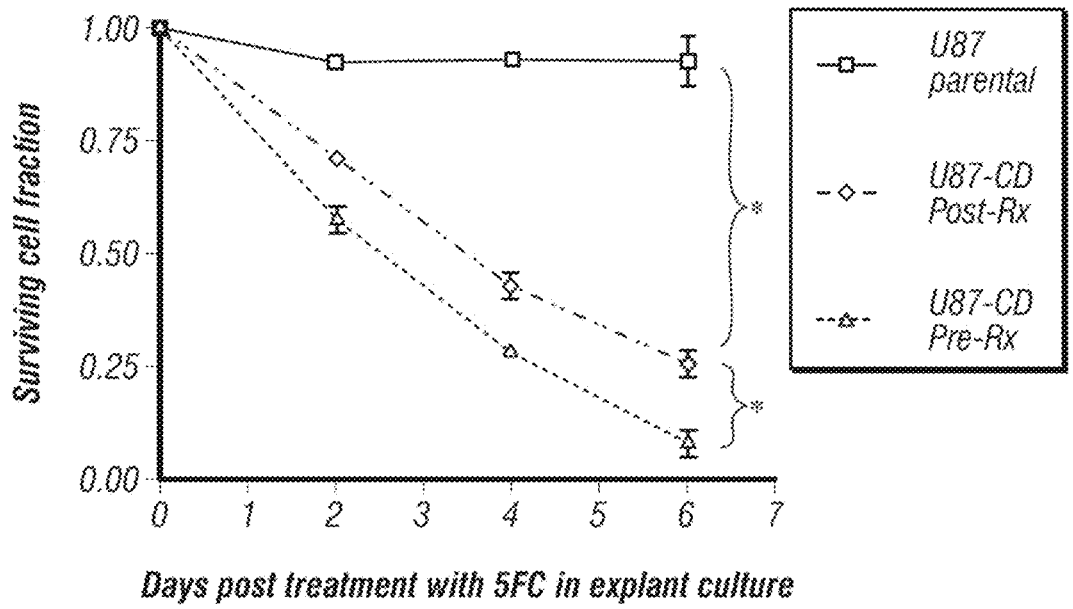
FIG. 7 shows U-87 (human) tumors treated with CD vector of the disclosure (also referred to as "Toca 511", "pAC3-yCD2(V)" and "T5.0002" see, e.g., FIG. 2) in vivo and explanted from mice treated with 4 cycles of 5-FC are still sensitive to the drug.
Figure 8:
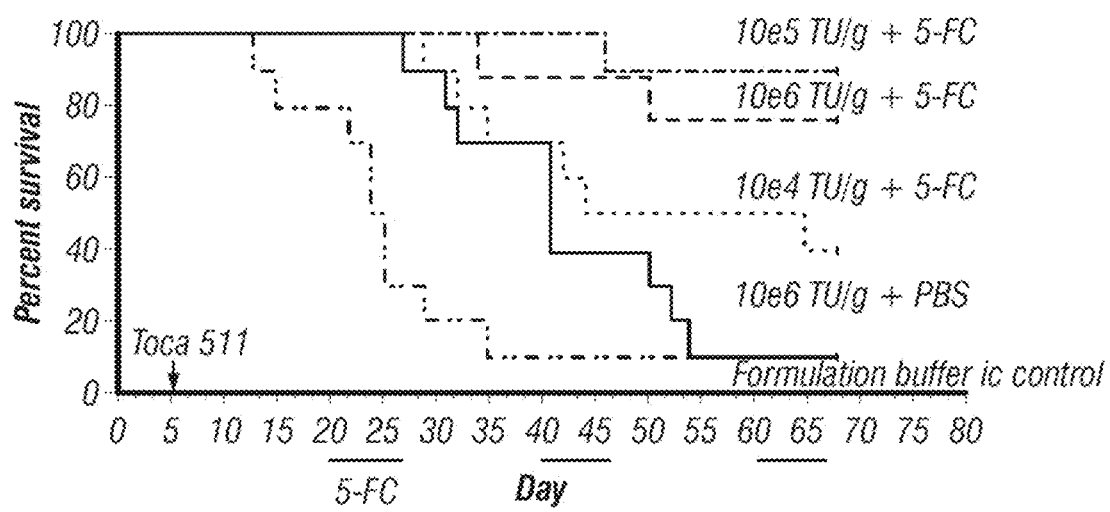
FIG. 8 shows dosing information in a human xenograft (U87) mouse model of brain cancer.
Figure 9:
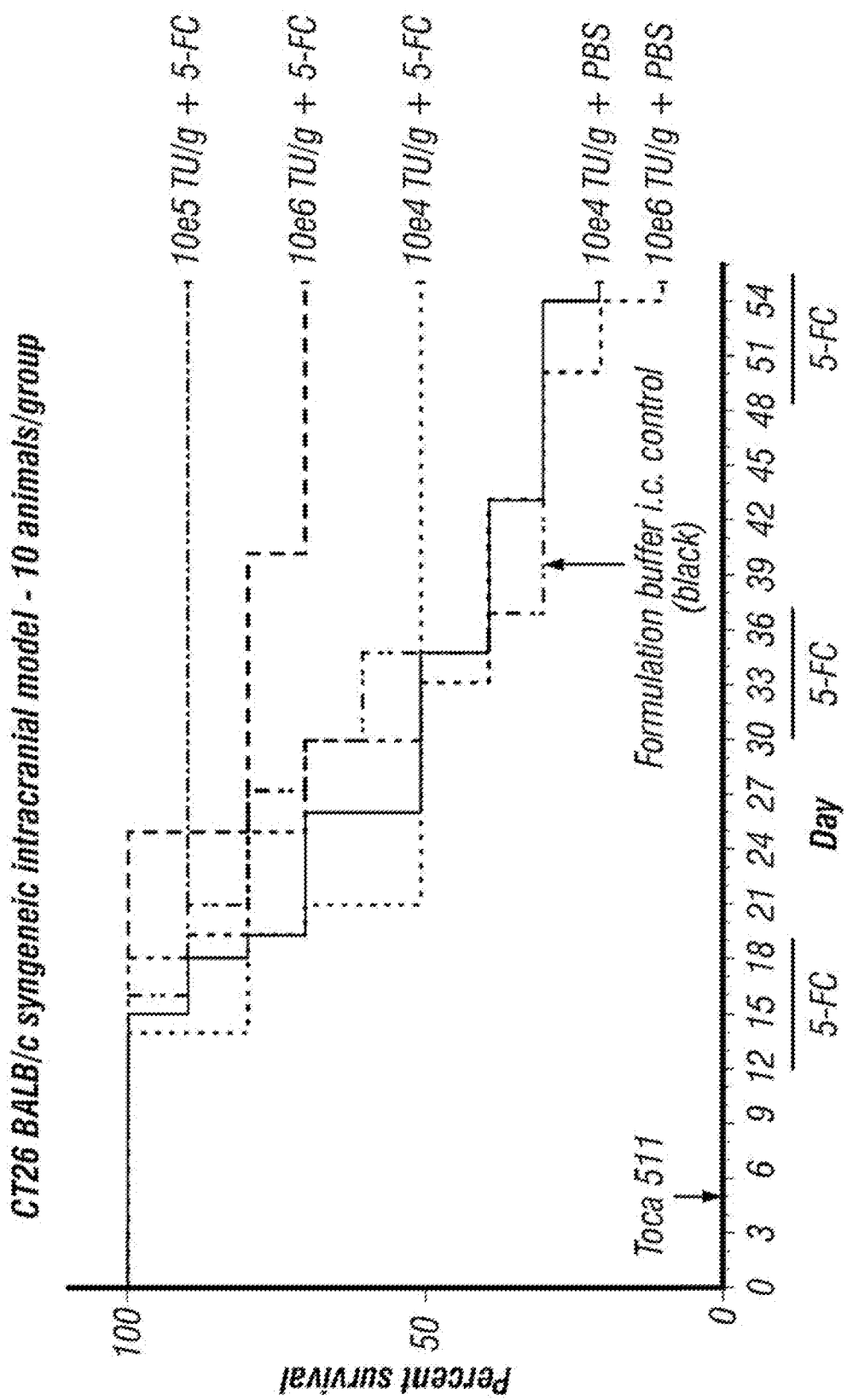
FIG. 9 shows dosing information and therapeutic effect in a syngeneic mouse model.

The TOCA 511 vector encodes a yeast cytosine deaminase (CD) gene. This gene sequence has been inserted downstream of an internal ribosome entry site (IRES) derived from the Encephalomyocarditis Virus (EMCV), which is inserted downstream of the viral env gene as shown in FIG. 5, below. The gene in the TOCA 511 vector is a modified yeast cytosine deaminase gene. The rationale for using a modified CD gene is to allow for more efficient in vivo conversion of the oral prodrug flucytosine (5-FC) to the active cytotoxic agent fluorouracil (5-FU).

The methods and compositions of the disclosure are applicable to other vector and recombinant retroviral vectors. The disclosure describes various modification and recombinant vectors that can be produced by the cell lines and methods of the disclosure.

The methods and cell lines of the disclosure include recombinant constructs comprising one or more of the nucleic acid sequences encoding a heterologous nucleic acid of interest (e.g., a cytosine deaminase such as the polynucleotides and polypeptides provided in SEQ ID NOs:1-13) a gamma Interferon gene or any of a number of therapeutic genes such as those disclosed in the published patent application WO2010036986. In one embodiment, the viral vector is a retroviral vector.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

In one embodiment, the vector is a viral vector. In a further embodiment, the viral vector is a replication competent retroviral vector capable of infecting only replicating mammalian cells. Retroviruses have been classified in various ways but the nomenclature has been standardized in the last decade (see ICTVdB—The Universal Virus Database, v 4 on the World Wide Web (www) at ncbi.nlm.nih.gov/ICTVdb/ICTVdB/ and the text book "Retroviruses," Eds. Coffin, Hughes and Varmus, Cold Spring Harbor Press 1997; the disclosure of which are incorporated herein by reference). The replication competent retroviral vector is derived from the Retroviridae family of viruses and can comprise a member of the Orthoretrovirinae sub-family, or more typically comprises a retrovirus from the gammaretrovirus genus. In one embodiment, a replication competent retroviral vector comprises an internal ribosomal entry site (IRES) 5' to a polynucleotide encoding a cytosine deaminase. In one embodiment, the polynucleotide encoding a cytosine deaminase is 3' to an env polynucleotide of a retroviral vector.

The disclosure provides modified retroviral vectors. The modified retroviral vectors can be derived from members of the retroviridae family. The classification of this family has changed several times over the last ten to fifteen years. Currently the Retroviridae family consists of two subfamilies: the Spumaretrovirinae-which has a single genus, the spumavirus (or foamy viruses) such as the human and simian foamy virus (HFV) and the Orthoretroviriniae subfamily which has 6 genus—betaretrovirus (e.g. MMTV), gammaretrovirus (e.g MLV), alpharetrovirus (e.g. ALV) deltaretrovirus (e.g. BLV and HTLV-1) lentivirus (e.g. HIV 1) and epsilon retrovirus (e.g. wall eye dermal sarcoma virus). These classifications are made on the basis of common molecular features such as the relative reading frames for gag, pol and env, the processing of the polyproteins, the individual tRNAS used for priming reverse transcription, and the nature of the LTR structures. The original method of classification of retroviruses was into groups A, B, C and D on the basis of particle morphology, as seen under the electron microscope during viral maturation. A-type particles represent the immature particles of the B- and D-type viruses seen in the cytoplasm of infected cells. These particles are not infectious. B-type particles bud as mature virion from the plasma membrane by the enveloping of intracytoplasmic A-type particles. At the membrane they possess a toroidal core of 75 nm, from which long glycoprotein spikes project. After budding, B-type particles contain an eccentrically located, electron-dense core. The betaretrovirus, Mouse mammary tumor virus (MMTV) has a B-type morphology, but betaretroviruses can also have a D-type structure. D-type particles resemble B-type particles in that they show as ring-like structures in the infected cell cytoplasm, which bud from the cell surface, but the virion incorporate short surface glycoprotein spikes. The electron-dense cores are also eccentrically located within the particles. Mason Pfizer monkey virus (MPMV), also a betaretrovirus, is the prototype D-type virus. No intracytoplasmic particles can be observed in cells infected by C-type viruses. Instead, mature particles bud directly from the cell surface via a crescent 'C'-shaped condensation which then closes on itself and is enclosed by the plasma membrane. Envelope glycoprotein spikes may be visible, along with a uniformly electron-dense core. Budding may occur from the surface plasma membrane or directly into intracellular vacuoles. Alpharetroviruses, gammaretroviruses, deltaretroviruses and epsilonretroviruses all have the C-type structural appearance.

Retroviruses are defined by the way in which they replicate their genetic material. During replication the RNA is converted into DNA. Following infection of the cell a double-stranded molecule of DNA is generated from the two molecules of RNA which are carried in the viral particle by the molecular process known as reverse transcription. The DNA form becomes covalently integrated in the host cell genome as a provirus, from which viral RNAs are expressed with the aid of cellular and/or viral factors. The expressed viral RNAs are packaged into particles and released as infectious virion.

The retrovirus particle is composed of two identical RNA molecules. Each wild-type genome has a positive sense, single-stranded RNA molecule, which is capped at the 5' end and polyadenylated at the 3' tail. The diploid virus particle contains the two RNA strands complexed with gag proteins, viral enzymes (pol gene products) and host tRNA molecules within a 'core' structure of gag proteins. Surrounding and protecting this capsid is a lipid bilayer, derived from host cell membranes and containing viral envelope (env) proteins. The env proteins bind to a cellular receptor for the virus and the particle typically enters the host cell via receptor-mediated endocytosis and/or membrane fusion.

After the outer envelope is shed, the viral RNA is copied into DNA by reverse transcription. This is catalyzed by the reverse transcriptase enzyme encoded by the pol region and uses the host cell tRNA packaged into the virion as a primer for DNA synthesis. In this way the RNA genome is converted into the more complex DNA genome.

The double-stranded linear DNA produced by reverse transcription may, or may not, have to be circularized in the nucleus. The provirus now has two identical repeats at either end, known as the long terminal repeats (LTR). The termini of the two LTR sequences produces the site recognized by a pol product—the integrase protein—which catalyzes integration, such that the provirus is always joined to host DNA two base pairs (bp) from the ends of the LTRs. A duplication of cellular sequences is seen at the ends of both LTRs, reminiscent of the integration pattern of transposable genetic elements. Integration is thought to occur essentially at random within the target cell genome. However, by modifying the long-terminal repeats it is possible to control the integration of a retroviral genome.

Transcription, RNA splicing and translation of the integrated viral DNA is mediated by host cell proteins. Variously spliced transcripts are generated. In the case of the human retroviruses HIV-1/2 and HTLV-I/II viral proteins are also used to regulate gene expression. The interplay between cellular and viral factors is a factor in the control of virus latency and the temporal sequence in which viral genes are expressed.

Retroviruses can be transmitted horizontally and vertically. Efficient infectious transmission of retroviruses requires the expression on the target cell of receptors which specifically recognize the viral envelope proteins, although viruses may use receptor-independent, nonspecific routes of entry at low efficiency. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

As mentioned above, the integrated DNA intermediate is referred to as a provirus. Prior gene therapy or gene delivery systems use methods and retroviruses that require transcription of the provirus and assembly into infectious virus while in the presence of an appropriate helper virus or in a cell line containing appropriate sequences enabling encapsidation without coincident production of a contaminating helper virus. As described below, a helper virus is not required for the production of the recombinant retrovirus of the disclosure, since the sequences for encapsidation are provided in the genome thus providing a replication competent retroviral vector for gene delivery or therapy.

The retroviral genome and the proviral DNA of the disclosure have at least three genes: the gag, the pol, and the env, these genes may be flanked by one or two long terminal (LTR) repeat, or in the provirus are flanked by two long terminal repeat (LTR) and sequences containing cis-acting sequences such as psi. The gag gene encodes the internal structural (matrix, capsid, and nucleocapsid) proteins; the pol gene encodes the RNA-directed DNA polymerase (reverse transcriptase), protease and integrase; and the env gene encodes viral envelope glycoproteins. The 5' and/or 3' LTRs serve to promote transcription and polyadenylation of the virion RNAs. The LTR contains all other cis-acting sequences necessary for viral replication. Lentiviruses have additional genes including vif, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virion) are missing from the viral genome, the result is a cis defect which prevents encapsidation of genomic viral RNA. This type of modified vector is what has typically been used in prior gene delivery systems (i.e., systems lacking elements which are required for encapsidation of the virion).

In a first embodiment, the disclosure provides a recombinant retrovirus capable of infecting a non-dividing cell, a dividing cell, or a cell having a cell proliferative disorder. The recombinant replication competent retrovirus of the disclosure comprises a polynucleotide sequence encoding a viral GAG, a viral POL, a viral ENV, and a heterologous polynucleotide that is expressed after the viral vector infects a target cell, encapsulated within a virion.

In one embodiment the heterologous nucleic acid sequence is preceded by a promoter and is operably linked to the promoter In another embodiment the heterologous nucleic acid sequence is preceded by an internal ribosome entry site (IRES) and is operably linked to the IRES.

An internal ribosome entry sites ("IRES") refers to a segment of nucleic acid that promotes the entry or retention of a ribosome during translation of a coding sequence usually 3' to the IRES. In some embodiments the IRES may comprise a splice acceptor/donor site, however, preferred IRESs lack a splice acceptor/donor site. Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that, in particular, of picornaviruses such as the poliomyelitis virus (Pelletier et al., 1988, Mol. Cell. Biol., 8, 1103-1112) and the EMCV virus (encephalomyocarditis virus (Jang et al., J. Virol., 1988, 62, 2636-2643). The disclosure provides the use of an IRES in the context of a replication-competent retroviral vector.

Depending upon the intended use of the retroviral vector of the disclosure any number of heterologous polynucleotide or nucleic acid sequences may be inserted into the retroviral vector. Some examples are given in WO2010/036986. For example, for in vitro studies commonly used marker genes or reporter genes may be used, including, antibiotic resistance and fluorescent molecules (e.g., GFP). Additional polynucleotide sequences encoding any desired polypeptide sequence may also be inserted into the vector of the disclosure. Where in vivo delivery of a heterologous nucleic acid sequence is sought both therapeutic and non-therapeutic sequences may be used. For example, the heterologous sequence can encode a therapeutic molecule including antisense molecules or ribozymes directed to a particular gene associated with a cell proliferative disorder, the heterologous sequence can be a suicide gene (e.g., HSV-tk or PNP or cytosine deaminase), an small interfering RNA or microRNA, a growth factor or a therapeutic protein (e.g., Factor IX). Other therapeutic proteins applicable to the disclosure are easily identified in the art.

In one embodiment, the heterologous polynucleotide within the vector comprises a cytosine deaminase that has been optimized for expression in a human cell. In a further embodiment, the cytosine deaminase comprises a sequence that has been human codon optimized and comprises mutations that increase the cytosine deaminase's stability (e.g., reduced degradation or increased thermo-stability) compared to a wild-type cytosine deaminase. In yet another embodiment, the heterologous polynucleotide encodes a fusion construct comprising a cytosine deaminase (either human codon optimized or non-optimized, either mutated or non-mutated) operably linked to a polynucleotide encoding a polypeptide having UPRT or OPRT activity. In another embodiment, the heterologous polynucleotide comprises a CD polynucleotide of the disclosure (e.g., SEQ ID NO:3, 5, 11, 13, 15, or 17).

In another embodiment, replication competent retroviral vector can comprise a heterologus polynucleotide encoding a polypeptide comprising a cytosine deaminase (as described herein) and may further comprise a polynucleotide comprising a miRNA or siRNA molecule linked to a cell-type or tissue specific promoter.

As used herein, the term "RNA interference" (RNAi) refers to the process of sequence-specific post-transcriptional gene silencing mediated by short interfering nucleic acids (siRNAs). The term "agent capable of mediating RNA interference" refers to siRNAs as well as DNA and RNA vectors that encode siRNAs when transcribed within a cell. As used herein, the term "siNA" refers to short interfering nucleic acid. The term is meant to encompass any nucleic acid molecules that are capable of mediating sequence specific RNA interference, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others.

Suitable range for designing stem lengths of a hairpin duplex, includes stem lengths of 20-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides, and 600-700 nucleotides. Suitable range for designing loop lengths of a hairpin duplex, includes loop lengths of 4-25 nucleotides, 25-50 nucleotides, or longer if the stem length of the hair duplex is substantial. In certain context, hairpin structures with duplexed regions that are longer than 21 nucleotides may promote effective siRNA-directed silencing, regardless of the loop sequence and length.

The replicating retroviruses of the disclosure can also be used to modify disease by expressing engineered siRNA or miRNA (Dennis, Nature, 418: 122 2002) that switches off or lowers expression of key genes that govern the proliferation or survival of diseased cells including tumor cells. Such targets include genes like Rad 51 a central enzyme in DNA repair, and without which cell growth is drastically restricted. Other targets include many of the signaling pathway molecules that control cell growth (Marquez & McCaffrey Hum Gene Ther. 19:27 2008). The vectors will replicate through the tumor and before growth inhibition occurs the virus first integrates into the host genome and continues to make virus after growth of that cell is inhibited. Methods for selecting functional miRNA or siRNA sequences are known in the art. Key feature in general in designing effective siRNA or miRNA sequences is usually avoiding "off-target" effects. However for the use of replicating vectors that are highly specific to tumor cells such as those of the disclosure, these side effects are not very important, as the cells are expected to eventually die. Vector of this disclosure would be made using cells from other species for which the corresponding protein is not significantly targeted. Such cells include dog cell lines or chicken cell line. Alternatively the virus is made by transient transfection on human 293 derived cells or other cell line that allows efficient transient transfection. For this use the virus does not need to express an IRES, and the siRNA or miRNA sequence can simply be inserted at a convenient site on the viral genome. This site includes the region downstream of the envelope and upstream of the 3'LTR of the replicating retrovirus. Alternatively polIII transcription units can be inserted in the viral genome with the appropriate siRNA or miRNA's, preferably downstream of the 3' envelope gene. Several different siRNA or miRNA sequences can be inserted to ensure efficient down regulation of the target gene or down regulation of more than one gene. Suitable sequences and targets can be obtained from sources known to those skilled in the art. For example:

The MIT/ICBP siRNA Database http: (//)web.mit.edu/sirna/—"The MIT [Massachusetts Institute of Technology]/ICBP [Integrative Cancer Biology Program] siRNA Database is a university-wide effort to catalog these experimentally validated reagents and make that information available to other researchers, both within and outside the MIT community. (Massachusetts Institute of Technology).

RNAi Central—http:(//)katahdin.cshl.org:9331/RNAi_web/scripts/main2.pl RNAi resources, including siRNA and shRNA design tools. (Hannon Lab, Cold Spring Harbor Laboratory)

The RNAi Web—http:(//)www.rnaiweb.com/ General resource.

siDIRECT—http:(//)genomics.jp/sidirect/ Online target-specific siRNA design program for mammalian RNA interference. (University of Tokyo, Japan).

siRNA Database—A comprehensive siRNA database that contains siRNA targets against all known mRNA sequences throughout a variety of organisms. (Part of the Protein Lounge systems biology Web site)

siRNA Database and Resources for RNA Interference Studies http:(//)www.rnainterference.org/ siRNA Selector—http:(//)bioinfo.wistar.upenn.edu/siRNA/siRNA.htm. A set of rules was used for evaluating siRNA functionality based on thermodynamics parameters (Khvorova et al., 2003, Schwarz et al., 2003) and sequence-related determinants developed by Dharmacon (Reynolds et al., 2004). Specificity is determined using BLAST against UniGene databases. (Wistar Institute)

siRNA Target Finder http:(//)www.ambion.com/techlib/misc/siRNA_finder.html (Ambion)

The replicating retroviruses of the disclosure can also express targets for naturally occurring siRNA's that are restricted in expression to particular cell types so that replication of the vector is significantly inhibited in those cell types. For anti-tumor purposes some normal cells in the body that are naturally replicating at some level are hematopoietic cells, cells of the lining of the gut, and some endothelial cells. These are then potential sites where virus that is in the circulation could productively infect. In general this would be undesirable. Any stray infection of cells such as these can be inhibited by including a target for naturally occurring siRNA's or combination of siRNA's in these cell types. Some feasibility of using siRNA targets to suppress immune responses has already been shown. (Brown et al. Nat Biotechnol. 2007 25:1457-67). These targets are small RNA sequences with an homologous match to the siRNA sequences that are naturally occurring. These sequences can be inserted in any convenient site in the vectors of the current invention without, in general significant deleterious consequence for vector viability, other than in a cell of the type desired. Vectors can be made and used as previously described. The siRNA target can be inserted 3' to the transgene but before the 3'LTR or upstream of the IRES but after the 3' end of the envelope. In general the target would not be inserted into protein coding sequences In yet further embodiments, the heterologous polynucleotide may comprise a cytokine such as an interleukin, interferon gamma or the like.

Generally, the recombinant virus of the disclosure is capable of transferring a nucleic acid sequence into a target cell.

The term "nucleic acid regulatory domain" refers collectively to promoter sequences (e.g., pol II promoter sequences), polyadenylation signals, transcription termination sequences, upstream regulatory domains, origins of replication, enhancers and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter as described above.

The heterologous nucleic acid sequence is typically under control of either the viral LTR promoter-enhancer signals or an internal promoter, and retained signals within the retroviral LTR can still bring about efficient integration of the vector into the host cell genome. Accordingly, the recombinant retroviral vectors of the disclosure, the desired sequences, genes and/or gene fragments can be inserted at several sites and under different regulatory sequences. For example, a site for insertion can be the viral enhancer/promoter proximal site (i.e., 5' LTR-driven gene locus). Alternatively, the desired sequences can be inserted into a regulatory sequence distal site (e.g., the IRES sequence 3' to the env gene) or where two or more heterologous sequences are present one heterologous sequence may be under the control of a first regulatory region and a second heterologous sequence under the control of a second regulatory region. Other distal sites include viral promoter sequences, where the expression of the desired sequence or sequences is through splicing of the promoter proximal cistron, an internal heterologous promoter as SV40 or CMV, or an internal ribosome entry site (IRES) can be used.

In one embodiment, the retroviral genome of the disclosure contains an IRES comprising a cloning site for insertion of a desired polynucleotide sequence. In one embodiment, the IRES is located 3' to the env gene in the retroviral vector, but 5' to the desired heterologous nucleic acid. Accordingly, a heterologous polynucleotide sequence encoding a desired polypeptide may be operably linked to the IRES.

In another embodiment a targeting polynucleotide sequence is included as part of the recombinant retroviral vector of the disclosure. The targeting polynucleotide sequence is a targeting ligand (e.g., peptide hormones such as heregulin, a single-chain antibodies, a receptor or a ligand for a receptor), a tissue-specific or cell-type specific regulatory element (e.g., a tissue-specific or cell-type specific promoter or enhancer), or a combination of a targeting ligand and a tissue-specific/cell-type specific regulatory element. Preferably, the targeting ligand is operably linked to the env protein of the retrovirus, creating a chimeric retroviral env protein. The viral GAG, viral POL and viral ENV proteins can be derived from any suitable retrovirus (e.g., MLV or lentivirus-derived). In another embodiment, the viral ENV protein is non-retrovirus-derived (e.g., alphavirus, CMV or VSV).

The recombinant retrovirus of the disclosure is therefore genetically modified in such a way that the virus is targeted to a particular cell type (e.g., smooth muscle cells, hepatic cells, renal cells, fibroblasts, keratinocytes, mesenchymal stem cells, bone marrow cells, chondrocyte, epithelial cells, intestinal cells, neoplastic cells, glioma cells, neuronal cells and others known in the art) such that the nucleic acid genome is delivered to a target non-dividing, a target dividing cell, or a target cell having a cell proliferative disorder. Targeting can be achieved in two ways. The first way directs the retrovirus to a target cell by binding to cells having a molecule on the external surface of the cell. This method of targeting the retrovirus utilizes expression of a targeting ligand on the coat of the retrovirus to assist in targeting the virus to cells or tissues that have a receptor or binding molecule which interacts with the targeting ligand on the surface of the retrovirus. After infection of a cell by the virus, the virus injects its nucleic acid into the cell and the retrovirus genetic material can integrate into the host cell genome. The second method for targeting uses cell- or tissue-specific regulatory elements to promote expression and transcription of the viral genome in a targeted cell which actively utilizes the regulatory elements, as described more fully below. The transferred retrovirus genetic material is then transcribed and translated into proteins within the host cell. The targeting regulatory element is typically linked to the 5' and/or 3' LTR, creating a chimeric LTR.

By inserting a heterologous nucleic acid sequence of interest into the viral vector of the disclosure, along with another gene which encodes, for example, the ligand for a receptor on a specific target cell, the vector is now target specific. Viral vectors can be made target specific by attaching, for example, a sugar, a glycolipid, or a protein. Targeting can be accomplished by using an antibody to target the viral vector. Those of skill in the art will know of, or can readily ascertain, specific polynucleotide sequences which can be inserted into the viral genome or proteins which can be attached to a viral envelope to allow target specific delivery of the viral vector containing the nucleic acid sequence of interest.

Thus, the disclosure includes, in one embodiment, a chimeric env protein comprising a retroviral env protein operably linked to a targeting polypeptide. The targeting polypeptide can be a cell specific receptor molecule, a ligand for a cell specific receptor, an antibody or antibody fragment to a cell specific antigenic epitope or any other ligand easily identified in the art which is capable of binding or interacting with a target cell. Examples of targeting polypeptides or molecules include bivalent antibodies using biotin-streptavidin as linkers (Etienne-Julan et al., J. Of General Virol., 73, 3251-3255 (1992); Roux et al., Proc. Natl. Acad. Sci USA 86, 9079-9083 (1989)), recombinant virus containing in its envelope a sequence encoding a single-chain antibody variable region against a hapten (Russell et al., Nucleic Acids Research, 21, 1081-1085 (1993)), cloning of peptide hormone ligands into the retrovirus envelope (Kasahara et al., Science, 266, 1373-1376 (1994)), chimeric EPO/env constructs (Kasahara et al., 1994), single-chain antibody against the low density lipoprotein (LDL) receptor in the ecotropic MLV envelope, resulting in specific infection of HeLa cells expressing LDL receptor (Somia et al., Proc. Natl. Acad. Sci USA, 92, 7570-7574 (1995)), similarly the host range of ALV can be altered by incorporation of an integrin ligand, enabling the virus to now cross species to specifically infect rat glioblastoma cells (Valsesia-Wittmann et al., J. Virol. 68, 4609-4619 (1994)), and Dornberg and co-workers (Chu and Dornburg, J. Virol 69, 2659-2663 (1995)) have reported tissue-specific targeting of spleen necrosis virus (SNV), an avian retrovirus, using envelopes containing single-chain antibodies directed against tumor markers.

The disclosure provides a method of producing a recombinant retrovirus capable of infecting a target cell comprising transfecting a suitable host cell with the following: a vector comprising a polynucleotide sequence encoding a viral gag, a viral pol and a viral env, wherein the vector contains a cloning site for introduction of a heterologous gene, operably linked to a regulatory nucleic acid sequence, and recovering the recombinant virus.

The retrovirus and methods of the disclosure provide a replication competent retrovirus that does not require helper virus or additional nucleic acid sequence or proteins in order to propagate and produce virion. For example, the nucleic acid sequences of the retrovirus of the disclosure encode, for example, a group specific antigen and reverse transcriptase, (and integrase and protease-enzymes necessary for maturation and reverse transcription), respectively, as discussed above. The viral gag and pol can be derived from a lentivirus, such as HIV or a gammaretrovirus such as MoMLV. In addition, the nucleic acid genome of the retrovirus of the disclosure includes a sequence encoding a viral envelope (ENV) protein. The env gene can be derived from any retroviruses. The env may be an amphotropic envelope protein which allows transduction of cells of human and other species, an ecotropic envelope protein, which is able to transduce only mouse and rat cells, a xenotropic envelope, a GALV envelope, an RD114 envelope, an FeLV envelope or other retroviral envelope. The envelope may also be an envelope from a heterologous source such as an alphavirus, CMV or VSV. Further, it may be desirable to target the recombinant virus by linkage of the envelope protein with an antibody or a particular ligand for targeting to a receptor of a particular cell-type. As mentioned above, retroviral vectors can be made target specific by inserting, for example, a glycolipid, or a protein. Targeting is often accomplished by using an antibody to target the retroviral vector to an antigen on a particular cell-type (e.g., a cell type found in a certain tissue, or a cancer cell type). Those of skill in the art will know of, or can readily ascertain without undue experimentation, specific methods to achieve delivery of a retroviral vector to a specific target. In one embodiment, the env gene is derived from a non-retrovirus (e.g., alphavirus, CMV or VSV). Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G), cytomegalovirus envelope (CMV), or influenza virus hemagglutinin (HA) can also be used.

In one embodiment, the retroviral genome is derived from a gammaretrovirus, and more particularly a mammalian gammaretrovirus. By "derived" is meant that the parent polynucleotide sequence is an wild-type gammaretrocvirus that has been modified by insertion or removal of naturally occurring sequences (e.g., insertion of an IRES, insertion of a heterologous polynucleotide encoding a polypeptide or inhibitory nucleic acid of interest, shuffling of a more effective promoter from a different retrovirus or virus in place of the wild-type promoter and the like).

Unlike recombinant retroviruses produced by standard methods in the art that are defective and require assistance in order to produce infectious vector particles, the disclosure provides a retrovirus that is replication-competent.

In another embodiment, the disclosure provides retroviral vectors that are targeted using regulatory sequences. Cell- or tissue-specific regulatory sequences (e.g., promoters) can be utilized to target expression of gene sequences in specific cell populations. Suitable mammalian and viral promoters for the disclosure are described elsewhere herein. Accordingly, in one embodiment, the disclosure provides a retrovirus having tissue-specific promoter elements at the 5' end of the retroviral genome. Preferably, the tissue-specific regulatory elements/sequences are in the U3 region of the LTR of the retroviral genome, including for example cell- or tissue-specific promoters and enhancers to neoplastic cells (e.g., tumor cell-specific enhancers and promoters), and inducible promoters (e.g., tetracycline).

Transcription control sequences of the disclosure can also include naturally occurring transcription control sequences naturally associated with a gene encoding a superantigen, a cytokine or a chemokine.

In some circumstances, it may be desirable to regulate expression. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV can be used. Other viral promoters that can be used include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific or selective promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Other promoters/regulatory domains that can be used are set forth in Table 1.

In certain indications, it may be desirable to activate transcription at specific times after administration of the gene therapy vector. This may be done with such promoters as those that are hormone or cytokine regulatable. For example in therapeutic applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones may be used. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-i acid glycoprotein (Prowse and Baumann, 1988), alpha-1 antitypsin, lipoprotein lipase (Zechner et al., 1988), angiotensinogen (Ron et al., 1990), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin. Tumor specific promoters such as osteocalcin, hypoxia-responsive element (HRE), MAGE-4, CEA, alpha-fetoprotein, GRP78/BiP and tyrosinase may also be used to regulate gene expression in tumor cells.

In addition, this list of promoters should not be construed to be exhaustive or limiting, those of skill in the art will know of other promoters that may be used in conjunction with the promoters and methods disclosed herein.

TABLE 1

TISSUE SPECIFIC PROMOTERS

| Tissue | Promoter |
| --- | --- |
| Pancreas | Insulin Elastin Amylase pdr-1 pdx-1 glucokinase |
| Liver | Albumin PEPCK HBV enhancer α fetoprotein apolipoprotein C α-1 antitrypsin vitellogenin, NF-AB Transthyretin |
| Skeletal muscle | Myosin H chain Muscle creatine kinase Dystrophin Calpain p94 Skeletal alpha-actin fast troponin 1 |
| Skin | Keratin K6 Keratin K1 |
| Lung | CFTR Human cytokeratin 18 (K18) Pulmonary surfactant proteins A, B and C CC-10 P1 |
| Smooth muscle | sm22 α SM-alpha-actin |
| Endothelium | Endothelin-1 E-selectin von Willebrand factor TIE (Korhonen et al., 1995) KDR/flk-1 Melanocytes Tyrosinase |
| Adipose tissue | Lipoprotein lipase (Zechner et al., 1988) Adipsin (Spiegelman et al., 1989) acetyl-CoA carboxylase (Pape and Kim, 1989) glycerophosphate dehydrogenase (Dani et al., 1989) adipocyte P2 (Hunt et al., 1986) |
| Blood | β-globin |
| Glioma | GFAP, nestin, Msi 1 (J. Huang et al. Acta Biochim Biophys Sin 2010, 42: 274-280) |

"Tissue-specific regulatory elements" are regulatory elements (e.g., promoters) that are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the disclosure typically has a selectivity ratio of greater than about 5. Preferably, the selectivity ratio is greater than about 15.

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the disclosure. For example, promoters that are active in a variety of central nervous system (CNS) neurons may be therapeutically useful in protecting against damage due to stroke, which may effect any of a number of different regions of the brain. Accordingly, the tissue-specific regulatory elements used in the disclosure, have applicability to regulation of the heterologous proteins as well as a applicability as a targeting polynucleotide sequence in the present retroviral vectors.

The retroviral vectors and CD polynucleotide and polypeptide of the disclosure can be used to treat a wide range of disease and disorders including a number of cell proliferative diseases and disorders (see, e.g., U.S. Pat. Nos. 4,405,712 and 4,650,764; Friedmann, 1989, Science, 244: 1275-1281; Mulligan, 1993, Science, 260:926-932, R. Crystal, 1995, Science 270:404-410, each of which are incorporated herein by reference in their entirety, see also, The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

The phrase "non-dividing" cell refers to a cell that does not go through mitosis. Non-dividing cells may be blocked at any point in the cell cycle, (e.g., $G_0/G_1$, $G_{1/S}$, $G_{2/M}$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector is capable of infecting many non-dividing cells, regardless of the mechanism used to block cell division or the point in the cell cycle at which the cell is blocked. Examples of pre-existing non-dividing cells in the body include neuronal, muscle, liver, skin, heart, lung, and bone marrow cells, and their derivatives. For dividing cells gamma-retroviral vectors can be used, as they are only capable of infecting cells that are dividing.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous call cancer, malignant melanoma, sinonasal undifferentiated carcinoma (SNUC), brain (including glioblastomas) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer, skin cancer and ovarian cancer.

The disclosure also provides gene therapy for the treatment of cell proliferative disorders. Such therapy would achieve its therapeutic effect by introduction of an appropriate therapeutic polynucleotide sequence (e.g., antisense, ribozymes, suicide genes, siRNA), into cells of subject having the proliferative disorder. Delivery of polynucleotide constructs can be achieved using the recombinant retroviral vector of the disclosure, particularly if it is based on MLV, which will is capable of infecting only dividing cells, and which continues to be made in infected cells, even after the cells stop dividing.

In addition, the therapeutic methods (e.g., the gene therapy or gene delivery methods) as described herein can be performed in vivo or ex vivo. It may be preferable to remove the majority of a tumor prior to gene therapy, for example surgically or by radiation. Surgery or radiation can also be used after gene therapy. In some aspects, the retroviral therapy may be preceded or followed by chemotherapy.

Thus, the disclosure provides a recombinant retrovirus capable of infecting a non-dividing cell, a dividing cell or a neoplastic cell, therein the recombinant retrovirus comprises a viral GAG; a viral POL; a viral ENV; a heterologous nucleic acid operably linked to an IRES or an internal promoter; and cis-acting nucleic acid sequences necessary for packaging, reverse transcription and integration. The recombinant retrovirus can be a lentivirus, such as HIV, or can be an gammaretrovirus. As described above for the method of producing a recombinant retrovirus, the recombinant retrovirus of the disclosure may further include at least one of VPR, VIF, NEF, VPX, TAT, REV, and VPU protein. While not wanting to be bound by a particular theory, it is believed that one or more of these genes/protein products are important for increasing the viral titer of the recombinant retrovirus produced (e.g., NEF) or may be advantageous for infection and packaging of virion in cells with high levels of viral restriction elements (e.g. VIF for cells with active APOBEC3G or equivalent).

The disclosure also provides a method of nucleic acid transfer to a target cell to provide expression of a particular nucleic acid (e.g., a heterologous sequence). Therefore, in another embodiment, the disclosure provides a method for introduction and expression of a heterologous nucleic acid in a target cell comprising infecting the target cell with the recombinant virus of the disclosure and expressing the heterologous nucleic acid in the target cell. As mentioned above, the target cell can be any cell type including dividing, non-dividing, neoplastic, immortalized, modified and other cell types recognized by those of skill in the art, so long as they are capable of infection by a retrovirus.

It may be desirable to modulate the expression of a gene in a cell by the introduction of a nucleic acid sequence (e.g., the heterologous nucleic acid sequence) by the method of the disclosure, wherein the nucleic acid sequence give rise, for example, to an antisense or ribozyme molecule. The term "modulate" envisions the suppression of expression of a gene when it is over-expressed, or augmentation of expression when it is under-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, Anal. Biochem., 172:289, 1988).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism, and other diseases. Of particular interest are the blocking of genes associated with cell-proliferative disorders. Antisense nucleic acids are also useful for the inhibition of expression of proteins associated with toxicity.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., Antisense Res. and Dev., 1(3):227, 1991; Helene, C., Anticancer Drug Design, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

It may be desirable to transfer a nucleic acid encoding a biological response modifier (e.g., a cytokine). Included in this category are immunopotentiating agents including nucleic acids encoding a number of the cytokines classified as "interleukins". These include, for example, interleukins 1 through 15. Also included in this category, although not necessarily working according to the same mechanisms, are interferons, and in particular gamma interferon, tumor necrosis factor (TNF) and granulocyte-macrophage-colony stimulating factor (GM-CSF). Other polypeptides include, for example, angiogenic factors and anti-angiogenic factors. It may be desirable to deliver such nucleic acids to bone marrow cells or macrophages to treat enzymatic deficiencies or immune defects. Nucleic acids encoding growth factors, toxic peptides, ligands, receptors, or other physiologically important proteins can also be introduced into specific target cells.

For example, HER2 (see, e.g., SEQ ID NO:23 and 24), a member of the EGF receptor family, is the target for binding of the drug trastuzumab (Herceptin™, Genentech). Trastuzumab is a mediator of antibody-dependent cellular cytotoxicity (ADCC). Activity is preferentially targeted to HER2-expressing cells with 2+ and 3+ levels of overexpression by immunohistochemistry rather than 1+ and non-expressing cells (Herceptin prescribing information, Crommelin 2002). Enhancement of expression of HER2 by introduction of vector expressing HER2 or truncated HER2 (expressing only the extracellular and transmembrane domains) in HER2 low tumors may facilitate optimal triggering of ADCC and overcome the rapidly developing resistance to HER2 that is observed in clinical use.

The substitution of yCD2 for the intracellular domain of HER2 allows for cell surface expression of HER2 and cytosolic localization of yCD2. The HER2 extracellular domain (ECD) and transmembrane domain (TM) (approximately 2026 bp from about position 175 to 2200) can be amplified by PCR (Yamamoto et al., Nature 319:230-234, 1986; Chen et al., Canc. Res., 58:1965-1971, 1998) or chemically synthesized (BioBasic Inc., Markham, Ontario, Canada) and inserted between the IRES and yCD2 gene in the vector pAC3-yCD2 SEQ ID NO: 19. Althernatively, the yCD gene can be excised and replaced with a polynucleotide encoding a HER2 polypeptide or fragment thereof. A further truncated HER2 with only the Herceptin binding domain IV of the ECD and TM domains (approximately 290 bp from position 1910 to 2200) can be amplified or chemically synthesized and used as above (Landgraf 2007; Garrett et al., J. of Immunol., 178:7120-7131, 2007). A further modification of this truncated form with the native signal peptide (approximately 69 bp from position 175-237) fused to domain IV and the TM can be chemically synthesized and used as above. The resulting viruses can be used to treat a cell proliferative disorder in a subject in combination with trastuzumab or trastuzumab and 5-FC.

Alternatively, HER2 and the modifications described above can be expressed in a separate vector containing a different ENV gene or other appropriate surface protein. This vector can be replication competent (Logg et al. J. Mol Biol. 369:1214 2007) or non replicative "first generation" retroviral vector that encodes the envelope and the gene of interest (Emi et al. J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses (Palu 2000, Baum et al., Mol. Therapy, 13(6):1050-1063, 2006). For example, a polynucleotide can comprise a sequence wherein the GAG and POL and yCD2 genes of SEQ ID NO: 19 are deleted, the ENV corresponds to a xenotropic ENV domain of NZB MLV or VSV-g, and the IRES or a promoter such as RSV is operatively linked directly to HER2, HER2 ECDTM, HER2 ECDIVTM, or HER2 SECDIVTM.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above results in production of progeny virions capable of encoding yCD2 and HER2 (or variant) in infected cells. The resulting viruses can be used to treat a cell proliferative disorder in a subject in combination with trastuzumab or trastuzumab and 5-FC.

Another aspect of the development of resistance to trastuzumab relates to the interference with intracellular signaling required for the activity of trastuzumab. Resistant cells show loss of PTEN and lower expression of p27kip1 [Fujita, Brit J. Cancer, 94:247, 2006; Lu et al., Journal of the National Cancer Institute, 93(24): 1852-1857, 2001; Kute et al., Cytometry Part A 57A:86-93, 2004).

For example, a polynucleotide encoding PTEN (SEQ ID NO:25) can be chemically synthesized (BioBasic Inc., Markham, Canada) and operably inserted directly after the yCD2 gene in the vector pAC3-yCD2 SEQ ID NO: 19 or 22, or with a linker sequence as previously described, or as a replacement for yCD2. In a further example, the PTEN encoding polynucleotide can be synthesized as above and inserted between the IRES and yCD2 sequences or with a linker as previously described.

Alternatively, PTEN can be expressed in a separate vector containing a different ENV gene or other appropriate surface protein. This vector can be replication competent (Logg et al. J. Mol Biol. 369:1214 2007) or non replicative "first generation" retroviral vector that encodes the envelope and the gene of interest (Emi et al., J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses (Palu, Rev Med Virol. 2000, Baum, Mol. Ther. 13(6):1050-1063, 2006). For example, a polynucleotide can comprise a sequence wherein the gag and pol and yCD2 genes of SEQ ID NO: 19 are deleted, the ENV corresponds to a xenotropic ENV domain of NZB MLV or VSV-g, and the IRES or a promoter such as RSV is operatively linked directly to PTEN.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above results in production of progeny virions capable of encoding yCD2 and PTEN (or variant) or PTEN alone in infected cells. The resulting viruses can be used to treat a cell proliferative disorder in a subject in combination with trastuzumab or trastuzumab and 5-FC.

Similarly, a polynucleotide encoding p27kip1 (SEQ ID NO:27 and 28) can be chemically synthesized (BioBasic Inc., Markham, Canada) and operably inserted directly after the yCD2 gene in the vector pAC3-yCD2 SEQ ID NO: 19 or with a linker sequence. In a further example, the p27kip1 encoding polynucleotide can be synthesized as above and inserted between the IRES and yCD2 sequences or with a linker as previously described or in place of the yCD2 gene.

Alternatively, p27kip1 can be expressed in a separate vector containing a different env gene or other appropriate surface protein. This vector can be replication competent or non-replicative "first generation" retroviral vector that encodes the envelope and the gene of interest (Emi et al. J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example, ENV sequences from the NZB strain of MLV and glycoproteins from MCF, VSV, GALV and other viruses (Palu 2000, Baum 2006, supra). For example, a polynucleotide can comprise a sequence wherein the gag and pol and yCD2 genes of SEQ ID NO: 19 are deleted, the ENV corresponds to a xenotropic ENV domain of NZB MLV or VSV-g, and the IRES or a promoter such as RSV is operatively linked directly to p27kip1.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above from both SEQ ID NO: 19 and TT results in production of progeny virions capable of encoding yCD2 and p27kip1 (or variant) in infected cells. The resulting viruses can be used to treat a cell proliferative disorder in a subject in combination with trastuzumab or trastuzumab and 5-FC.

In another example, CD20 is the target for binding of the drug rituximab (Rituxan™, Genentech). Rituximab is a mediator of complement-dependent cytotoxicity (CDC) and ADCC. Cells with higher mean fluorescence intensity by flow cytometry show enhanced sensitivity to rituximab (van Meerten et al., Clin Cancer Res 2006; 12(13):4027-4035, 2006). Enhancement of expression of CD20 by introduction of vector expressing CD20 in CD20 low B cells may facilitate optimal triggering of ADCC.

For example, a polynucleotide encoding CD20 (SEQ ID NO:29 and 30) can be chemically synthesized (BioBasic Inc., Markham, Canada) and operably inserted directly after the yCD2 gene in the vector pAC3-yCD2(-2) SEQ ID NO: 19 or 22 with a linker sequence as previously described, or as a replacement for the yCD2 gene. In a further example, the CD20 encoding polynucleotide can be synthesized as above and inserted between the IRES and yCD2 sequences or with a linker as previously described. As a further alternative the CD20 sequence can be inserted into the pAC3-yCD2 vector after excision of the CD gene by Psi1 and Not1 digestion.

In still a further example, a polynucleotide encoding CD20 (SEQ ID NO:29 and 30) can be chemically synthesized (BioBasic Inc., Markham, Canada) and inserted into a vector containing a non amphotropic env gene or other appropriate surface protein (Tedder et al., PNAS, 85:208-212, 1988). Alternate ENV and glycoproteins include xenotropic and polytropic ENV and glycoproteins capable of infecting human cells, for example ENV sequences from the NZB strain of MLV and glycoproteins from MCF, VSV, GALV and other viruses [Palu 2000, Baum 2006]. For example, a polynucleotide can comprise a sequence wherein the gag and pol and yCD2 genes of SEQ ID NO: 19 are deleted, the ENV corresponds to a xenotropic ENV domain of NZB MLV or VSV-g, and the IRES or a promoter such as RSV is operatively linked directly to CD20.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above from both SEQ ID NO: 19 or 22 results in production of progeny virions capable of encoding yCD2 and CD20 in infected cells. The resulting viruses can be used to treat a cell proliferative disorder in a subject in combination with Rituxan and/or 5-FC. Similarly, infection of a tumor with a vector encoding only the CD20 marker can make the tumor treatable by the use of Rituxan.

Levels of the enzymes and cofactors involved in pyrimidine anabolism can be limiting. OPRT, thymidine kinase (TK), Uridine monophosphate kinase, and pyrimidine nucleoside phosphorylase expression is low in 5-FU resistant cancer cells compared to sensitive lines (Wang et al., Cancer Res., 64:8167-8176, 2004). Large population analyses show correlation of enzyme levels with disease outcome (Fukui et al., Int'l. J. OF Mol. Med., 22:709-716, 2008). Coexpression of CD and other pyrimidine anabolism enzymes (PAE) can be exploited to increase the activity and therefore therapeutic index of fluoropyrimidine drugs.

To further increase the genetic stability (see, e.g., FIG. 5) of yCD2/PAE containing vectors, the enzyme encoding gene can be chemically synthesized with random mutations throughout the sequence. These mutations can be essentially random or can consist of only mutations at the wobble position for each amino acids. The library of mutated sequences is inserted downstream of the yCD2 gene as was previously described for SEQ ID NO: 11 and 13 to create a library of plasmids that can then be used to generate a library of infectious particles by transient transfection of 293T cells or equivalent. Sensitive cells can be infected with retrovirus encoding the fusion polypeptide and subjected to selection with appropriate chemicals. For example, randomly mutagenized Herpes Thymidine Kinase (TK) is chemically synthesized (Bio Basic Inc, Markham, Canada). The synthetic sequence is inserted 3' of the yCD2 sequence in SEQ ID NO:19, or by itself in the pAC3-yCD2 vector back bones after excision of the CD2 gene. The retroviral vector mixture is packaged as previously described. Mouse fibroblast LMTK– cells are infected with vector and selected for TK activity in HAT media (Hiller et al., Mol. Cell Biol. 8(8): 3298-3302, 1988). Serial passage of supernatants of resistant cells to fresh LMTK– cells again selected in HAT media results in selection of stable vectors expressing TK. $TK^+$ resistant cells can be isolated and TK sequences rescued by standard PCR based techniques for mutation analysis (Cowell et al., CDNA Library Protocols, Published by Humana Press, 1996). In this manner, sequences are selected for both expression of functional protein and genomic stability of retroviral vector construct. Similar strategies can be employed for UPRT (SEQ ID NO: 11, 13), OPRT (SEQ ID NO: 15, 17) (Olah et al., Cancer Res. 40:2869-2875, 1980; and Suttle, Somatic Cell & Mol. Genet., 15(5):435-443, 1989) and other genes of interest.

Alternatively, OPRT, UPRT, TK or other PAE can be expressed in a separate vector containing a different ENV gene or other appropriate surface glycoprotein. This vector can be replication competent (Logg et al. J. Mol Biol. 369:1214 2007) or non replicative "first generation" retroviral vector that encodes the envelope nd the gene of interest (Emi et al. J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses [Palu 2000, Baum 2006, supra]. For example, a polynucleotide can comprise a sequence wherein the GAG and POL genes are deleted, the ENV corresponds to a xenotropic ENV domain from NZB MLV or VSV-g, and the IRES or a promoter such as RSV is operatively linked directly to OPRT, UPRT, TK, or other PAE gene.

Mixed infection of cells by VSV-g pseudotyped virus and amphotropic retrovirus results in the production of progeny virions bearing the genome of one virus encapsidated by the envelope proteins of the other (Emi et al., J. Virol. 65:1202, 1991). The same is true for other envelopes that pseudotype retroviral particles. For example, infection by retroviruses derived as above from both SEQ ID NOs: 19 and 20 results in production of progeny virions capable of encoding YCD2 and OPRT in infected cells. The resulting viruses can be used to treat a cell proliferative disorder in a subject in combination with 5-FC.

The recombinant retrovirus of the disclosure can be used for the treatment of a neuronal disorder for example, may optionally contain an exogenous gene, for example, a gene which encodes a receptor or a gene which encodes a ligand. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by an infected donor cell would be beneficial in a disorder where the subject's neural cell is defective in the production of such a gene product. A cell genetically modified to secrete a neurotrophic factor, such as nerve growth factor, (NGF), might be used to prevent degeneration of cholinergic neurons that might otherwise die without treatment.

Alternatively, cells be grafted into a subject with a disorder of the basal ganglia, such as Parkinson's disease, can be modified to contain an exogenous gene encoding L-DOPA, the precursor to dopamine. Parkinson's disease is characterized by a loss of dopamine neurons in the substantia-nigra of the midbrain, which have the basal ganglia as their major target organ.

Other neuronal disorders that can be treated similarly by the method of the disclosure include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic cells infected with a recombinant retrovirus of the disclosure containing an exogenous gene for a factor which would promote survival of these neurons can be accomplished by the method of the disclosure, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this disclosure. For example, antisense sequences, or a gene encoding an antagonist can be transferred to a neuronal cell and implanted into the hippocampal region of the brain.

For diseases due to deficiency of a protein product, gene transfer could introduce a normal gene into the affected tissues for replacement therapy, as well as to create animal models for the disease using antisense mutations. For example, it may be desirable to insert a Factor IX encoding nucleic acid into a retrovirus for infection of a muscle or liver cell.

The disclosure also provides gene therapy for the treatment of cell proliferative or immunologic disorders. Such therapy would achieve its therapeutic effect by introduction of an antisense, an siRNA or dominant negative encoding polynucleotide into cells having the proliferative disorder, wherein the polynucleotide binds to and prevents translation or expression of a gene associated with a cell-proliferative disorder. Delivery of heterologous nucleic acids useful in treating or modulating a cell proliferative disorder (e.g., antisense or siRNA polynucleotides) can be achieved using a recombinant retroviral vector of the disclosure. In another embodiment, a cell proliferative disorder is treated by introducing a CD polynucleotide of the disclosure, expressing the polynucleotide to produce a polypeptide comprising cytosine deaminase activity and contacting the cell with 5-fluorocytosine in an amount and for a period of time to produce a cytotoxic amount of 5-FU.

In addition, the disclosure provides polynucleotide sequence encoding a recombinant retroviral vector of the disclosure. The polynucleotide sequence can be incorporated into various viral particles. For example, various viral vectors which can be utilized for gene therapy include adenovirus, herpes virus, vaccinia, or, preferably, an RNA virus such as a retrovirus and more particularly a mammalian gamma retrovirus. The retroviral vector can be a derivative of a murine, simian or human retrovirus. Examples of retroviral vectors in which a foreign gene (e.g., a heterologous polynucleotide sequence) can be inserted include, but are not limited to: derivatives of Murine Leukemia virus (MLV), Moloney murine leukemia virus (MoMuLV), murine mammary tumor virus (MuMTV), Rous Sarcoma Virus (RSV), Gibbon ape leukemia virus (GALV), baboon endogenous virus (BEV), and the feline virus RD114. All of these vectors can transfer or incorporate a gene for a selectable marker so that transduced cells can be identified and generated. By inserting a heterologous sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Targeting is accomplished by using an antibody or ligand to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the heterologous polynucleotide. In addition, the retroviral vector can be targeted to a cell by utilizing a cell- or tissue-specific regulatory element contained in the LTR of the retroviral genome. Preferably the cell- or tissue-specific regulatory element is in the U3 region of the LTRs. In this way, after integration into a cell, the retroviral genome will only be expressed in cells where the cell- or tissue-specific promoter is active.

In yet another embodiment, the disclosure provides plasmids comprising a recombinant retroviral derived construct. The plasmid can be directly introduced into a target cell or a cell culture such as NIH 3T3 or other tissue culture cells. The resulting cells release the retroviral vector into the culture medium.

The disclosure provides a polynucleotide construct comprising from 5' to 3': a promoter or regulatory region useful for initiating transcription; a psi packaging signal; a gag encoding nucleic acid sequence, a pol encoding nucleic acid sequence; an env encoding nucleic acid sequence; an internal ribosome entry site nucleic acid sequence; a heterologous polynucleotide encoding a marker, therapeutic or diagnostic polypeptide; and a LTR nucleic acid sequence. As described elsewhere herein and as follows the various segment of the polynucleotide construct of the disclosure (e.g., a recombinant replication competent retroviral polynucleotide) are engineered depending in part upon the desired host cell, expression timing or amount, and the heterologous polynucleotide. A replication competent retroviral construct of the disclosure can be divided up into a number of domains that may be individually modified by those of skill in the art.

For example, the promoter can comprise a CMV promoter having a sequence as set forth in SEQ ID NO:19, 20 or 22 from nucleotide 1 to about nucleotide 582 and may include modification to one or more (e.g., 2-5, 5-10, 10-20, 20-30, 30-50, 50-100 or more nucleic acid bases) so long as the modified promoter is capable of directing and initiating transcription. In one embodiment, the promoter or regulatory region comprises a CMV-R-U5 domain polynucleotide. The CMV-R-U5 domain comprises the immediately early promoter from human cytomegalovirus to the MLV R-U5 region. In one embodiment, the CMV-R-U5 domain polynucleotide comprises a sequence as set forth in SEQ ID NO:19, 20 or 22 from about nucleotide 1 to about nucleotide 1202 or sequences that are at least 95% identical to a sequence as set forth in SEQ ID NO:19, 20, or 22 wherein the polynucleotide promotes transcription of a nucleic acid molecule operably linked thereto. The gag domain of the polynucleotide may be derived from any number of retroviruses, but will typically be derived from a gamma-retrovirus and more particularly from a mammalian gamma-retrovirus. In one embodiment the gag domain comprises a sequence from about nucleotide number 1203 to about nucleotide 2819 or a sequence having at least 95%, 98%, 99% or 99.8% (rounded to the nearest $10^{th}$) identity thereto. The pol domain of the polynucleotide may be derived from any number of retroviruses, but will typically be derived from an gamma-retrovirus and more particularly from a mammalian gammaretrovirus. In one embodiment the pol domain comprises a sequence from about nucleotide number 2820 to about nucleotide 6358 or a sequence having at least 95%, 98%, 99% or 99.9% (roundest to the nearest $10^{th}$) identity thereto. The env domain of the polynucleotide may be derived from any number of retroviruses, but will typically be derived from an gammaretrovirus or gamma-retrovirus and more particularly from a mammalian gammaretrovirus or gamma-retrovirus. In some embodiments the env coding domain comprises an amphotropic env domain. In one embodiment the env domain comprises a sequence from about nucleotide number 6359 to about nucleotide 8323 or a sequence having at least 95%, 98%, 99% or 99.8% (roundest to the nearest $10^{th}$) identity thereto. The IRES domain of the polynucleotide may be obtained from any number of internal ribosome entry sites. In one embodiment, IRES is derived from an encephalomyocarditis virus. In one embodiment the IRES domain comprises a sequence from about nucleotide number 8327 to about nucleotide 8876 or a sequence having at least 95%, 98%, or 99% (roundest to the nearest $10^{th}$) identity thereto so long as the domain allows for entry of a ribosome. The heterologous domain can comprise a cytosine deaminase of the disclosure. In one embodiment, the CD polynucleotide comprises a human codon optimized sequence. In yet another embodiment, the CD polynucleotide encodes a mutant polypeptide having cytosine deaminase, wherein the mutations confer increased thermal stabilization that increase the melting temperature (Tm) by 10° C. allowing sustained kinetic activity over a broader temperature range and increased accumulated levels of protein. In one embodiment, the cytosine deaminase comprises a sequence as set forth in SEQ ID NO:19 or 22 from about nucleotide number 8877 to about 9353. The heterologous domain may be followed by a polypurine rich domain. The 3' LTR can be derived from any number of retroviruses, typically an gammaretrovirus and preferably a mammalian gammaretrovirus. In one embodiment, the 3' LTR comprises a U3-R-U5 domain. In yet another embodiment the LTR comprises a sequence as set forth in SEQ ID NO:19 or 22 from about nucleotide 9405 to about 9998 or a sequence that is at least 95%, 98% or 99.5% (rounded to the nearest $10^{th}$) identical thereto.

The disclosure also provides a recombinant retroviral vector comprising from 5' to 3' a CMV-R-U5, fusion of the immediate early promoter from human cytomegalovirus to the MLV R-U5 region; a PBS, primer binding site for reverse transcriptase; a 5' splice site; a ψ packaging signal; a gag, ORF for MLV group specific antigen; a pol, ORF for MLV polymerase polyprotein; a 3' splice site; a 4070A env, ORF for envelope protein of MLV strain 4070A; an IRES, internal ribosome entry site of encephalomyocarditis virus; a modified cytosine deaminase (thermostablized and codon optimized); a PPT, polypurine tract; and a U3-R-U5, MLV long terminal repeat. This structure is further depicted in FIG. 3.

The disclosure also provides a retroviral vector comprising a sequence as set forth in SEQ ID NO:19, 20 or 22.

A number of chemotherapeutic agents are currently on the market having varying degrees of success from full remission to temporary remission and prolonged life with expected recurrence. Some of the cancer therapeutic agents on the market target the vascular angiogenic properties of tumor. The composition target the angiogenesis of tumors seeking to reduces blood supply and nutrients to the tumor or cancer and thereby reduce the tumor and prolong a subject's life. VEGF is an angiogenic factor known to play a role in tumor growth. Thus, antagonists of VEGF have been developed as anti-cancer agents.

Human VEGF mediates neoangiogenesis in normal and malignant vasculature; it is overexpressed in most malignancies and high levels have correlated with a greater risk of metastases and poor prognosis in many. When VEGF interacts with its receptor in in vitro models of angiogenesis, endothelial cell proliferation and new blood vessel formation occur. In animal models, VEGF has been demonstrated to induce vascular endothelial-cell proliferation/migration, sustain survival of newly-formed blood vessels, and enhance vascular permeability.

A VEGF antagonist agent is one that targets or negatively regulates the VEGF signaling pathway. Examples include VEGF inhibitors (e.g., agents that directly inhibit VEGF (e.g., VEGF-A, -B, -C, or -D), such as by binding VEGF (e.g., anti-VEGF antibodies such as bevacizumab (AVASTIN®) or ranibizumab (LUCENTIS®), or other inhibitors such as pegaptanib, NEOVASTAT®, AE-941, VEGF Trap, and PI-88)), modulators of VEGF expression (e.g., INGN-241, oral tetrathiomolybdate, 2-methoxyestradiol, 2-methoxyestradiol nanocrystal dispersion, bevasiranib sodium, PTC-299, Veglin), inhibitors of a VEGF receptor (e.g., KDR or VEGF receptor III (Flt4), for example anti-KDR antibodies, VEGFR2 antibodies such as CDP-791, IMC-1121B, VEGFR2 blockers such as CT-322), modulators of VEGFR expression (e.g., VEGFR1 expression modulator Sirna-027) or inhibitors of VEGF receptor downstream signaling. In some aspects described herein, the VEGF antagonist agent is bevacizumab, pegaptanib, ranibizumab, sorafenib, sunitinib, AE-941, VEGF Trap, pazopanib, vandetanib, vatalanib, cediranib, fenretinide, squalamine, INGN-241, oral tetrathiomolybdate, tetrathiomolybdate, Panzem NCD, 2-methoxyestradiol, AEE-788, AG-013958, bevasiranib sodium, AMG-706, axitinib, BIBF-1120, CDP-791, CP-547632, PI-88, SU-14813, SU-6668, XL-647, XL-999, IMC-1121B, ABT-869, BAY-57-9352, BAY-73-4506, BMS-582664, CEP-7055, CHIR-265, CT-322, CX-3542, E-7080, ENMD-1198, OSI-930, PTC-299, Sirna-027, TKI-258, Veglin, XL-184, or ZK-304709.

Bevacizumab (AVASTIN®) (rhuMAb-VEGF)(Anti-VEGF monoclonal antibody) is a recombinant human/murine chimeric monoclonal antibody directed against vascular endothelial growth factor (VEGF)). It is prepared by engineering VEGF-binding residues of a murine anti-VEGF monoclonal antibody into framework regions of human immunoglobulin-1 (IgG1) (Prod Info Avastin, 2004). Only 7% of the amino acid sequence is derived from the murine antibody, with 93% from IgG1. Bevacizumab binds and neutralizes all human VEGF forms via recognition of binding sites for the two human VEGF receptor types (flt-1 and flk-1). In animal models, the antibody has been shown to stabilize established tumors or suppress tumor growth by inhibiting angiogenesis induced by VEGF.

The pharmacokinetics of bevacizumab are linear after doses of 0.3 mg/kg or greater (Anon, 2002). Following 90-minute intravenous infusions of 0.3, 1, 3, and 10 mg/kg in advanced cancer patients (n=25), peak serum concentrations of bevacizumab ranged from 5 to 9 mcg/mL, 21 to 39 mcg/mL, 52 to 92 mcg/mL, and 186 to 294 mcg/mL, respectively; slight accumulation was observed with repeat doses (weekly), but this was not significant and pharmacokinetics remained linear. Steady-state levels of bevacizumab were obtained in 100 days after 1 to 20 mg/kg weekly, every 2 weeks, or every 3 week.

The recommended dose of bevacizumab is 5 milligrams/kilogram infused intravenously over 30 minutes every 2 weeks until disease progression diminishes. Bevacizumab should follow chemotherapy. Efficacy of single-agent bevacizumab has not been established. Bevacizumab (which may be coadministered with the gemcitabine and docetaxel, or within a week before or after chemotherapy), is administered intravenously, at about 1 mg/kg to about 15 mg/kg, preferably about 5 mg/kg.

The methods and compositions of the disclosure are useful in combination therapies including therapies with bevacizumab. As described herein a replication competent retrovirus (RCR) of the disclosure comprising a therapeutic (e.g., a cytotoxic gene) is useful in treating cell proliferative disorders. An advantage of the RCR of the disclosure includes its ability to infect replicating cells cancer cells. Where the transgene of the vector comprises a cytotoxic gene (e.g., a gene that encodes a polypeptide that converts a non-cytotoxic agent to a cytotoxic agent) provides the ability to kill cancer cells.

The disclosure provides methods for treating cell proliferative disorders such as cancer and neoplasms comprising administering an RCR vector of the disclosure produced by the HT1080+T5.0002 cells or similar HT1080 derived cells producing vectors encoding other heterologous genes, followed by treatment with a chemotherapeutic agent or anticancer agent. In one embodiment, the RCR vector is administered to a subject for a period of time prior to administration of the chemotherapeutic or anti-cancer agent that allows the RCR to infect and replicate. The subject is then treated with a chemotherapeutic agent or anti-cancer agent for a period of time and dosage to reduce proliferation or kill the cancer cells. In one aspect, if the treatment with the chemotherapeutic or anti-cancer agent reduces, but does not kill the cancer/tumor (e.g., partial remission or temporary remission), the subject may then be treated with a non-toxic therapeutic agent (e.g., 5-FC) that is converted to a toxic therapeutic agent in cells expression a cytotoxic gene (e.g., cytosine deaminase) from the RCR. Using such methods the RCXR vectors of the disclosure are spread during a replication process of the tumor cells, such cells can then be killed by treatment with an anti-cancer or chemotherapeutic agent and further killing can occur using the RCR treatment process described herein.

In yet another embodiment of the disclosure, the heterologous gene can comprise a coding sequence for a target antigen (e.g., a cancer antigen). In this embodiment, cells comprising a cell proliferative disorder are infected with an RCR comprising a heterologous polynucleotide encoding the target antigen to provide expression of the target antigen (e.g., overexpression of a cancer antigen). An anticancer agent comprising a targeting cognate moiety that specifically interacts with the target antigen is then administered to the subject. The targeting cognate moiety can be operably linked to a cytotoxic agent or can itself be an anticancer agent. Thus, a cancer cell infected by the RCR comprising the targeting antigen coding sequences increases the expression of target on the cancer cell resulting in increased efficiency/efficacy of cytotoxic targeting.

Blocking of interactions between cells of the immune system has been shown to have significant immunological effects, either activating or suppressing (Waldmann Annu Rev Med. 57:65 2006). For example, blockade of the interaction of CTLA-4 (CD 152) and B7.1 (CD80) which modulates the activation of T cells has been shown to cause immune stimulation, presumably by blocking this suppressive interaction (Peggs et al. Curr. Opin. Immunol. 18:206, 2006). This blockade can potentially be achieved either by antibodies against CTLA-4 or by soluble B7.1. Systemic administration of these types of molecules can have undesirable global effects which can at a minimum lead to deleterious side-effects or even death in the case of one C28 agonist (Suntharalingam et al. NEJM 355 1018 2006). Pfizer has been developing one such anti-CTLA-4 blockading antibody (CP-675,206) as an anticancer reagent but has recently stopped development because of significant side effects. Local delivery of blockading molecules that are released into the local environment, from the tumor after infection with a replication competent vector encoding such molecules that are released into the extracellular space, provides the immune modulation locally and avoid these serious side effects. The blockading molecules are antibodies, single chain antibodies, soluble versions of the natural ligand or other peptides that bind such receptors.

Thus in yet another embodiment, an RCR of the disclosure can comprise a coding sequence comprising a binding domain (e.g., an antibody, antibody fragment, antibody domain or receptor ligand) that specifically interacts with a cognate antigen or ligand. The RCR comprising the coding sequence for the binding domain can then be used to infect cells in a subject comprising a cell proliferative disorder such as a cancer cell or neoplastic cell. The infected cell will then express the binding domain or antibody. An antigen or cognate operably linked to a cytotoxic agent or which is cytotoxic itself can then be administered to a subject. The cytotoxic cognate will then selectively kill infected cells expressing the binding domain. Alternatively the binding domain itself can be an anti-cancer agent.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab').sub.2, a Fd fragment, a Fv fragments, and dAb fragments) as well as complete antibodies.

The VH and VL regions can be further subdivided into regions of hypervariability, termed "complementarity determining regions" (CDR), interspersed with regions that are more conserved, termed "framework regions" (FR). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two .beta.-sheets formed of about seven .beta.-strands, and a conserved disulphide bond (see, e.g., A. F. Williams and A. N. Barclay 1988 Ann. Rev Immunol. 6:381-405). The canonical structures of hypervariable loops of an immunoglobulin variable can be inferred from its sequence, as described in Chothia et al. (1992) J. Mol. Biol. 227:799-817; Tomlinson et al. (1992) J. Mol. Biol. 227:776-798); and Tomlinson et al. (1995) EMBO J. 14(18):4628-38.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site"), e.g., a structure that interacts with Tie1, e.g., binds to or inhibits Tie1.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The term "antibody" includes intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity.

The term "monospecific antibody" refers to an antibody that displays a single binding specificity and affinity for a particular target, e.g., epitope. This term includes a "monoclonal antibody" which refers to an antibody that is produced as a single molecular species, e.g., from a population of homogenous isolated cells. A "monoclonal antibody composition" refers to a preparation of antibodies or fragments thereof of in a composition that includes a single molecular species of antibody. In one embodiment, a monoclonal antibody is produced by a mammalian cell. One or more monoclonal antibody species may be combined.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human or effectively human. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human or effectively human. For example, FR1, FR2, and FR3 collectively can be at least 70, 75, 80, 85, 90, 92, 95, 98, or 99% identical to a human sequence encoded by a human germline V segment of a locus encoding a light or heavy chain sequence.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin light chains (about 25 Kd or 214 amino acids) are encoded by a variable region gene at the NH2-terminus (about 110 amino acids) and a kappa or lambda constant region gene at the COOH— terminus. Full-length immunoglobulin heavy chains (about 50 Kd or 446 amino acids), are similarly encoded by a variable region gene (about 116 amino acids) and one of the other aforementioned constant region genes, e.g., gamma (encoding about 330 amino acids). A light chain refers to any polypeptide that includes a light chain variable domain. A heavy chain refers to any polypeptide that a heavy chain variable domain.

The disclosure provides a method of treating a subject having a cell proliferative disorder. The subject can be any mammal, and is preferably a human. The subject is contacted with a recombinant replication competent retroviral vector of the disclosure. The contacting can be in vivo or ex vivo. Methods of administering the retroviral vector of the disclosure are known in the art and include, for example, systemic administration, topical administration, intraperitoneal administration, intra-muscular administration, intracranial, cerebrospinal, as well as administration directly at the site of a tumor or cell-proliferative disorder. Other routes of administration known in the art.

Thus, the disclosure includes various pharmaceutical compositions useful for treating a cell proliferative disorder. The pharmaceutical compositions according to the disclosure are prepared by bringing a retroviral vector containing a heterologous polynucleotide sequence useful in treating or modulating a cell proliferative disorder according to the disclosure into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

For example, and not by way of limitation, a retroviral vector useful in treating a cell proliferative disorder will include an amphotropic ENV protein, GAG, and POL proteins, a promoter sequence in the U3 region retroviral genome, and all cis-acting sequence necessary for replication, packaging and integration of the retroviral genome into the target cell.

As described above, the disclosure provides a host cells (e.g., a 293 cells or HT1080 cells) that are transduced (transformed or transfected) with a vector provided herein. The vector may be, for example, a plasmid (e.g., as used with 293T cells), a viral particle (as used with HT1080 cells), a phage, etc. The host cells can be cultured in conventional nutrient media modified as appropriate for activating promoters, selecting transformants, or amplifying a coding polynucleotide. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

In one embodiment of the disclosure, a producer cell produces replication competent retroviral vectors having increased stability relative to retroviral vectors made by conventional transient transfection techniques. Such increased stability during production, infection and replication is important for the treatment of cell proliferative disorders. The combination of transduction efficiency, transgene stability and target selectivity is provided by the replication competent retrovirus. The compositions and methods provide insert stability and maintains transcription activity of the transgene and the translational viability of the encoded polypeptide.

The following examples are meant to further illustrate the invention and are not meant to limit the broader disclosure above.

EXAMPLES

AC3-yCD2 ("V" viral particle) was produced from a HT1080+T5.0002 producer line derived from the HT1080 human fibrosarcoma cell line (ATCC, Catalog #CCL-121) obtained directly from the American Type Culture Collection (P.O. Box 1549, Manassas, Va.).

The cell line HT1080+T5.0002 was expanded to create a pre-bank and a subsequent master cell bank (MCB). The MCB was used to produce clinical lots. The flow diagram for generating the pre-bank and the master cell bank is shown in FIG. 1.

The Toca511 viral vector is encoded by a plasmid (pAC3-yCD2; a.k.a. T5.0002) consisting of 11,893 base pairs of nucleotides. Diagram 1 below provides a restriction enzyme map of the total construct of the pAC3-yCD2 plasmid along with the sequence location of the certain genetic elements.

General Scheme for Making Stable Expression Producer Cell Lines Making Replication Competent Vector AC3-yCD2(V).

The vector producer cell line "HT1080+T5.0002", was produced by transducing naïve HT1080 cells with AC3-yCD2 virus produced transiently in 293T cells by transfection (See FIG. 1). The transient transfection used to produce AC3-yCD2 (viral particles) was performed using the GLP sequenced "qualified plasmid stock". More specifically, transiently produced AC3-yCD2 vector was harvested after 48 hours post transfection and filtered through a 0.45 um filter with 0.8 mL of filtered supernatant used to transduce a 75% confluent culture of HT1080 cells containing 15 mL of media. This infection volume converted to an approximate transduction dose of about 0.1 transduction unit (TU) per cell. The transduction was allowed to spread throughout the culture for 9 days with cells refed or passaged every 2-4 days prior to freezing down the initial Pre-Bank stock consisting of 12 vials with each vial containing approximately $5 \times 10^6$ cells per vial. The freezing media included 10% DMSO, USP (Cryoserv, Bioniche Pharma USA, LLC, Lake Forest, Ill.) and 90% gamma-irradiated fetal bovine serum (Hyclone Laboratories. Inc, Logan Utah). Cells were frozen in a −80° C. freezer and then transferred to a liquid nitrogen freezer under vapor phase conditions the following day. The media used for growing HT1080+T5.0002 cells to produce the vector comprises a defined DMEM media, GlutaMax (L-glutamine substitute), non-essential amino acids (NEAA), and Defined Fetal Bovine Serum (FBS).

The 293T cell line was developed from HEK (Human Embryonic Kidney) 293 cells and was originally described in 1987 (Dubridge 1987). The cell line was developed by transfecting a temperature sensitive SV40 T-antigen mutant, tsA1609 (Dubridge 1987), into HEK 293 cells (Graham 1977). The 293T cells are more susceptible to transfection than the original HEK 293 cell line. Because of their higher transfectability, 293T cells have commonly been used to produce high titer vectors by transient transfection (Yang et al. Hum. Gene Ther. 10:123-132 1999).

Example 2: Preparation of Vector from HT1080+T5.0002 Stable Expression Producer Line as an Adherent Line with Fetal Calf Serum HT1080+T5.0002 cells are grown in disposable multilayered cell culture vessels (Cell Stack, Corning). Production of the crude Toca 511 retroviral vector is performed by harvesting the conditioned media from confluent cultures of HT1080+T5.0002 cells harvested every 10-24 hour period over 2-4 harvest cycles using a manual fed batch process using multiple Cell Stacks containing approximately 1.2 L of conditioned media each. Crude TOCA 511 retroviral vector is harvested directly into 10-20L process bags and stored at 2-8° C. until approximately 40L of material is collected. Sample of the combined crude pool harvest used for PTC mycloplasma, in vitro viral testing, bioburden, informational PCR titering and retentions.

The crude vector material is clarified by passing through a 0.45 micron filter cartridge and treated with Benzonase to digest host cell genomic DNA. The clarified and DNA digested TOCA 511 vector is then captured and concentrated using anion exchange (AEX) chromatography. The eluted concentrated bulk product then undergoes a buffer exchange and purification step using size exclusion (SEC) chromatography. The formulation buffer comprises Tris-based formulation buffer containing sodium chloride, sucrose, mannitol, ascorbate, ascorbic acid and human serum albumin. The formulated bulk is 0.2 um filtered to insure sterility, sampled for testing and then divided in multiple containers as bulk material stored frozen below ($<$) $-65°$ C.

The vector produced from HT1080+T5.0002 cells was tested on naïve PC3 (human prostate adenocarcinoma) or U-87 cells (human glioblastoma-astrocytoma), depending on the test. These tests included; (1) transfer of CD (cytosine deaminase) protein expression by Western analysis, (2) functional CD activity of the CD protein to convert 5-FC to 5-FU by HPLC analysis, as well as, (3) measuring the ability for 5-FC to kill U-87 cells (MTS assay) transduced with AC3-yCD2 (V).

Example 3: Construction of Vectors Encoding Cytosine Deaminase, Green Fluorescent Protein (GFP), Mouse Gamma Interferon (IFN) and Other Proteins or Nucleic Acids These replicating retroviral vectors were constructed as previously described in WO 2010/036986. Table 1 describing the nature of some of these vectors is included below.

TABLE 1

Vector constructs and names

| Ref. Code | Reference name | Original Name | 5'LTR Prom | Envelope | Vector | IRES | Transgene | 3'LTR |
|---|---|---|---|---|---|---|---|---|
| T5.0000 | pACE-yCD | pACE-CD (Tai et al. 2005) | CMV | Ampho (4070A) | pACE | EMCV | Wt yeast CD | MLV U3 |
| T5.0001 | pAC3-yCD1 | CDopt sequence | CMV | Ampho (4070A) | pAC3 | EMCV | modified CD | MLV U3 |
| T5.0002 | pAC3-yCD2 | CDopt + 3pt | CMV | Ampho (4070A) | pAC3 | EMCV | Modified CD | MLV U3 |
| T5.0006 | pAC3-eGFP | pAC3-emd, pAC3GFP | CMV | Ampho (4070A) | pAC3 | EMCV | Emerald GFP | MLV U3 |
| T5.0007 | pAC3-yCD | pAC3-yCD | CMV | Ampho (4070A) | pAC3 | EMCV | Wt yeast CD | MLV U3 |
|  | pAC3-mIFNg | pAC3-mIFNg | CMV | Ampho (4070A) | pAC3 | EMCV | Mouse Gamma IFN | MLV U3 |
|  | pAC3-hIFNg | pAC3-hIFNg | CMV | Ampho (4070A) | pAC3 | EMCV | Human Gamma IFN | MLV U3 |

Other vectors that can be produced using the cell lines and methods described in this application, are also described in WO 2010/036986. These include vectors encoding single chain antibodies, IL-2, miRNA's and siRNA's under the control of a pol III promoter, and siRNA target sequences.

Example 4: Quantitative PCR Titering Assay

The functional vector concentration, or titer, is determined using a quantitative PCR-based (qPCR) method. In this method, vector is titered by infecting a transducible host cell line (e.g. PC-3 human prostatic carcinoma cells, ATCC Cat #CRL-1435) with a standard volume of vector and measuring the resulting amount of provirus present within the host cells after transduction. The cells and vector are incubated under standard culturing condition (37° C., 5% $CO_2$) for 24 hr to allow for complete infection prior to the addition of the anti-retroviral AZT to stop vector replication. Next, the cells are harvested from the culture dish and the genomic DNA (gDNA) is purified using an Invitrogen Purelink gDNA purification kit and eluted from the purification column with sterile RNase-/DNase-free water. The $A_{260}/A_{280}$ absorbance ratio is measured on a spectrophotometer to determine the concentration and relative purity of the sample. The gDNA concentrations are normalized with additional RNase-/DNase-free water to the lowest concentration of any given set of gDNA preparations such that the input DNA for the qPCR is constant for all samples analyzed. Genomic DNA purity is further assessed by electrophoresis of an aliquot of each sample on an ethidium bromide stained 0.8% agarose gel. If the sample passes an $A_{260}/A_{280}$ absorbance range of 1.8-2.0 and shows a single band of gDNA, then the sample is ready for qPCR analysis of provirus copy number of the vector. Using primers that interrogate the LTR region of the provirus (reverse-transcribed vector DNA and vector DNA that is integrated into the host gDNA), qPCR is performed to estimate the total number of transduction events that occurred when the known volume of vector was used to transduce the known number of cells. The number of transduction events per reaction is calculated from a standard curve that utilizes a target-carrying plasmid of known copy-number that is serial diluted from $10^7$ to 10 copies and measured under identical qPCR conditions as the samples. Knowing how many genomic equivalents were used for each qPCR reaction (from the concentration previously determined) and how many transduction events that occurred per reaction, we determine the total number of transduction events that occurred based on the total number of cells that were present at the time of transduction. This value is the titer of the vector after dilution into the medium containing the cells during the initial transduction. To calculate the corrected titer value, the dilution is corrected for by multiplying through by the volume of culture and the volume of titer divided by the volume of titer. These experiments are performed in replicate cultures and analyzed by qPCR using triplicate measurements for each condition to determine an average titer and with its associated standard deviation and coefficient of variance.

Example 5: Potency Assay for Vectors Encoding Cytosine Deaminase

This assay assesses cell samples for cytosine deaminase activity 4 days post-transduction and measures both the replicative capacity of the vector and the corresponding cytosine deaminase activity. U-87 cells were grown in 96 well plates and transduced with a dilution series of virus (up to 12 dilutions at half log intervals). 5-Fluorocytosine was added to cells for one hour, the reaction was stopped by addition of 10% trichloroacetic acid and the resulting filtered mixture analyzed by HPLC for cytosine deaminase activity by measuring the 5-fluorouracil produced. The HPLC assay was performed on a Shimadzu LC20AT unit connected in series with a photoarray detector and autoinjector. The HPLC method used a Hypersil BDS C18 column run isocratically at 1 mL/min with 95% Buffer A: 50 mM ammonium phosphate containing 0.1% tetra-n-butylammonium perchlorate with pH adjustment of the buffer to 2.1 with phosphoric acid and 5% Solvent B: 100% methanol. The run time was 6 minutes. The photodiode detector array scans from 190 to 350 nm with chromatograms selected to display absorbance at 264 nm for 5-fluorouracil. The Browser function is used to transfer data in a bulk report with the 5-fluorouracil retention time and area at 264 nm and the 5-fluorocytosine retention time and area at 285 nm reported. Peak area is then plotted against inputted dilution to generate a 4-parameter curve fit and the EC50 values of the test sample is compared to an in-house Reference Vector (See FIG. 10 and FIG. 11 for examples of these plots).

Example 6: Vector Purification and Concentration

Vectors of the disclosure were manufactured by transient transfection on 293T cells, or from a producer cell pool, or from a cloned producer cell line. The medium can be with serum or serum free, and the cells can be grown as adherent cells or in suspension, normally in perfusion mode. The medium was harvested, and when made from the stable producer cell lines, stored for up to 2 weeks at 2-8 degrees centigrade. Vector from the stable cell lines had a half life at 2-8 degrees C. that is greater than 7 days, while this is not true for material made from transient transfection. This bulk harvest was then filtered through a 0.45 micron filter cartridge, treated with benzonase (L. Shastry et al Hum Gene Ther 15:221 2004) and further chromatography column steps. (see, e.g., U.S. Pat. No. 5,792,643; T. Rodriguez et al. J Gene Med 9:233 2007; P. Sheridan et al Mol. Ther. 2:262-275 2000). The vector preparations were loaded on an anion exchange column and the vector eluted in a NaCl gradient. The fraction containing vector was initially identified using the PCR assay (example 4), and subsequently by A260, and positive fractions collected and pooled. The preparation was then loaded on a size exclusion column (SEC) to remove salt and other remaining contaminants. The SEC is eluted with formulation buffer and the vector fraction on the SEC column was collected from the void volume, and tested as bulk material for titer. It was then filtered through 0.2 micron filters and 0.8 to 3 ml aliquoted into vials. Clinical material is released based on standard testing such as sterility, mycoplasma and endotoxins, plus product specific potency (example 5, FIGS. 10 & 11), strength (example 4), and identity testing. Titer is determined as Transducing Units (TU) by PCR quantitation of integrated viral vector DNA in target cells (Example 4). The final product is targeted to have a titer of up to $10^9$ TU/ml formulated in isotonic Tris-buffered sucrose solution, as a sterile injectable.

In general, to accurately and precisely determine the strength of vector lots, a quantitative PCR-based titer assay has been developed (described in general terms in example 4). The details of the assay procedure consist of the following steps:

Transduction.

Transductions are performed in a 12-well plate format using the stable human prostate adenocarcinoma derived PC-3 cell line. For each test sample, three dilutions of un-titered vector preparation are used to transduce PC-3 cells in triplicate wells. Viral replication is stopped 24 hours post-transduction with azidothymidine (AZT). Cells are maintained for an additional 24-64 hours prior to harvesting and genomic DNA purification.

Example 8: Cloning of a Non-Clonal Pool of Infected HT1080 Cells

Dilution Seeding.

Pre-warm media and Multiple 96 well cell culture plates were labelled in order to identify the clone based on the plate and well position and the wells were filled with prewarmed media containing single cell suspension of the HT1080. An early passage of 100% infected HT1080 cells was harvested by trypsinizing and creating a single cell suspension consisting of 1 cell per 600 microL. 200 microL was delivered into each well of a 96 well plate in order to seed approximately 0.3 cells per well. In performing this procedure, a majority of the wells received either 0, 1 or 2 cells per well. Cells were allowed to attach for approximately 4 hours and each well examined to eliminate wells that have received more than 1 cell per well or are empty.

Clone Propagation.

The wells that initially contained 1 cell per well were cultured by replacing 4 of the media (approximately 100 μL) with fresh 100 microL every 3-4 days for every well. Accidental transfer of cells from one well to another was avoided by replacing the tip used to feed each well during media replacement. Full media replacement was required as cells started to approach confluence in the well. Once the cells reached confluence, each clonal candidate was passaged to a well of a 48 well plate to continue expansion. Each clone was propagated and passed to a well of a 6 well plate, followed by a T-25 flask, followed by T-75 flask each time the cells reached confluence. Once the clonal cells reached confluence in a T-75 flask, at least 2-3 vials of cryopreserved cells containing $1-2\times10^6$ cells per vial were prepared.

Clone Selection Based on Performance.

Once the clone candidates were frozen down, cell culture experiments were performed to identify the best performing clone and back up clones based on titer production performance and ideal cell culture attributes. The best clone was chosen based on (1) the ability of the clone to provide the highest sustained titers over 2-4 subsequent days with daily media replacement [See FIG. 12 and Table 2, below]; (2) the ability of the virus produced to transfer expression of the desired gene of interest to a naïve cell (See FIGS. 10 and 11); (3) the ability of the clone to divide reasonably having a doubling time between 18-30 hours and ability to reach 100% confluence as a uniform lawn of cells with minimal cell detachment upon reaching confluence.

Example 9: Infection of D-17 and Cf2-Th Cell Lines to Make a Non-Clonal Pool and Subsequent Clonal Vector Producer Cell Line Candidates To produce D-17 (canine osteosarcoma; ATCC #CCL-183) and Cf2-Th (canine thymus; ATCC #CRL-1430) cell line vector producer pools and dilution clones that express MLV replication competent retroviral vector, the exact same methods described above for HT-1080 cells were used to create D-17 and Cf2-Th cell lines. Results are shown in Table 2 below analysis for the presence of GFP fluorescence to determine the percentage of infected cells at each day post infection. The inoculating T5.0006 viral supernatant was derived from internal infected cultures of Cf2-Th stable producer cells made as described above and characterized fro titer of virus produced.

Cf2-Th+T5.0006 Producer Line and T5.0006(V) Virus: A culture of Cf2-Th cells, was previously infected with transiently produced T5.0006(V) virus generated by transfecting the plasmid pAC3-emd (aka pT5.0006) into 293T cells using standard calcium phosphate transfection procedures. After several passages and on the day of infection of the three canine glioma tumor cells lines, fresh viral supernatants

TABLE 2

Data to Support Creation of Producer Pools and Subsequent Dilution Clones of HT-1080, D-17 and Cf2-Th Replication Competent Retroviral Vectors

| Cell Line Vector Producing Cell Line | MLV Replication Competent Vector Expressed | Parental Cell Line | Titer Sample | Titers Observed (TU/mL)* |
| --- | --- | --- | --- | --- |
| HT1080 + T5.0002 (Non-Clonal Pool) | AC3-yCD2 | HT-1080 | HT + T5.0002, Day 2 | 1.56E+06 |
| | | | HT + T5.0002, Day 3 | 2.23E+06 |
| | | | HT + T5.0002, Day 4 | 1.90E+07 |
| | | | HT + T5.0002, Day 5.5 | 2.57E+07 |
| HT5.yCD2.128A (Dilution Clone) | AC3-yCD2 | HT-1080 | Clone 12-8, Day 0 | 5.26E+06 |
| | | | Clone 12-8, Day 1 | 7.94E+06 |
| | | | Clone 12-8, Day 2 | 1.00E+07 |
| | | | Clone 12-8, Day 3 | 1.02E+07 |
| D17 + T5.0002 (Non-Clonal Pool) | AC3-yCD2 | D-17 | D17 + T5.0002, Day 2 | 4.20E+06 |
| | | | D17 + T5.0002, Day 3 | 3.83E+06 |
| | | | D17 + T5.0002, Day 4 | 4.87E+06 |
| | | | D17 + T5.0002, Day 5.5 | 1.39E+06 |
| D5.yCD2.1G7A (Dilution Clone) | AC3-yCD2 | D-17 | D5.yCD2.1G7A, Day 1 | 1.78E+06 |
| | | | D5.yCD2.1G7A, Day 2 | 2.54E+06 |
| | | | D5.yCD2.1G7A, Day 3 | 4.24E+06 |
| CF2 + T5.0002 (Non-Clonal Pool) | AC3-yCD2 | Cf2-Th | CF2 + T5.0002, Day 2 | 4.17E+04 |
| | | | CF2 + T5.0002, Day 3 | 6.97E+03 |
| | | | CF2 + T5.0002, Day 4 | 4.97E+06 |
| | | | CF2 + T5.0002, Day 5.5 | 3.14E+06 |
| CF5.yCD2.3A12A (Dilution Clone) | AC3-yCD2 | Cf2-Th | CF5.yCD2.3A12A, Day 1 | 1.81E+07 |
| | | | CF5.yCD2.3A12A, Day 2 | 2.68E+07 |
| | | | CF5.yCD2.3A12A, Day 3 | 3.78E+06 |

*TU/mL indicates transduction units per mL as determined by quantitative qPCR methods to determine copy number of integrated proviral MLV genomes post transduction into a titering naïve U-87 cell line.

Example 10: Testing Infectivity and Transfer of Express of Replication Competent Retroviral Vector Produced from Infected Cf2-Th Cells with T5.0006 (GFP Expressing Replication Competent Vector)

An evaluation was performed with the replication competent retroviral vector, T5.0006(V), encoding the gene for green fluorescent protein (GFP) to evaluate the vector's ability to infect and propagate in canine derived tumor cell lines. For this study, three canine glioblastoma cell lines, J3T-bg, SDT-3G and G06-A were received from the laboratory of Dr. Peter Dickinson (University of California, Davis; Vet Med Surgery and Radiological Sciences). All three of these cell lines were originally derived from spontaneous glioma explants and were within 8-14 passages of the original isolates. To test viral infectivity, 0.1 mL of 0.45 micron filtered T5.0006(V) viral supernatants were placed into triplicate 2 mL cultures containing $4.4 \times 10^5$ cells of each tumor type in 6-well culture plates with the exception of SDT-3G which was at $1.9 \times 10^4$ cells. Triplicate plates were prepared, one plate for each time point. To track infectivity, one plate with triplicate infections, and non-infected control wells, was harvested at days 1, 3 and 6 to perform FACs were collected from a confluent infected Cf2-Th culture and passed through a 0.45 micron syringe filter to remove any viable infected Cf2-Th cells.

Infection of the Three Canine Glioblastoma Cell Lines and the Positive Control HT-1080 Cell Line:

The three canine glioblastoma cell lines: J3Tbg, SDT-3G and G06-A, were received as cryopreserved cells on Nov. 20, 2008 from the laboratory of Dr. Peter Dickinson, University of California, Davis; Vet Med Surgery and Radiological Sciences. All three of these cell lines were originally derived from spontaneous gliomas and were within 8-14 passages of the original isolates as indicated in the documentation attached with the receipt of the frozen vials. The HT1080 positive control cell line was derived from in-house frozen stocks originally sourced from ATCC (CCL-121; Lot 6805248).

One vial was thawed of each cell line and cultured for several passages in DMEM media supplemented with 10% fetal bovine serum and 200 mM Glutamax and incubated at 37□C under 5% $CO_2$ conditions. One day prior to infecting the cells, one 6 well plate was seeded with 5E4 cells/cm2 (4.4E5 cells/well) for each tumor cell line in 2 mL of fresh complete DMEM media with the exception of the SDT-3G plates which were prepared at 1.9E4 cells/well. The positive control HT1080 cultures were seeded 3.5 hours before the addition of virus on the same day of the tumor cell line viral infections. Viral infections were performed by adding 0.1 mL of filtered T5.0006(V) to three wells out of each 6 well plate leaving three uninfected wells to serve as negative controls for FACS analysis. After infection, the plates were returned to the 37□C incubator. Triplicate plates were prepared for each cell line.

At 1, 3 and 6 days post infection, triplicate wells from each infected and non-infected cell line were harvested using trypzean reagent (Sigma-Aldrich), were washed in complete media and then fixed with 1% paraformaldehyde in PBS with 2% FBS and 0.09% sodium azide and stored refrigerated in the dark or on ice until subjected to FACS analysis. Note that the remaining cultures after the day 3 harvest point were passaged on day 3.

FACS Analysis:

All paraformaldehyde fixed cells were analyzed on a BD LSRII FACS machine located at Sidney Kimmel Cancer Center (SN H47200068) with analysis using BD FACS Diva Software Version 5.0.1. HT1080 and HT1080 100% GFP infected cells from a previous infection were used to set the gating. Each sample was read once.

Figure 13:
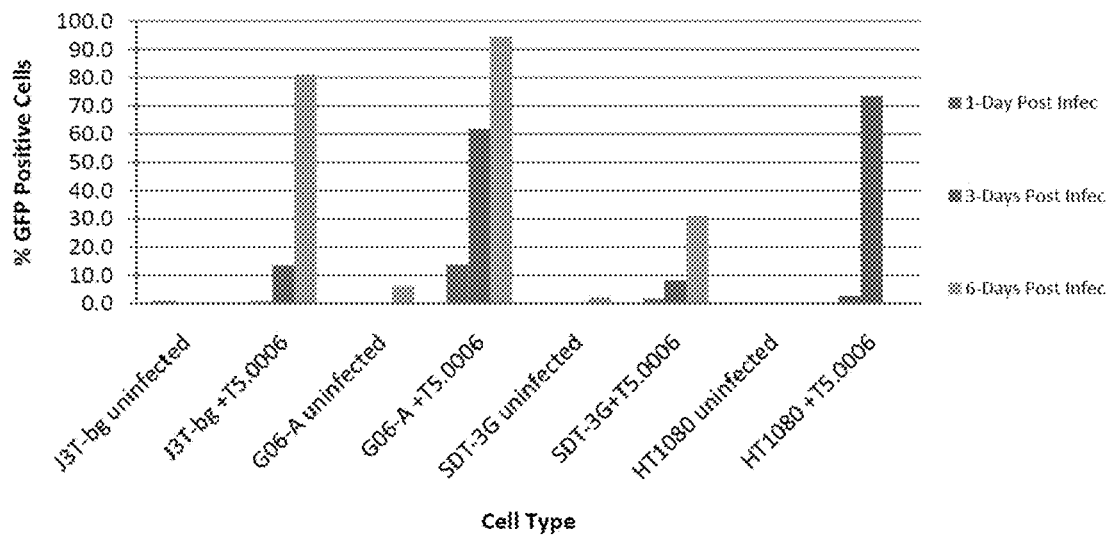
FIG. 13 shows viral spread of T5.0006 (GFP) Vector on three canine glioma cell lines at 1, 3 and 6 Days Post Infection.

Table 3 demonstrates the average results of the triplicate readings of the percent infected cells after 1, 3 and 6 days post infection. FIG. 13 shows the graphical representation of the data. The data suggests that each canine tumor line infected with T5.0006(V) demonstrated some level of GFP expression above back ground negative controls however differences in viral spread kinetics were observed between the different tumor cell lines. The G06-A tumor line demonstrated 94.5% GFP positivity 6 days post infection followed by J3T-bg and SDT-3G demonstrating 81.2% and 30.9% GFP positivity at the same harvest point respectively. All controls were valid with uninfected controls showing insignificant background levels of GFP expression and the HT1080 permissive positive control cell line demonstrating 73.4% GFP positivity by day 3 post infection (Day 6 samples were lost). In similar past experiments, using the same conditions, the human U87 glioma line becomes 80-90% GFP positive.

$2\times10^7$ cells into a 125 mL shaker flask containing 10 mL of 5% serum containing conditioned media and 10 mL of a selected serum free media of choice, resulting into a reduced serum concentration of 2.5%. In this case the serum free media was FreeStyle 293 Expression Media distributed through Invitrogen Corp, Carlsbad, Calif., The culture was placed on a shaking platform located in a tissue culture incubator with both temperature and $CO_2$ gas control. The shaking platform was set to a preferred 80 RPM and the incubator is set to a preferred 37° C. and a preferred 5% $CO_2$ conditions. Every 3-7 days, the culture was re-fed by collecting cells that are in suspension and reseeded into a new shaker flask containing 10 mL of the same initial conditioned media and 10 mL of fresh serum free media maintaining a level of serum of approximately 2.5%. The culture was examined at each re-feeding event with viable cell counts performed as needed to check for cell propagation. When the cells showed evidence of growth based on cell doubling or glucose consumption, a serum concentration of 1.67% was then targeted by adjusting the volume amount of condition media and fresh serum free media. The culture again was examined and refed every 3-7 days. When the cells show evidence of growth, a serum concentration of 1.25% was targeted by again adjusting the volume of conditioned media and fresh serum free media. This process was continued targeting subsequent serum conditions of 1.0%, 0.9%, 0.83% serum conditions until the cells were in 100% serum free conditions. During this adaptation process the cell culture was expanded to approximately 200 mL volume in a 1,000 mL shaking flask targeting a minimal viable culture of approximately 0.5 to $1.0\times10^6$ cell/mL. Once the cells reached 100% serum free conditions, the cells were continuously passaged under serum free conditions isolating single suspended cells by allowing heavier clumping cells to settle for short periods of time without agitation. Once the culture consists of approximately 95% population of the single cell suspension consistently, the culture could be frozen in cryopreservation media consisting of 10% DMSO and 90% serum free media using standard mammalian cell freezing conditions.

TABLE 3

Summary of Percent Positive Cells for GFP Expression on Three Canine Glioma Cell Lines after Infection with T5.0006 (GFP) Vector

| Days Post Infection | J3T-bg uninfected (% GFP Positive) | J3T-bg + T5.0006 (% GFP Positive) | G06-A uninfected (% GFP Positive) | G06-A + T5.0006 (% GFP Positive) | SDT-3G uninfected (% GFP Positive) | SDT-3G + T5.0006 (% GFP Positive) | HT1080 uninfected (% GFP Positive) | HT1080 + T5.0006 (% GFP Positive) |
|---|---|---|---|---|---|---|---|---|
| 1 Day | 0.8 | 0.7 | 0.0 | 13.8 | 0.3 | 1.6 | 0.3 | 2.5 |
| 3 Day | 0.5 | 13.4 | 0.1 | 61.8 | 0.3 | 8.1 | 0.0 | 73.4 |
| 6 Day | 0.3 | 81.2 | 6.2 | 94.5 | 2.2 | 30.9 | lost | lost | lost = test sample lost

Example 11: Adaptation of HT-1080 Replication Competent MLV Viral Vector Producer Cell Line from Serum and Adherence Dependence to a Serum Free Suspension Culture The serum free adaptation process was performed after screening and identification of suitable dilution clone of HT-1080 replication competent vector producing cell line. The serum free adaptation process can also be performed with a non-clonal vector producing HT1080 cell line. The adaptation process was initiated by seeding approximately Example 12: Vector Made from Stable Producer Cell Lines is More Stable that Vector Made by Transient Transfection in Long Term Storage Vector Production by Transient Transfection.

Crude supernatant containing replication competent MLV virus encoding either the gene for cytosine deaminase or the gene for green fluorescent protein were produced by two transient transfection methods. The first method used the standard calcium phosphate transfection procedure described by Graham and van der Eb using 293T cells which have commonly been used to produce high titer vectors as originally described by Yang 1999. The second transfection method used the commercially available proprietary transfecting reagent (Fugene) distributed by Promega (Madison, Wis.). Forty-eight hours after transfection, viral supernatants were filtered using a 0.2 or 0.45 micron filter, with aliquots frozen and stored at temperatures ≤−65° C. The frozen clarified supernatants were titered by the quantitative qPCR method to establish an initial concentration of infectious titer. Subsequent testing of the titer on various dates revealed that the viral preparations were not stabile and lost at least one log of titer as rapidly as 14 days as tested by the same quantitative qPCR method (See Table 4).

Vector Production from Stable Lines.

To compare this stability profile against replication competent MLV virus produced from stably infected HT-1080 cells, T5.0002 viral preparations were produced as described in the previous example and subsequently purified and formulated in a Tris sodium chloride isotonic buffer containing 10 mg/mL of sucrose and 1 mg/mL of human serum albumin. The specific T5.0002 lots used in this stability study are lots T003-002-40L, M100-09, M101-09 and M102-09 with the last three lots produced under good manufacturing practices (GMP). To evaluate stability of the virus, procedures used to address (1) infectious titer; and (2) transfer of expression in naïve cells.

Storage.

Both undiluted and 1/100 diluted doses of T5.0002 from lot T003-002-40L were pulled from ≤−65° C. long term storage conditions with vials subsequently thawed at 3, 6 and 12 months post-vialing and tested within the following assays: Strength, Potency, and TCID50.

TABLE 4

Various Replication Competent MLV Virus Produced by Transient Transfection

| Replication MLVirus Description | Parental Cell Line (Transfection Method) | Sample ID | qPCR Titer (TU/mL) |
|---|---|---|---|
| T5.0002 | 293T (Calcium Phosphate) | 051508-RCR-2 | 3.2 × 10$^7$ |
| T5.0002 | 293T (Calcium Phosphate) | 051508-RCR-2 | 1.4 × 10$^6$ |
| T5.0002 | 293T (Calcium Phosphate) | CS003 (2-D3-IN-080108-CS) | 1.3 × 10$^6$ |
| T5.0002 | 293T (Calcium Phosphate) | CS003 (2-D3-IN-080108-CS) | 2.4 × 10$^4$ |
| T5.0006$^{(2)}$ | HT-1080 (Fugene) | HT1080-D4-102508 | 2.3 × 10$^6$ |
| T5.0006 | HT-1080 (Fugene) | HT1080-D4-102508 | 2.8 × 10$^5$ |
| T5.0006 | 293T (Fugene) | 293T-D2-102308 | 2.6 × 10$^6$ |
| T5.0006 | 293T (Fugene) | 293T-D2-102308 | 2.3 × 10$^5$ |

GMP produced lots M100-09, M101-09 and M102-09 were prepared from the HT1080+T5.0002 stable producer cell line purified and stored at ≤−65° C. since preparation. Vials were pulled and thawed at 3, and 6 months post-vialing and tested within the following assays: Strength, Potency, TCID50, pH, osmolality and appearance.

Infectious Titer by Quantitative qPCR.

Figure 14:
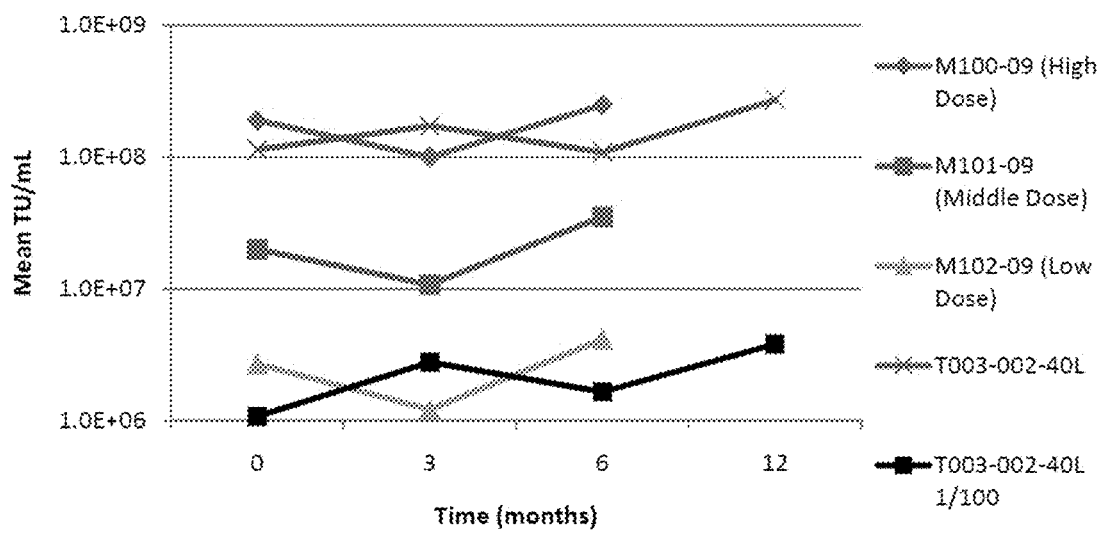
FIG. 14 shows measured titer trends of lots T003-002-40L and GMP lots at ≤−65° C. over 12 months.

No decrease in titer is observed for purified viral vector produced from the stably infected HT-1080 cell line when stored at ≤−65° C. for up to 12 months for all lots tested. Tables 5 and 6 show the measured titers for Lot T003-002-40L (Table 5) and GMP lots (Table 6). FIG. 14 shows the generated titer trend over 12 months for all lots tested.

TABLE 5

Measured titers of the development lots T003-002-40L (Undiluted and 1/100) at Release, and 3, 6 and 12 months stored ≤−65° C.

| T003-002-40L | Release | 3 M | 6 M | 12 M |
|---|---|---|---|---|
| | | TU/mL | | |
| Undiluted | 1.14E+08 | 1.73E+08 | 1.09E+08 | 2.71E+08 |
| 1/100 | 1.08E+06 | 2.79E+06 | 1.66E+06 | 3.82E+06 |

TABLE 6

Measured titers of Clinical lots M100-09 (High Dose), M101-09 (Mid Dose) and M102-09 (Low Dose) at Release, and 3 and 6 months stored at ≤−65° C.

| | Release | 3 M | 6 M | 1X F/T* |
|---|---|---|---|---|
| | | TU/mL | | |
| M100-09 | 1.90E+08 | 1.00E+08 | 2.49E+08 | 2.38E+08 |
| M101-09 | 2.00E+07 | 1.08E+07 | 3.52E+07 | 3.56E+07 |
| M102-09 | 2.70E+06 | 1.22E+06 | 4.15E+06 | 4.01E+06 |

*Vials were thawed at the 3 M timepoint, re-frozen at ≤−65° C. and tested with the 6 M samples.

Transfer of Biological Expression Assay Using Cell Culture and HPLC Analysis to Evaluate Stability of Viral Vector Stored ≤−65° C.

Figure 10:
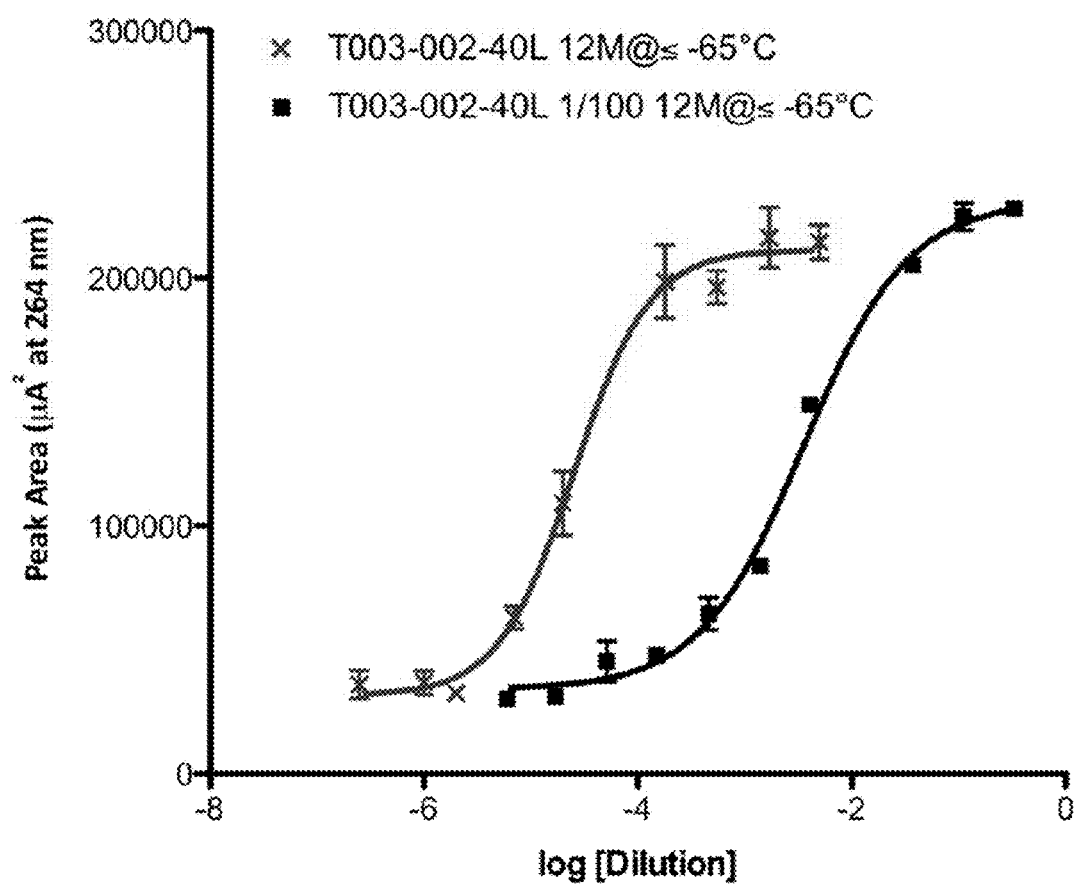
FIG. 10 shows Potency Dose Curves (see example 8) for Lot T003-002-40L (Undiluted and 1/100) at 12 months at ≤−65° C.
Figure 11:
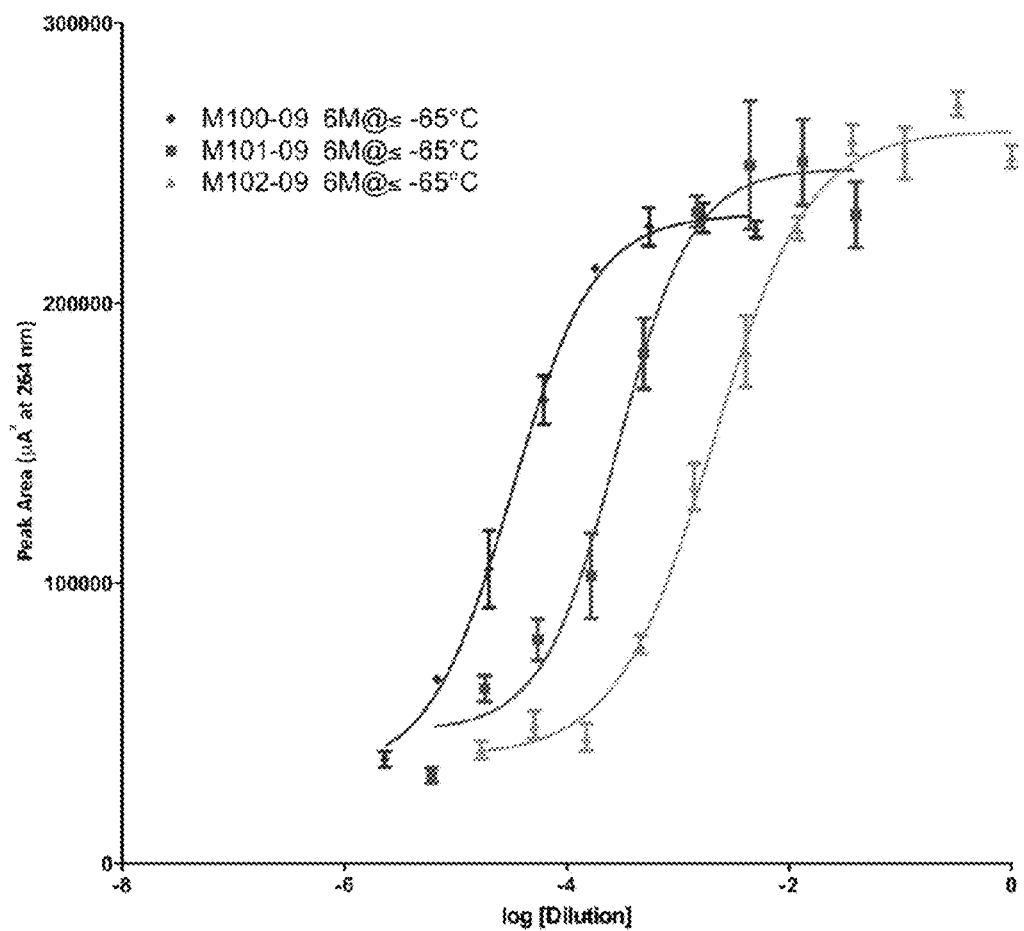
FIG. 11 shows potency cose curves for 3 lots, M100-09 (High Dose), M101-09 (Mid Dose) and M102-09 (Low Dose) at 6 months at ≤−65° C.
Figure 12:
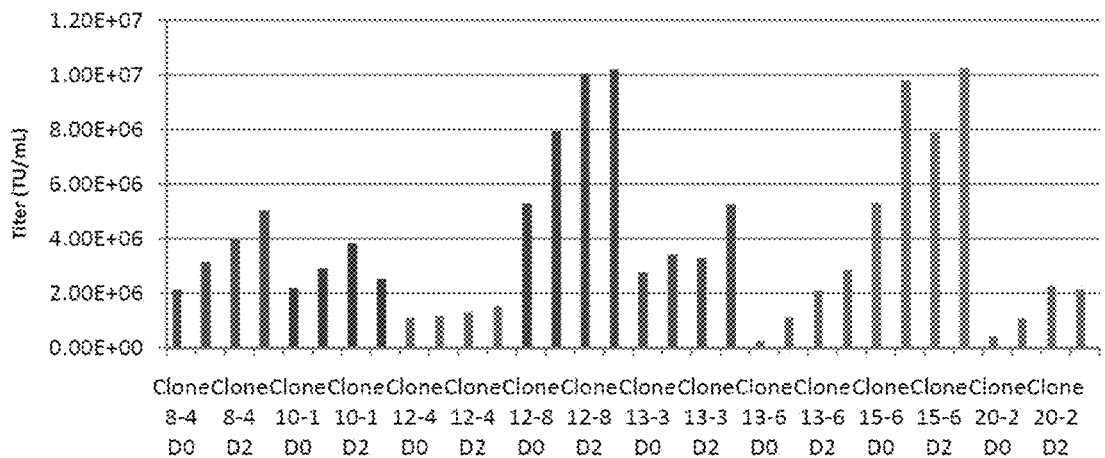
FIG. 12 shows daily titers from HT1080+T5.0002 clonal candidates for titer production from confluent cultures.

Vector stability was assessed by measuring the vector's ability to infect a naïve cell type under various dilutions and test the ability to convert 5-flurocytisine (5-FC) to 5-flurouracil (5-FU) from the transfer of the cytosine deaminase gene from the viral vector to the naïve infected cell. The conversion of 5-FC to 5-FU is quantitated by HPLC with the raw data processed utilizing a non-linear regression of the transformed dilution values. Both doses (undiluted and 1/100 diluted samples) from Lot T003-002-40L show no decrease in transfer of expression capability when stored at ≤−65° C. for up to 12 months. Both T003-002-40L (undiluted) and M100-09 generated a dose curve comparable to the current reference Vector. M101-09 generated the expected curve at 1/10 of the undiluted vector (M100-09). T003-002-40L (1/100) and M102-09 generated the expected curve at 1/100 of their undiluted vector, respectively. FIGS. 10 and 11 show the 5-FC conversion dose response for lots T003-002-40L (FIG. 10) and GMP lots (FIG. 11) at the last time point tested.

TCID50 Assay on Vector Lots.

Vector stability was assessed by measuring the vector's ability to infect a naïve cell type by calculating the infectious dose at which 50% of the cells would be infected under tissue culture conditions (TCID50). The method used to determine if a cell was infected was determined by PCR detection. In this evaluation, no observed decrease in infectivity was observed based on the TCID50 when stored at ≤−65° C. for up to 12 months for all lots tested within the current variability of the assay (% CV of Reference Vector over 8 assays was 45%). Tables 13 and 14 show the measured TCID50/mL value for the lot T003-002-40L (Table 7) and GMP lots (Table 8).

TABLE 7

TCID$_{50}$ of Lot T003-002-40L (Undiluted and $^1\!/_{100}$) at Release, 3 and 12 months at ≤−65° C.

| T003-002-40L | Release | 3 M | 12 M |
|---|---|---|---|
| | | TCID$_{50}$/mL | |
| Undiluted | 2.0E+08 | 9.0E+07 | 2.00E+08 |
| $^1\!/_{100}$ | 1.3E+06 | 6.5E+05 | 7.95E+05 |

TABLE 8

TCID$_{50}$ of GMP Lots M100-09 (High Dose), M101-09 (Mid Dose) and M102-09 (Low Dose) at Release, 3 and 6 months at ≤−65° C.

| | Release | 3 M | 6 M | 1X F/T* |
|---|---|---|---|---|
| | | TCID$_{50}$/mL | | |
| M100-09 | 5.0E+07 | 5.0E+07 | 7.9E+07 | 5.01E+07 |
| M101-09 | 7.9E+06 | 1.3E+06 | 1.3E+07 | 1.26E+07 |
| M102-09 | 5.0E+05 | 5.0E+05 | 7.9E+05 | 5.01E+05 |

*Vials were thawed at the 3 M timepoint, re-frozen at ≤−65° C. and tested with the 6 M samples.

Based on the above stability data, purified replication competent MLV viral vector produced from a stably infected HT-1080 cells are more stable than the identical vector produced by transient transfection when stored at temperatures of ≤−65° C.

Example 13: T5.0002 Vector Made from an HT1080clone and Produced from Suspension Serum Free Cultures is as Potent as Vector Made from the Adherent HT1080+T5.0002 Line in Medium with Fetal Calf Serum, in a Mouse Tumor Model Vector was prepared from one of the serum free suspension clones and from the HT1080+T5.0002 cell line, and purified and processed as described in example 6.

In separate experiments these vector preparations were used to treat a mouse glioma tumor model—Tu2449 in B6C3F1 mice (H M. Smilowitz J Neurosurg 106:652-659, 2007), Mice were implanted intracranially with the tumor and four days later ascending doses of vector (10^4, 10^5 Tu/g brain) were administered to cohorts of 10 animals for both vector preparations. At day 13 5-FC dosing was carried by twice daily ip injections (500 mg/kg BID) for four days, and the 5-FC treatment then carried out non a schedule of 10 days off 4 days on. Kaplan-Meyer plots showed that the survival with the material from the cloned line was at least as good as that from the HT1080+T5.0002 line. Both showed 80-90 survival in the 10^5 Tu groups past day 100 while controls had amedian survival of around 30 days.

Example 14: Use of Purified Vector Encoding Mouse Gamma Interferon as a Therapy in a Syngeneic Mouse Cancer Model The objective of this study was to assess the effectiveness Toca 511 (encoding yCD2) and Toca 621 (encoding mouse gamma interferon) in the S91/BALB/c model by evaluating the spread of novel MLV based retroviral vectors in mouse S91 subcutaneous (subQ) tumors in immunocompetent BALB/c mice. Vector was prepared from: 1) HT108+T5.0002 (Toca 511) and is a preparation of a replication-competent retroviral vector carrying the optimized cytosine deaminase gene; 2) HT1080+mIFN a stable producer line of Toca 621, a replication-competent retroviral vector carrying the interferon gamma gene; and 3) HT1080+T5.0006 (GFP Vector) m, were each delivered via intra-tumoral injection (IT).

Mice.

Female BALB/c mice (age ~8 weeks) were purchased from Jackson Laboratories. Mice were acclimated for 7 days after arrival.

Tumor Cells.

S91 Cloudman cells (ATCC, Manassas Va.) derived from Clone M-3, a melanin-producing cell line was adapted to cell culture by Y. Yasumura, A. H. Tashjian and G. Sato from a Cloudman S91 melanoma in a (C×DBA) F1 male mouse. Cells were cultured in Dulbecco's modified Eagles medium with 10% fetal bovine serum, sodium pyruvate, and Glutamax (Hyclone, Logan Utah, and Invitrogen, San Diego Calif.). Cells were resuspended in PBS (Hyclone, Logan Utah) for implantation. 591 were injected 1E5 in 200 µL IV and 1E5 in 100 µL SQ.

Four groups of female BALB/c mice (65 mice, ~8 weeks of age) were implanted subQ at their right flank with S91 tumor cells. After the tumors were allowed to grow until they reached approximately 50-125 mm$^3$, 3 mice were dosed IT with PBS (Group 1), 10 mice were injected IT with Toca 511 4.7E8/ml (Group 2), 5 mice were injected IT with Toca 621 2.8E8/ml (Group 3), and 6 mice were injected IT with GFP (Group 4) within days 15-19.

| Group Assignments | | |
|---|---|---|
| Group | Treatment | N |
| 1 | Control: PBS | 2 |
| 2 | Toca 511 | 10 |
| 3 | Toca 621 | 5 |
| 4 | GFP Vector | 6 |
| Total Number of Animals | | 23 |

Vector.

Toca 511 and Toca 621 (50 µL) was injected slowly intratumorally using an insulin syringe.

Toca 511 (encoding the yCD2 cytosine deaminase gene) lot number T511019-FNL was used for all Group 2 animals, and Toca 621 (encoding mouse Interferon Gamma) lot number T621006 SEC was used for all Group 3 animals. This material was produced using the same process used for clinical trial material but it was not made in accordance with cGMP.

Toca 511 lot number T511019-FNL has a titer of 4.7E8 TU/mL.

Toca 621 lot number T621006 SEC has a titer of 2.8E8 TU/mL.

MLV-GFP (T5.0006) is lot number TGFP004-FNL with a titer of 9.0E7 TU/mL.

Figure 15:
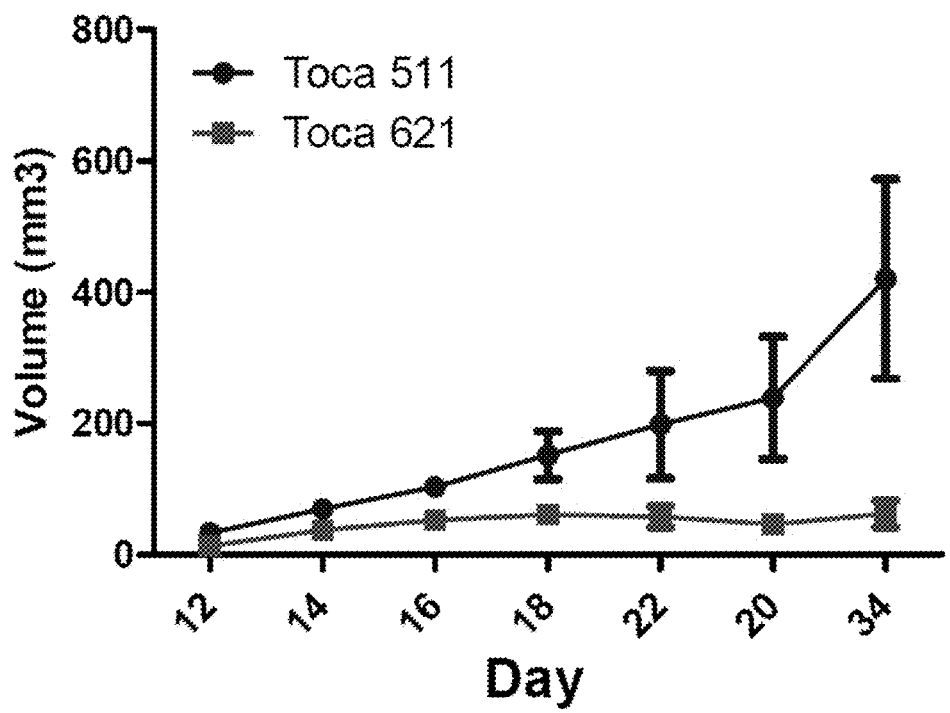
FIG. 15 shows analyses of Toca 511 and Toca 621 transduction on the growth kinetics of S91 subQ tumor cells. S91 Tumors were injected with vector 10 days after implantation.

Tumors injected with Toca 621 showed a (p=0.0016) decrease in tumor growth compared to tumors injected with Toca 511 (FIG. 15). One animal from Toca 621 injection cleared the tumor. Further analysis showed that genomes could be detected in some of the Toca 511 and Toca 621 tumors up to 24 days after injection. One of two explants from Toca 621 injected tumors had detectable secretion of IFNγ (18.8 pg/mL) by ELISA.

Example 15 Rate of GFP Viral Spread in a U-87 Subcutaneous Xenograft Model in Nude Mice, Using GFP Vector from a Stable Producer Line To determine the rate of viral spread based on a single administration of vector 3e5/100 µL into established U-87 xenografts, by determining the percentage of GFP expressing cells at various time points, in a subcutaneous model of a tumor in nude mice.

Figure 16:
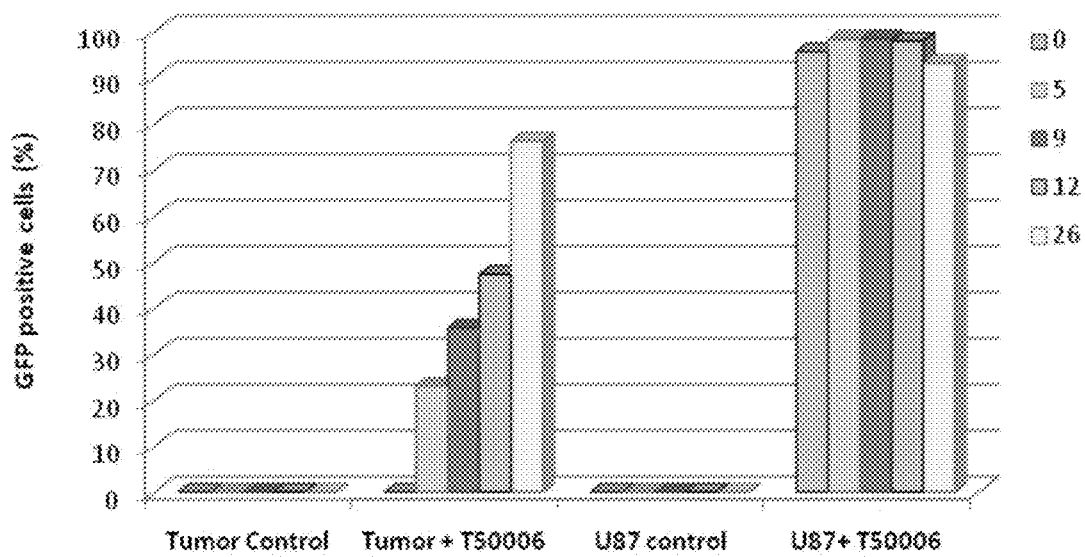
FIG. 16 shows spread of purified T5.0006 (GFP vector) made in a stable producer line through U87 subcutaneous tumors in nude mice, over time (0, 5, 9, 12, 26 days).

Study Description:

a total of 5 mice (ID #71 to #75) underwent right and left dorsal flank implantation of 2e6 U-87 cells administered S.Q on day 0. At day 13 the right dorsal tumor of each mouse was injected with purified T50006 (GFP vector) 3×10^5 TU/100 µL made from an HT1080 producer pool constructed as described above, and purified as described in example YYY. At the same day the animal ID #71 was sacrificed; animals ID #72, ID #73, ID #74 and ID #75 were sacrificed at days 5, 9, 12 and 26 after vector inoculation, respectively. Tumors were removed and processed for FACS analysis of GFP. Results are shown in FIG. 16 and show a steady increase in the % GFP positive cells over time, indicating vector spread in this model.

What is claimed is:

1. A replication competent retrovirus particle produced by a retrovirus producing HT1080 cell line, wherein said HT1080 cell line stably express a recombinant retroviral genome comprising a gag gene, pol gene, env gene, a heterologous polynucleotide, and retroviral psi (Ψ) factor for the assembly of the recombinant retroviral genome, wherein the replication competent retrovirus particle comprises the recombinant retroviral genome, and wherein the HT1080 cell line has been adapted to be grown and continuously passaged in serum free media and in suspension.

2. The replication competent retrovirus particle of claim 1,
wherein the replication competent retrovirus comprises:
a retroviral GAG protein;
a retroviral POL protein;
a retroviral envelope;
a retroviral polynucleotide comprising Long-Terminal Repeat (LTR) sequences at the 3' end of the retroviral polynucleotide sequence, a gag nucleic acid domain, a pol nucleic acid domain and an env nucleic acid domain;
a cassette comprising an internal ribosome entry site (IRES) or a nucleic acid regulatory domain operably linked to a heterologous polynucleotide, wherein the cassette is positioned 5' to the 3' LTR and 3' to the env nucleic acid domain encoding the retroviral envelope; and
cis-acting sequences necessary for reverse transcription, packaging and integration in a target cell.

3. The replication competent retrovirus particle of claim 2, wherein the retroviral polynucleotide sequence is from murine leukemia virus (MLV), Moloney murine leukemia virus (MoMLV), Gibbon ape leukemia virus (GALV), murine mammary tumor virus (MuMTV), Rous Sarcoma Virus (RSV), baboon endogenous virus (BEV), or feline virus RD114.

4. The replication competent retrovirus particle of claim 3, wherein the MLV is an amphotropic MLV.

5. The replication competent retrovirus particle of claim 1, wherein the retrovirus is a gammaretrovirus.

6. The replication competent retrovirus particle of claim 2, wherein the nucleic acid regulatory domain is a pol III regulatory domain.

7. The replication competent retrovirus particle of claim 1, wherein the heterologous polynucleotide encodes a protein binding domain.

8. The replication competent retrovirus particle of claim 7, wherein the protein binding domain is an antibody, antibody fragment, antibody domain or receptor ligand.

9. The replication competent retrovirus particle of claim 1, wherein the heterologous polynucleotide encodes a polypeptide that converts a nontoxic prodrug in to a toxic drug.

10. The replication competent retrovirus particle of claim 9, wherein the polypeptide that converts a nontoxic prodrug in to a toxic drug is thymidine kinase, purine nucleoside phosphorylase (PNP), or cytosine deaminase.

11. The replication competent retrovirus particle of claim 6, wherein the heterologous nucleic acid sequence comprises an inhibitory polynucleotide.

12. The replication competent retrovirus particle of claim 11, wherein the inhibitory polynucleotide comprises an RNAi or siRNA sequence and wherein the regulatory nucleic acid domain is a promoter.

* * * * *

SEQUENCE LISTING

<160> NUMBER OF SEQ ID NOS: 30

<210> SEQ ID NO 1
<211> LENGTH: 477
<212> TYPE: DNA
<213> ORGANISM: Saccharomyces cerevisiae
<220> FEATURE:
<221> NAME/KEY: CDS
<222> LOCATION: (1)..(477)

<400> SEQUENCE: 1

```
atg gtg aca ggg gga atg gca agc aag tgg gat cag aag ggt atg gac      48
Met Val Thr Gly Gly Met Ala Ser Lys Trp Asp Gln Lys Gly Met Asp
1               5                   10                  15 att gcc tat gag gag gcg gcc tta ggt tac aaa gag ggt ggt gtt cct      96
Ile Ala Tyr Glu Glu Ala Ala Leu Gly Tyr Lys Glu Gly Gly Val Pro
            20                  25                  30 att ggc gga tgt ctt atc aat aac aaa gac gga agt gtt ctc ggt cgt     144
Ile Gly Gly Cys Leu Ile Asn Asn Lys Asp Gly Ser Val Leu Gly Arg
        35                  40                  45 ggt cac aac atg aga ttt caa aag gga tcc gcc aca cta cat ggt gag     192
Gly His Asn Met Arg Phe Gln Lys Gly Ser Ala Thr Leu His Gly Glu
    50                  55                  60 atc tcc act ttg gaa aac tgt ggg aga tta gag ggc aaa gtg tac aaa     240
Ile Ser Thr Leu Glu Asn Cys Gly Arg Leu Glu Gly Lys Val Tyr Lys
65                  70                  75                  80 gat acc act ttg tat acg acg ctg tct cca tgc gac atg tgt aca ggt     288
Asp Thr Thr Leu Tyr Thr Thr Leu Ser Pro Cys Asp Met Cys Thr Gly
                85                  90                  95 gcc atc atc atg tat ggt att cca cgc tgt gtt gtc ggt gag aac gtt     336
Ala Ile Ile Met Tyr Gly Ile Pro Arg Cys Val Val Gly Glu Asn Val
            100                 105                 110 aat ttc aaa agt aag ggc gag aaa tat tta caa act aga ggt cac gag     384
Asn Phe Lys Ser Lys Gly Glu Lys Tyr Leu Gln Thr Arg Gly His Glu
        115                 120                 125 gtt gtt gtt gtt gac gat gag agg tgt aaa aag atc atg aaa caa ttt     432
Val Val Val Val Asp Asp Glu Arg Cys Lys Lys Ile Met Lys Gln Phe
    130                 135                 140 atc gat gaa aga cct cag gat tgg ttt gaa gat att ggt gag tag         477
Ile Asp Glu Arg Pro Gln Asp Trp Phe Glu Asp Ile Gly Glu
145                 150                 155
```

<210> SEQ ID NO 2
<211> LENGTH: 158
<212> TYPE: PRT
<213> ORGANISM: Saccharomyces cerevisiae

<400> SEQUENCE: 2

```
Met Val Thr Gly Gly Met Ala Ser Lys Trp Asp Gln Lys Gly Met Asp
1               5                   10                  15
```

```
Ile Ala Tyr Glu Glu Ala Leu Gly Tyr Lys Glu Gly Gly Val Pro
         20                  25                  30

Ile Gly Gly Cys Leu Ile Asn Asn Lys Asp Gly Ser Val Leu Gly Arg
     35                  40                  45

Gly His Asn Met Arg Phe Gln Lys Gly Ser Ala Thr Leu His Gly Glu
 50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                 85                  90                  95

Ala Ile Ile Met Tyr Gly Ile Pro Arg Cys Val Val Gly Glu Asn Val
                100                 105                 110

Asn Phe Lys Ser Lys Gly Glu Lys Tyr Leu Gln Thr Arg Gly His Glu
             115                 120                 125

Val Val Val Val Asp Asp Glu Arg Cys Lys Lys Ile Met Lys Gln Phe
130                 135                 140

Ile Asp Glu Arg Pro Gln Asp Trp Phe Glu Asp Ile Gly Glu
145                 150                 155
```

```
<210> SEQ ID NO 3
<211> LENGTH: 477
<212> TYPE: DNA
<213> ORGANISM: Artificial Sequence
<220> FEATURE:
<223> OTHER INFORMATION: Engineered cytosine deaminase
<220> FEATURE:
<221> NAME/KEY: CDS
<222> LOCATION: (1)..(477)

<400> SEQUENCE: 3
```

```
atg gtg aca ggg gga atg gca agc aag tgg gat cag aag ggt atg gac      48
Met Val Thr Gly Gly Met Ala Ser Lys Trp Asp Gln Lys Gly Met Asp
1               5                   10                  15 att gcc tat gag gag gcg tta tta ggt tac aaa gag ggt ggt gtt cct      96
Ile Ala Tyr Glu Glu Ala Leu Leu Gly Tyr Lys Glu Gly Gly Val Pro
             20                  25                  30 att ggc gga tgt ctt atc aat aac aaa gac gga agt gtt ctc ggt cgt     144
Ile Gly Gly Cys Leu Ile Asn Asn Lys Asp Gly Ser Val Leu Gly Arg
         35                  40                  45 ggt cac aac atg aga ttt caa aag gga tcc gcc aca cta cat ggt gag     192
Gly His Asn Met Arg Phe Gln Lys Gly Ser Ala Thr Leu His Gly Glu
 50                  55                  60 atc tcc act ttg gaa aac tgt ggg aga tta gag ggc aaa gtg tac aaa     240
Ile Ser Thr Leu Glu Asn Cys Gly Arg Leu Glu Gly Lys Val Tyr Lys
65                  70                  75                  80 gat acc act ttg tat acg acg ctg tct cca tgc gac atg tgt aca ggt     288
Asp Thr Thr Leu Tyr Thr Thr Leu Ser Pro Cys Asp Met Cys Thr Gly
                 85                  90                  95 gcc atc atc atg tat ggt att cca cgc tgt gtc atc ggt gag aac gtt     336
Ala Ile Ile Met Tyr Gly Ile Pro Arg Cys Val Ile Gly Glu Asn Val
                100                 105                 110 aat ttc aaa agt aag ggc gag aaa tat tta caa act aga ggt cac gag     384
Asn Phe Lys Ser Lys Gly Glu Lys Tyr Leu Gln Thr Arg Gly His Glu
             115                 120                 125 gtt gtt gtt gtt gac gat gag agg tgt aaa aag tta atg aaa caa ttt     432
Val Val Val Val Asp Asp Glu Arg Cys Lys Lys Leu Met Lys Gln Phe
130                 135                 140 atc gat gaa aga cct cag gat tgg ttt gaa gat att ggt gag tag         477
Ile Asp Glu Arg Pro Gln Asp Trp Phe Glu Asp Ile Gly Glu
```

<210> SEQ ID NO 4
<211> LENGTH: 158
<212> TYPE: PRT
<213> ORGANISM: Artificial Sequence
<220> FEATURE:
<223> OTHER INFORMATION: Synthetic Construct

<400> SEQUENCE: 4

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu
145                 150                 155

<210> SEQ ID NO 5
<211> LENGTH: 480
<212> TYPE: DNA
<213> ORGANISM: Artificial Sequence
<220> FEATURE:
<223> OTHER INFORMATION: Human codon optimized cytosine deaminase
<220> FEATURE:
<221> NAME/KEY: CDS
<222> LOCATION: (1)..(480)

<400> SEQUENCE: 5 atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15 atc gct tac gag gag gcc gca ctg ggc tac aag gag ggc ggc gtg cct       96
Ile Ala Tyr Glu Glu Ala Ala Leu Gly Tyr Lys Glu Gly Gly Val Pro
            20                  25                  30 atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45 ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60 atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

| gct atc atc atg tac ggc atc cct agg tgt gtg gtc ggc gag aac gtg | 336 |
| Ala Ile Ile Met Tyr Gly Ile Pro Arg Cys Val Val Gly Glu Asn Val | |
| 100 105 110 | |

| aac ttc aag tcc aag ggc gag aag tac ctg caa acc agg ggc cac gag | 384 |
| Asn Phe Lys Ser Lys Gly Glu Lys Tyr Leu Gln Thr Arg Gly His Glu | |
| 115 120 125 | |

| gtg gtg gtt gtt gac gat gag agg tgt aag aag atc atg aag cag ttc | 432 |
| Val Val Val Val Asp Asp Glu Arg Cys Lys Lys Ile Met Lys Gln Phe | |
| 130 135 140 | |

| atc gac gag agg cct cag gac tgg ttc gag gat atc ggc gag tga taa | 480 |
| Ile Asp Glu Arg Pro Gln Asp Trp Phe Glu Asp Ile Gly Glu | |
| 145 150 155 | |

<210> SEQ ID NO 6
<211> LENGTH: 158
<212> TYPE: PRT
<213> ORGANISM: Artificial Sequence
<220> FEATURE:
<223> OTHER INFORMATION: Synthetic Construct

<400> SEQUENCE: 6

Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155

<210> SEQ ID NO 7
<211> LENGTH: 756
<212> TYPE: DNA
<213> ORGANISM: Saccharomyces cerevisiae
<220> FEATURE:
<221> NAME/KEY: CDS
<222> LOCATION: (1)..(756)

<400> SEQUENCE: 7

| atg aac ccg tta ttc ttt ttg gct tct cca ttc ttg tac ctt aca tat | 48 |
| Met Asn Pro Leu Phe Phe Leu Ala Ser Pro Phe Leu Tyr Leu Thr Tyr | |
| 1               5                   10                  15 | |

| ctt ata tat tat cca aac aaa ggg tct ttc gtt agc aaa cct aga aat | 96 |
| Leu Ile Tyr Tyr Pro Asn Lys Gly Ser Phe Val Ser Lys Pro Arg Asn | |
| 20                  25                  30 | |

| ctg caa aaa atg tct tcg gaa cca ttt aag aac gtc tac ttg cta cct | 144 |
| Leu Gln Lys Met Ser Ser Glu Pro Phe Lys Asn Val Tyr Leu Leu Pro | |
| 35                  40                  45 | |

```
caa aca aac caa ttg ctg ggt ttg tac acc atc atc aga aat aag aat       192
Gln Thr Asn Gln Leu Leu Gly Leu Tyr Thr Ile Ile Arg Asn Lys Asn
        50                  55                  60 aca act aga cct gat ttc att ttc tac tcc gat aga atc atc aga ttg       240
Thr Thr Arg Pro Asp Phe Ile Phe Tyr Ser Asp Arg Ile Ile Arg Leu
 65                  70                  75                  80 ttg gtt gaa gaa ggt ttg aac cat cta cct gtg caa aag caa att gtg       288
Leu Val Glu Glu Gly Leu Asn His Leu Pro Val Gln Lys Gln Ile Val
                    85                  90                  95 gaa act gac acc aac gaa aac ttc gaa ggt gtc tca ttc atg ggt aaa       336
Glu Thr Asp Thr Asn Glu Asn Phe Glu Gly Val Ser Phe Met Gly Lys
                100                 105                 110 atc tgt ggt gtt tcc att gtc aga gct ggt gaa tcg atg gag caa gga       384
Ile Cys Gly Val Ser Ile Val Arg Ala Gly Glu Ser Met Glu Gln Gly
            115                 120                 125 tta aga gac tgt tgt agg tct gtg cgt atc ggt aaa att tta att caa       432
Leu Arg Asp Cys Cys Arg Ser Val Arg Ile Gly Lys Ile Leu Ile Gln
        130                 135                 140 agg gac gag gag act gct tta cca aag tta ttc tac gaa aaa tta cca       480
Arg Asp Glu Glu Thr Ala Leu Pro Lys Leu Phe Tyr Glu Lys Leu Pro
145                 150                 155                 160 gag gat ata tct gaa agg tat gtc ttc cta tta gac cca atg ctg gcc       528
Glu Asp Ile Ser Glu Arg Tyr Val Phe Leu Leu Asp Pro Met Leu Ala
                165                 170                 175 acc ggt ggt agt gct atc atg gct aca gaa gtc ttg att aag aga ggt       576
Thr Gly Gly Ser Ala Ile Met Ala Thr Glu Val Leu Ile Lys Arg Gly
                180                 185                 190 gtt aag cca gag aga att tac ttc tta aac cta atc tgt agt aag gaa       624
Val Lys Pro Glu Arg Ile Tyr Phe Leu Asn Leu Ile Cys Ser Lys Glu
            195                 200                 205 ggg att gaa aaa tac cat gcc gcc ttc cca gag gtc aga att gtt act       672
Gly Ile Glu Lys Tyr His Ala Ala Phe Pro Glu Val Arg Ile Val Thr
        210                 215                 220 ggt gcc ctc gac aga ggt cta gat gaa aac aag tat cta gtt cca ggg       720
Gly Ala Leu Asp Arg Gly Leu Asp Glu Asn Lys Tyr Leu Val Pro Gly
225                 230                 235                 240 ttg ggt gac ttt ggt gac aga tac tac tgt gtt taa                       756
Leu Gly Asp Phe Gly Asp Arg Tyr Tyr Cys Val
                245                 250

<210> SEQ ID NO 8
<211> LENGTH: 251
<212> TYPE: PRT
<213> ORGANISM: Saccharomyces cerevisiae

<400> SEQUENCE: 8

Met Asn Pro Leu Phe Phe Leu Ala Ser Pro Phe Leu Tyr Leu Thr Tyr
1               5                   10                  15

Leu Ile Tyr Tyr Pro Asn Lys Gly Ser Phe Val Ser Lys Pro Arg Asn
            20                  25                  30

Leu Gln Lys Met Ser Ser Glu Pro Phe Lys Asn Val Tyr Leu Leu Pro
        35                  40                  45

Gln Thr Asn Gln Leu Leu Gly Leu Tyr Thr Ile Ile Arg Asn Lys Asn
    50                  55                  60

Thr Thr Arg Pro Asp Phe Ile Phe Tyr Ser Asp Arg Ile Ile Arg Leu
65                  70                  75                  80

Leu Val Glu Glu Gly Leu Asn His Leu Pro Val Gln Lys Gln Ile Val
                85                  90                  95

Glu Thr Asp Thr Asn Glu Asn Phe Glu Gly Val Ser Phe Met Gly Lys
```

```
            100                 105                 110
Ile Cys Gly Val Ser Ile Val Arg Ala Gly Glu Ser Met Glu Gln Gly
                115                 120                 125

Leu Arg Asp Cys Cys Arg Ser Val Arg Ile Gly Lys Ile Leu Ile Gln
            130                 135                 140

Arg Asp Glu Glu Thr Ala Leu Pro Lys Leu Phe Tyr Glu Lys Leu Pro
145                 150                 155                 160

Glu Asp Ile Ser Glu Arg Tyr Val Phe Leu Leu Asp Pro Met Leu Ala
                165                 170                 175

Thr Gly Gly Ser Ala Ile Met Ala Thr Glu Val Leu Ile Lys Arg Gly
            180                 185                 190

Val Lys Pro Glu Arg Ile Tyr Phe Leu Asn Leu Ile Cys Ser Lys Glu
        195                 200                 205

Gly Ile Glu Lys Tyr His Ala Ala Phe Pro Glu Val Arg Ile Val Thr
    210                 215                 220

Gly Ala Leu Asp Arg Gly Leu Asp Glu Asn Lys Tyr Leu Val Pro Gly
225                 230                 235                 240

Leu Gly Asp Phe Gly Asp Arg Tyr Tyr Cys Val
                245                 250

<210> SEQ ID NO 9
<211> LENGTH: 1443
<212> TYPE: DNA
<213> ORGANISM: homo sapiens
<220> FEATURE:
<221> NAME/KEY: CDS
<222> LOCATION: (1)..(1443)

<400> SEQUENCE: 9
```

| | | | | | | | | | | | | | | | | |
|---|---|---|---|---|---|---|---|---|---|---|---|---|---|---|---|---|
| atg | gct | gtt | gct | cgt | gct | gct | ctt | ggt | cct | ctt | gtt | act | ggt | ctt | tat | 48 |
| Met | Ala | Val | Ala | Arg | Ala | Ala | Leu | Gly | Pro | Leu | Val | Thr | Gly | Leu | Tyr | |
| 1 | | | | 5 | | | | | 10 | | | | | 15 | | |
| gat | gtt | caa | gct | ttt | aaa | ttt | ggt | gat | ttt | gtt | ctt | aaa | tct | ggt | ctt | 96 |
| Asp | Val | Gln | Ala | Phe | Lys | Phe | Gly | Asp | Phe | Val | Leu | Lys | Ser | Gly | Leu | |
| | | | 20 | | | | | 25 | | | | | 30 | | | |
| tct | tct | cct | att | tat | att | gat | ctt | cgt | ggt | att | gtt | tct | cgt | cct | cgt | 144 |
| Ser | Ser | Pro | Ile | Tyr | Ile | Asp | Leu | Arg | Gly | Ile | Val | Ser | Arg | Pro | Arg | |
| | | 35 | | | | | 40 | | | | | 45 | | | | |
| ctt | ctt | tct | caa | gtt | gct | gat | att | ctt | ttt | caa | act | gct | caa | aat | gct | 192 |
| Leu | Leu | Ser | Gln | Val | Ala | Asp | Ile | Leu | Phe | Gln | Thr | Ala | Gln | Asn | Ala | |
| | 50 | | | | | 55 | | | | | 60 | | | | | |
| ggt | att | tct | ttt | gat | act | gtt | tgt | ggt | gtt | cct | tat | act | gct | ctt | cct | 240 |
| Gly | Ile | Ser | Phe | Asp | Thr | Val | Cys | Gly | Val | Pro | Tyr | Thr | Ala | Leu | Pro | |
| 65 | | | | | 70 | | | | | 75 | | | | | 80 | |
| ctt | gct | act | gtt | att | tgt | tct | act | aat | caa | att | cct | atg | ctt | att | cgt | 288 |
| Leu | Ala | Thr | Val | Ile | Cys | Ser | Thr | Asn | Gln | Ile | Pro | Met | Leu | Ile | Arg | |
| | | | | 85 | | | | | 90 | | | | | 95 | | |
| cgt | aaa | gaa | act | aaa | gat | tat | ggt | act | aaa | cgt | ctt | gtt | gaa | ggt | act | 336 |
| Arg | Lys | Glu | Thr | Lys | Asp | Tyr | Gly | Thr | Lys | Arg | Leu | Val | Glu | Gly | Thr | |
| | | | 100 | | | | | 105 | | | | | 110 | | | |
| att | aat | cct | ggt | gaa | act | tgt | ctt | att | att | gaa | gat | gtt | gtt | act | tct | 384 |
| Ile | Asn | Pro | Gly | Glu | Thr | Cys | Leu | Ile | Ile | Glu | Asp | Val | Val | Thr | Ser | |
| | | 115 | | | | | 120 | | | | | 125 | | | | |
| ggt | tct | tct | gtt | ctt | gaa | act | gtt | gaa | gtt | ctt | caa | aaa | gaa | ggt | ctt | 432 |
| Gly | Ser | Ser | Val | Leu | Glu | Thr | Val | Glu | Val | Leu | Gln | Lys | Glu | Gly | Leu | |
| | 130 | | | | | 135 | | | | | 140 | | | | | |
| aaa | gtt | act | gat | gct | att | gtt | ctt | ctt | gat | cgt | gaa | caa | ggt | ggt | aaa | 480 |
| Lys | Val | Thr | Asp | Ala | Ile | Val | Leu | Leu | Asp | Arg | Glu | Gln | Gly | Gly | Lys | |
| 145 | | | | | 150 | | | | | 155 | | | | | 160 | |

| | | | | | | | | | | | | | | | |
|---|---|---|---|---|---|---|---|---|---|---|---|---|---|---|---|
| gat | aaa | ctt | caa | gct | cat | ggt | att | cgt | ctt | cat | tct | gtt | tgt | act | ctt | 528 |
| Asp | Lys | Leu | Gln | Ala | His | Gly | Ile | Arg | Leu | His | Ser | Val | Cys | Thr | Leu |
| | | | 165 | | | | 170 | | | | 175 | | | | |

| tct | aaa | atg | ctt | gaa | att | ctt | gaa | caa | caa | aaa | aaa | gtt | gat | gct | gaa | 576 |
| Ser | Lys | Met | Leu | Glu | Ile | Leu | Glu | Gln | Gln | Lys | Lys | Val | Asp | Ala | Glu |
| | | 180 | | | | | 185 | | | | | 190 | | | |

| act | gtt | ggt | cgt | gtt | aaa | cgt | ttt | att | caa | gaa | aat | gtt | ttt | gtt | gct | 624 |
| Thr | Val | Gly | Arg | Val | Lys | Arg | Phe | Ile | Gln | Glu | Asn | Val | Phe | Val | Ala |
| | | | 195 | | | | 200 | | | | 205 | | | | |

| gct | aat | cat | aat | ggt | tct | cct | ctt | tct | att | aaa | gaa | gct | cct | aaa | gaa | 672 |
| Ala | Asn | His | Asn | Gly | Ser | Pro | Leu | Ser | Ile | Lys | Glu | Ala | Pro | Lys | Glu |
| | 210 | | | | | 215 | | | | | 220 | | | | |

| ctt | tct | ttt | ggt | gct | cgt | gct | gaa | ctt | cct | cgt | att | cat | cct | gtt | gct | 720 |
| Leu | Ser | Phe | Gly | Ala | Arg | Ala | Glu | Leu | Pro | Arg | Ile | His | Pro | Val | Ala |
| 225 | | | | | 230 | | | | | 235 | | | | | 240 |

| tct | aaa | ctt | ctt | cgt | ctt | atg | caa | aaa | aaa | gaa | act | aat | ctt | tgt | ctt | 768 |
| Ser | Lys | Leu | Leu | Arg | Leu | Met | Gln | Lys | Lys | Glu | Thr | Asn | Leu | Cys | Leu |
| | | | | 245 | | | | | 250 | | | | | 255 | |

| tct | gct | gat | gtt | tct | ctt | gct | cgt | gaa | ctt | ctt | caa | ctt | gct | gat | gct | 816 |
| Ser | Ala | Asp | Val | Ser | Leu | Ala | Arg | Glu | Leu | Leu | Gln | Leu | Ala | Asp | Ala |
| | | | 260 | | | | | 265 | | | | | 270 | | |

| ctt | ggt | cct | tct | att | tgt | atg | ctt | aaa | act | cat | gtt | gat | att | ctt | aat | 864 |
| Leu | Gly | Pro | Ser | Ile | Cys | Met | Leu | Lys | Thr | His | Val | Asp | Ile | Leu | Asn |
| | | 275 | | | | | 280 | | | | | 285 | | | |

| gat | ttt | act | ctt | gat | gtt | atg | aaa | gaa | ctt | att | act | ctt | gct | aaa | tgt | 912 |
| Asp | Phe | Thr | Leu | Asp | Val | Met | Lys | Glu | Leu | Ile | Thr | Leu | Ala | Lys | Cys |
| | 290 | | | | | 295 | | | | | 300 | | | | |

| cat | gaa | ttt | ctt | att | ttt | gaa | gat | cgt | aaa | ttt | gct | gat | att | ggt | aat | 960 |
| His | Glu | Phe | Leu | Ile | Phe | Glu | Asp | Arg | Lys | Phe | Ala | Asp | Ile | Gly | Asn |
| 305 | | | | | 310 | | | | | 315 | | | | | 320 |

| act | gtt | aaa | aaa | caa | tat | gaa | ggt | ggt | att | ttt | aaa | att | gct | tct | tgg | 1008 |
| Thr | Val | Lys | Lys | Gln | Tyr | Glu | Gly | Gly | Ile | Phe | Lys | Ile | Ala | Ser | Trp |
| | | | | 325 | | | | | 330 | | | | | 335 | |

| gct | gat | ctt | gtt | aat | gct | cat | gtt | gtt | cct | ggt | tct | ggt | gtt | gtt | aaa | 1056 |
| Ala | Asp | Leu | Val | Asn | Ala | His | Val | Val | Pro | Gly | Ser | Gly | Val | Val | Lys |
| | | | 340 | | | | | 345 | | | | | 350 | | |

| ggt | ctt | caa | gaa | gtt | ggt | ctt | cct | ctt | cat | cgt | ggt | tgt | ctt | ctt | att | 1104 |
| Gly | Leu | Gln | Glu | Val | Gly | Leu | Pro | Leu | His | Arg | Gly | Cys | Leu | Leu | Ile |
| | | 355 | | | | | 360 | | | | | 365 | | | |

| gct | gaa | atg | tct | tct | act | ggt | tct | ctt | gct | act | ggt | gat | tat | act | cgt | 1152 |
| Ala | Glu | Met | Ser | Ser | Thr | Gly | Ser | Leu | Ala | Thr | Gly | Asp | Tyr | Thr | Arg |
| | 370 | | | | | 375 | | | | | 380 | | | | |

| gct | gct | gtt | cgt | atg | gct | gaa | gaa | cat | tct | gaa | ttt | gtt | gtt | ggt | ttt | 1200 |
| Ala | Ala | Val | Arg | Met | Ala | Glu | Glu | His | Ser | Glu | Phe | Val | Val | Gly | Phe |
| 385 | | | | | 390 | | | | | 395 | | | | | 400 |

| att | tct | ggt | tct | cgt | gtt | tct | atg | aaa | cct | gaa | ttt | ctt | cat | ctt | act | 1248 |
| Ile | Ser | Gly | Ser | Arg | Val | Ser | Met | Lys | Pro | Glu | Phe | Leu | His | Leu | Thr |
| | | | | 405 | | | | | 410 | | | | | 415 | |

| cct | ggt | gtt | caa | ctt | gaa | gct | ggt | ggt | gat | aat | ctt | ggt | caa | caa | tat | 1296 |
| Pro | Gly | Val | Gln | Leu | Glu | Ala | Gly | Gly | Asp | Asn | Leu | Gly | Gln | Gln | Tyr |
| | | | 420 | | | | | 425 | | | | | 430 | | |

| aat | tct | cct | caa | gaa | gtt | att | ggt | aaa | cgt | ggt | tct | gat | att | att | att | 1344 |
| Asn | Ser | Pro | Gln | Glu | Val | Ile | Gly | Lys | Arg | Gly | Ser | Asp | Ile | Ile | Ile |
| | | 435 | | | | | 440 | | | | | 445 | | | |

| gtt | ggt | cgt | ggt | att | att | tct | gct | gct | gat | cgt | ctt | gaa | gct | gct | gaa | 1392 |
| Val | Gly | Arg | Gly | Ile | Ile | Ser | Ala | Ala | Asp | Arg | Leu | Glu | Ala | Ala | Glu |
| | 450 | | | | | 455 | | | | | 460 | | | | |

| atg | tat | cgt | aaa | gct | gct | tgg | gaa | gct | tat | ctt | tct | cgt | ctt | ggt | gtt | 1440 |
| Met | Tyr | Arg | Lys | Ala | Ala | Trp | Glu | Ala | Tyr | Leu | Ser | Arg | Leu | Gly | Val |

<210> SEQ ID NO 10
<211> LENGTH: 480
<212> TYPE: PRT
<213> ORGANISM: homo sapiens

<400> SEQUENCE: 10

```
Met Ala Val Ala Arg Ala Leu Gly Pro Leu Val Thr Gly Leu Tyr
1               5                   10                  15

Asp Val Gln Ala Phe Lys Phe Gly Asp Phe Val Leu Lys Ser Gly Leu
                20                  25                  30

Ser Ser Pro Ile Tyr Ile Asp Leu Arg Gly Ile Val Ser Arg Pro Arg
            35                  40                  45

Leu Leu Ser Gln Val Ala Asp Ile Leu Phe Gln Thr Ala Gln Asn Ala
        50                  55                  60

Gly Ile Ser Phe Asp Thr Val Cys Gly Val Pro Tyr Thr Ala Leu Pro
65                  70                  75                  80

Leu Ala Thr Val Ile Cys Ser Thr Asn Gln Ile Pro Met Leu Ile Arg
                85                  90                  95

Arg Lys Glu Thr Lys Asp Tyr Gly Thr Lys Arg Leu Val Glu Gly Thr
            100                 105                 110

Ile Asn Pro Gly Glu Thr Cys Leu Ile Ile Glu Asp Val Val Thr Ser
        115                 120                 125

Gly Ser Ser Val Leu Glu Thr Val Glu Val Leu Gln Lys Glu Gly Leu
130                 135                 140

Lys Val Thr Asp Ala Ile Val Leu Leu Asp Arg Glu Gln Gly Gly Lys
145                 150                 155                 160

Asp Lys Leu Gln Ala His Gly Ile Arg Leu His Ser Val Cys Thr Leu
                165                 170                 175

Ser Lys Met Leu Glu Ile Leu Glu Gln Gln Lys Lys Val Asp Ala Glu
            180                 185                 190

Thr Val Gly Arg Val Lys Arg Phe Ile Gln Glu Asn Val Phe Val Ala
        195                 200                 205

Ala Asn His Asn Gly Ser Pro Leu Ser Ile Lys Glu Ala Pro Lys Glu
210                 215                 220

Leu Ser Phe Gly Ala Arg Ala Glu Leu Pro Arg Ile His Pro Val Ala
225                 230                 235                 240

Ser Lys Leu Leu Arg Leu Met Gln Lys Lys Glu Thr Asn Leu Cys Leu
                245                 250                 255

Ser Ala Asp Val Ser Leu Ala Arg Glu Leu Leu Gln Leu Ala Asp Ala
            260                 265                 270

Leu Gly Pro Ser Ile Cys Met Leu Lys Thr His Val Asp Ile Leu Asn
        275                 280                 285

Asp Phe Thr Leu Asp Val Met Lys Glu Leu Ile Thr Leu Ala Lys Cys
290                 295                 300

His Glu Phe Leu Ile Phe Glu Asp Arg Lys Phe Ala Asp Ile Gly Asn
305                 310                 315                 320

Thr Val Lys Lys Gln Tyr Glu Gly Gly Ile Phe Lys Ile Ala Ser Trp
                325                 330                 335

Ala Asp Leu Val Asn Ala His Val Val Pro Gly Ser Gly Val Val Lys
            340                 345                 350

Gly Leu Gln Glu Val Gly Leu Pro Leu His Arg Gly Cys Leu Leu Ile
```

|   |   |   |   |   |   |   |   |   |   |   |   |
|---|---|---|---|---|---|---|---|---|---|---|---|
|   |   |   | 355 |   |   |   | 360 |   |   |   | 365 |

Ala Glu Met Ser Ser Thr Gly Ser Leu Ala Thr Gly Asp Tyr Thr Arg
     370                           375                     380

Ala Ala Val Arg Met Ala Glu Glu His Ser Glu Phe Val Val Gly Phe
385                            390                       395                   400

Ile Ser Gly Ser Arg Val Ser Met Lys Pro Glu Phe Leu His Leu Thr
                 405                   410                   415

Pro Gly Val Gln Leu Glu Ala Gly Gly Asp Asn Leu Gly Gln Gln Tyr
           420                     425                    430

Asn Ser Pro Gln Glu Val Ile Gly Lys Arg Gly Ser Asp Ile Ile Ile
          435                  440                   445

Val Gly Arg Gly Ile Ile Ser Ala Ala Asp Arg Leu Glu Ala Ala Glu
     450                   455                   460

Met Tyr Arg Lys Ala Ala Trp Glu Ala Tyr Leu Ser Arg Leu Gly Val
465                           470                     475                   480

<210> SEQ ID NO 11
<211> LENGTH: 1227
<212> TYPE: DNA
<213> ORGANISM: Artificial Sequence
<220> FEATURE:
<223> OTHER INFORMATION: Fusion construct CDopt-UPRT
<220> FEATURE:
<221> NAME/KEY: CDS
<222> LOCATION: (1)..(1227)

<400> SEQUENCE: 11

| atg gtg acc ggc ggc atg gcc tcc aag tgg gat caa aag ggc atg gat | 48 |
|---|---|
| Met Val Thr Gly Gly Met Ala Ser Lys Trp Asp Gln Lys Gly Met Asp | |
| 1               5                   10                  15 | |

| atc gct tac gag gag gcc ctg ctg ggc tac aag gag ggc ggc gtg cct | 96 |
|---|---|
| Ile Ala Tyr Glu Glu Ala Leu Leu Gly Tyr Lys Glu Gly Gly Val Pro | |
|                 20                   25                    30 | |

| atc ggc ggc tgt ctg atc aac aac aag gac ggc agt gtg ctg ggc agg | 144 |
|---|---|
| Ile Gly Gly Cys Leu Ile Asn Asn Lys Asp Gly Ser Val Leu Gly Arg | |
|                35                   40                   45 | |

| ggc cac aac atg agg ttc cag aag ggc tcc gcc acc ctg cac ggc gag | 192 |
|---|---|
| Gly His Asn Met Arg Phe Gln Lys Gly Ser Ala Thr Leu His Gly Glu | |
|    50                    55                   60 | |

| atc tcc acc ctg gag aac tgt ggc agg ctg gag ggc aag gtg tac aag | 240 |
|---|---|
| Ile Ser Thr Leu Glu Asn Cys Gly Arg Leu Glu Gly Lys Val Tyr Lys | |
| 65                     70                   75                  80 | |

| gac acc acc ctg tac acc acc ctg tcc cct tgt gac atg tgt acc ggc | 288 |
|---|---|
| Asp Thr Thr Leu Tyr Thr Thr Leu Ser Pro Cys Asp Met Cys Thr Gly | |
|                 85                   90                   95 | |

| gct atc atc atg tac ggc atc cct agg tgt gtg atc ggc gag aac gtg | 336 |
|---|---|
| Ala Ile Ile Met Tyr Gly Ile Pro Arg Cys Val Ile Gly Glu Asn Val | |
|                 100                  105                110 | |

| aac ttc aag tcc aag ggc gag aag tac ctg caa acc agg ggc cac gag | 384 |
|---|---|
| Asn Phe Lys Ser Lys Gly Glu Lys Tyr Leu Gln Thr Arg Gly His Glu | |
|             115                  120                125 | |

| gtg gtg gtt gtt gac gat gag agg tgt aag aag ctg atg aag cag ttc | 432 |
|---|---|
| Val Val Val Val Asp Asp Glu Arg Cys Lys Lys Leu Met Lys Gln Phe | |
|    130                    135                  140 | |

| atc gac gag agg cct cag gac tgg ttc gag gat atc ggc gag aac ccg | 480 |
|---|---|
| Ile Asp Glu Arg Pro Gln Asp Trp Phe Glu Asp Ile Gly Glu Asn Pro | |
| 145                     150                   155                160 | |

| tta ttc ttt ttg gct tct cca ttc ttg tac ctt aca tat ctt ata tat | 528 |
|---|---|
| Leu Phe Phe Leu Ala Ser Pro Phe Leu Tyr Leu Thr Tyr Leu Ile Tyr | |
|                 165                  170                175 | |

```
tat cca aac aaa ggg tct ttc gtt agc aaa cct aga aat ctg caa aaa      576
Tyr Pro Asn Lys Gly Ser Phe Val Ser Lys Pro Arg Asn Leu Gln Lys
            180                 185                 190 atg tct tcg gaa cca ttt aag aac gtc tac ttg cta cct caa aca aac      624
Met Ser Ser Glu Pro Phe Lys Asn Val Tyr Leu Leu Pro Gln Thr Asn
        195                 200                 205 caa ttg ctg ggt ttg tac acc atc atc aga aat aag aat aca act aga      672
Gln Leu Leu Gly Leu Tyr Thr Ile Ile Arg Asn Lys Asn Thr Thr Arg
    210                 215                 220 cct gat ttc att ttc tac tcc gat aga atc atc aga ttg ttg gtt gaa      720
Pro Asp Phe Ile Phe Tyr Ser Asp Arg Ile Ile Arg Leu Leu Val Glu
225                 230                 235                 240 gaa ggt ttg aac cat cta cct gtg caa aag caa att gtg gaa act gac      768
Glu Gly Leu Asn His Leu Pro Val Gln Lys Gln Ile Val Glu Thr Asp
                245                 250                 255 acc aac gaa aac ttc gaa ggt gtc tca ttc atg ggt aaa atc tgt ggt      816
Thr Asn Glu Asn Phe Glu Gly Val Ser Phe Met Gly Lys Ile Cys Gly
            260                 265                 270 gtt tcc att gtc aga gct ggt gaa tcg atg gag caa gga tta aga gac      864
Val Ser Ile Val Arg Ala Gly Glu Ser Met Glu Gln Gly Leu Arg Asp
        275                 280                 285 tgt tgt agg tct gtg cgt atc ggt aaa att tta att caa agg gac gag      912
Cys Cys Arg Ser Val Arg Ile Gly Lys Ile Leu Ile Gln Arg Asp Glu
    290                 295                 300 gag act gct tta cca aag tta ttc tac gaa aaa tta cca gag gat ata      960
Glu Thr Ala Leu Pro Lys Leu Phe Tyr Glu Lys Leu Pro Glu Asp Ile
305                 310                 315                 320 tct gaa agg tat gtc ttc cta tta gac cca atg ctg gcc acc ggt ggt     1008
Ser Glu Arg Tyr Val Phe Leu Leu Asp Pro Met Leu Ala Thr Gly Gly
                325                 330                 335 agt gct atc atg gct aca gaa gtc ttg att aag aga ggt gtt aag cca     1056
Ser Ala Ile Met Ala Thr Glu Val Leu Ile Lys Arg Gly Val Lys Pro
            340                 345                 350 gag aga att tac ttc tta aac cta atc tgt agt aag gaa ggg att gaa     1104
Glu Arg Ile Tyr Phe Leu Asn Leu Ile Cys Ser Lys Glu Gly Ile Glu
        355                 360                 365 aaa tac cat gcc gcc ttc cca gag gtc aga att gtt act ggt gcc ctc     1152
Lys Tyr His Ala Ala Phe Pro Glu Val Arg Ile Val Thr Gly Ala Leu
    370                 375                 380 gac aga ggt cta gat gaa aac aag tat cta gtt cca ggg ttg ggt gac     1200
Asp Arg Gly Leu Asp Glu Asn Lys Tyr Leu Val Pro Gly Leu Gly Asp
385                 390                 395                 400 ttt ggt gac aga tac tac tgt gtt taa                                 1227
Phe Gly Asp Arg Tyr Tyr Cys Val
                405

<210> SEQ ID NO 12
<211> LENGTH: 408
<212> TYPE: PRT
<213> ORGANISM: Artificial Sequence
<220> FEATURE:
<223> OTHER INFORMATION: Synthetic Construct

<400> SEQUENCE: 12

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45
```

```
Gly His Asn Met Arg Phe Gln Lys Gly Ser Ala Thr Leu His Gly Glu
     50                  55                  60
Ile Ser Thr Leu Glu Asn Cys Gly Arg Leu Glu Gly Lys Val Tyr Lys
 65                  70                  75                  80
Asp Thr Thr Leu Tyr Thr Thr Leu Ser Pro Cys Asp Met Cys Thr Gly
                 85                  90                  95
Ala Ile Ile Met Tyr Gly Ile Pro Arg Cys Val Ile Gly Glu Asn Val
            100                 105                 110
Asn Phe Lys Ser Lys Gly Glu Lys Tyr Leu Gln Thr Arg Gly His Glu
        115                 120                 125
Val Val Val Asp Asp Glu Arg Cys Lys Lys Leu Met Lys Gln Phe
130                 135                 140
Ile Asp Glu Arg Pro Gln Asp Trp Phe Glu Asp Ile Gly Glu Asn Pro
145                 150                 155                 160
Leu Phe Phe Leu Ala Ser Pro Phe Leu Tyr Leu Thr Tyr Leu Ile Tyr
                165                 170                 175
Tyr Pro Asn Lys Gly Ser Phe Val Ser Lys Pro Arg Asn Leu Gln Lys
                180                 185                 190
Met Ser Ser Glu Pro Phe Lys Asn Val Tyr Leu Leu Pro Gln Thr Asn
            195                 200                 205
Gln Leu Leu Gly Leu Tyr Thr Ile Ile Arg Asn Lys Asn Thr Thr Arg
    210                 215                 220
Pro Asp Phe Ile Phe Tyr Ser Asp Arg Ile Ile Arg Leu Leu Val Glu
225                 230                 235                 240
Glu Gly Leu Asn His Leu Pro Val Gln Lys Gln Ile Val Glu Thr Asp
                245                 250                 255
Thr Asn Glu Asn Phe Glu Gly Val Ser Phe Met Gly Lys Ile Cys Gly
                260                 265                 270
Val Ser Ile Val Arg Ala Gly Glu Ser Met Glu Gln Gly Leu Arg Asp
            275                 280                 285
Cys Cys Arg Ser Val Arg Ile Gly Lys Ile Leu Ile Gln Arg Asp Glu
        290                 295                 300
Glu Thr Ala Leu Pro Lys Leu Phe Tyr Glu Lys Leu Pro Glu Asp Ile
305                 310                 315                 320
Ser Glu Arg Tyr Val Phe Leu Leu Asp Pro Met Leu Ala Thr Gly Gly
                325                 330                 335
Ser Ala Ile Met Ala Thr Glu Val Leu Ile Lys Arg Gly Val Lys Pro
                340                 345                 350
Glu Arg Ile Tyr Phe Leu Asn Leu Ile Cys Ser Lys Glu Gly Ile Glu
            355                 360                 365
Lys Tyr His Ala Ala Phe Pro Glu Val Arg Ile Val Thr Gly Ala Leu
        370                 375                 380
Asp Arg Gly Leu Asp Glu Asn Lys Tyr Leu Val Pro Gly Leu Gly Asp
385                 390                 395                 400
Phe Gly Asp Arg Tyr Tyr Cys Val
                405
```

<210> SEQ ID NO 13
<211> LENGTH: 1287
<212> TYPE: DNA
<213> ORGANISM: Artificial Sequence
<220> FEATURE:
<223> OTHER INFORMATION: Fusion construction - CDopt - linker - UPRT
<220> FEATURE:
<221> NAME/KEY: CDS

<222> LOCATION: (1)..(1287)

<400> SEQUENCE: 13

| | | | | | | | | | | | | | | | | |
|---|---|---|---|---|---|---|---|---|---|---|---|---|---|---|---|---|
| atg | gtg | acc | ggc | ggc | atg | gcc | tcc | aag | tgg | gat | caa | aag | ggc | atg | gat | 48 |
| Met | Val | Thr | Gly | Gly | Met | Ala | Ser | Lys | Trp | Asp | Gln | Lys | Gly | Met | Asp | |
| 1 | | | | 5 | | | | | 10 | | | | | 15 | | |
| atc | gct | tac | gag | gag | gcc | ctg | ctg | ggc | tac | aag | gag | ggc | ggc | gtg | cct | 96 |
| Ile | Ala | Tyr | Glu | Glu | Ala | Leu | Leu | Gly | Tyr | Lys | Glu | Gly | Gly | Val | Pro | |
| | | | 20 | | | | | 25 | | | | | 30 | | | |
| atc | ggc | ggc | tgt | ctg | atc | aac | aac | aag | gac | ggc | agt | gtg | ctg | ggc | agg | 144 |
| Ile | Gly | Gly | Cys | Leu | Ile | Asn | Asn | Lys | Asp | Gly | Ser | Val | Leu | Gly | Arg | |
| | | 35 | | | | | 40 | | | | | 45 | | | | |
| ggc | cac | aac | atg | agg | ttc | cag | aag | ggc | tcc | gcc | acc | ctg | cac | ggc | gag | 192 |
| Gly | His | Asn | Met | Arg | Phe | Gln | Lys | Gly | Ser | Ala | Thr | Leu | His | Gly | Glu | |
| | 50 | | | | | 55 | | | | | 60 | | | | | |
| atc | tcc | acc | ctg | gag | aac | tgt | ggc | agg | ctg | gag | ggc | aag | gtg | tac | aag | 240 |
| Ile | Ser | Thr | Leu | Glu | Asn | Cys | Gly | Arg | Leu | Glu | Gly | Lys | Val | Tyr | Lys | |
| 65 | | | | | 70 | | | | | 75 | | | | | 80 | |
| gac | acc | acc | ctg | tac | acc | acc | ctg | tcc | cct | tgt | gac | atg | tgt | acc | ggc | 288 |
| Asp | Thr | Thr | Leu | Tyr | Thr | Thr | Leu | Ser | Pro | Cys | Asp | Met | Cys | Thr | Gly | |
| | | | | 85 | | | | | 90 | | | | | 95 | | |
| gct | atc | atc | atg | tac | ggc | atc | cct | agg | tgt | gtg | atc | ggc | gag | aac | gtg | 336 |
| Ala | Ile | Ile | Met | Tyr | Gly | Ile | Pro | Arg | Cys | Val | Ile | Gly | Glu | Asn | Val | |
| | | | 100 | | | | | 105 | | | | | 110 | | | |
| aac | ttc | aag | tcc | aag | ggc | gag | aag | tac | ctg | caa | acc | agg | ggc | cac | gag | 384 |
| Asn | Phe | Lys | Ser | Lys | Gly | Glu | Lys | Tyr | Leu | Gln | Thr | Arg | Gly | His | Glu | |
| | | 115 | | | | | 120 | | | | | 125 | | | | |
| gtg | gtt | gtt | gtt | gac | gat | gag | agg | tgt | aag | aag | ctg | atg | aag | cag | ttc | 432 |
| Val | Val | Val | Val | Asp | Asp | Glu | Arg | Cys | Lys | Lys | Leu | Met | Lys | Gln | Phe | |
| | 130 | | | | | 135 | | | | | 140 | | | | | |
| atc | gac | gag | agg | cct | cag | gac | tgg | ttc | gag | gat | atc | ggc | gag | tcc | ggc | 480 |
| Ile | Asp | Glu | Arg | Pro | Gln | Asp | Trp | Phe | Glu | Asp | Ile | Gly | Glu | Ser | Gly | |
| 145 | | | | | 150 | | | | | 155 | | | | | 160 | |
| ggc | ggc | gcc | tcc | ggc | ggc | ggc | gcc | tcc | ggc | ggc | ggc | gcc | tcc | ggc | ggc | 528 |
| Gly | Gly | Ala | Ser | Gly | Gly | Gly | Ala | Ser | Gly | Gly | Gly | Ala | Ser | Gly | Gly | |
| | | | | 165 | | | | | 170 | | | | | 175 | | |
| ggc | gcc | aac | ccg | tta | ttc | ttt | ttg | gct | tct | cca | ttc | ttg | tac | ctt | aca | 576 |
| Gly | Ala | Asn | Pro | Leu | Phe | Phe | Leu | Ala | Ser | Pro | Phe | Leu | Tyr | Leu | Thr | |
| | | | 180 | | | | | 185 | | | | | 190 | | | |
| tat | ctt | ata | tat | tat | cca | aac | aaa | ggg | tct | ttc | gtt | agc | aaa | cct | aga | 624 |
| Tyr | Leu | Ile | Tyr | Tyr | Pro | Asn | Lys | Gly | Ser | Phe | Val | Ser | Lys | Pro | Arg | |
| | | 195 | | | | | 200 | | | | | 205 | | | | |
| aat | ctg | caa | aaa | atg | tct | tcg | gaa | cca | ttt | aag | aac | gtc | tac | ttg | cta | 672 |
| Asn | Leu | Gln | Lys | Met | Ser | Ser | Glu | Pro | Phe | Lys | Asn | Val | Tyr | Leu | Leu | |
| | 210 | | | | | 215 | | | | | 220 | | | | | |
| cct | caa | aca | aac | caa | ttg | ctg | ggt | ttg | tac | acc | atc | atc | aga | aat | aag | 720 |
| Pro | Gln | Thr | Asn | Gln | Leu | Leu | Gly | Leu | Tyr | Thr | Ile | Ile | Arg | Asn | Lys | |
| 225 | | | | | 230 | | | | | 235 | | | | | 240 | |
| aat | aca | act | aga | cct | gat | ttc | att | ttc | tac | tcc | gat | aga | atc | atc | aga | 768 |
| Asn | Thr | Thr | Arg | Pro | Asp | Phe | Ile | Phe | Tyr | Ser | Asp | Arg | Ile | Ile | Arg | |
| | | | | 245 | | | | | 250 | | | | | 255 | | |
| ttg | ttg | gtt | gaa | gaa | ggt | ttg | aac | cat | cta | cct | gtg | caa | aag | caa | att | 816 |
| Leu | Leu | Val | Glu | Glu | Gly | Leu | Asn | His | Leu | Pro | Val | Gln | Lys | Gln | Ile | |
| | | | 260 | | | | | 265 | | | | | 270 | | | |
| gtg | gaa | act | gac | acc | aac | gaa | aac | ttc | gaa | ggt | gtc | tca | ttc | atg | ggt | 864 |
| Val | Glu | Thr | Asp | Thr | Asn | Glu | Asn | Phe | Glu | Gly | Val | Ser | Phe | Met | Gly | |
| | | 275 | | | | | 280 | | | | | 285 | | | | |
| aaa | atc | tgt | ggt | gtt | tcc | att | gtc | aga | gct | ggt | gaa | tcg | atg | gag | caa | 912 |
| Lys | Ile | Cys | Gly | Val | Ser | Ile | Val | Arg | Ala | Gly | Glu | Ser | Met | Glu | Gln | |
| | 290 | | | | | 295 | | | | | 300 | | | | | |

```
gga tta aga gac tgt tgt agg tct gtg cgt atc ggt aaa att tta att      960
Gly Leu Arg Asp Cys Cys Arg Ser Val Arg Ile Gly Lys Ile Leu Ile
305                 310                 315                 320 caa agg gac gag gag act gct tta cca aag tta ttc tac gaa aaa tta     1008
Gln Arg Asp Glu Glu Thr Ala Leu Pro Lys Leu Phe Tyr Glu Lys Leu
                325                 330                 335 cca gag gat ata tct gaa agg tat gtc ttc cta tta gac cca atg ctg     1056
Pro Glu Asp Ile Ser Glu Arg Tyr Val Phe Leu Leu Asp Pro Met Leu
            340                 345                 350 gcc acc ggt ggt agt gct atc atg gct aca gaa gtc ttg att aag aga     1104
Ala Thr Gly Gly Ser Ala Ile Met Ala Thr Glu Val Leu Ile Lys Arg
        355                 360                 365 ggt gtt aag cca gag aga att tac ttc tta aac cta atc tgt agt aag     1152
Gly Val Lys Pro Glu Arg Ile Tyr Phe Leu Asn Leu Ile Cys Ser Lys
    370                 375                 380 gaa ggg att gaa aaa tac cat gcc gcc ttc cca gag gtc aga att gtt     1200
Glu Gly Ile Glu Lys Tyr His Ala Ala Phe Pro Glu Val Arg Ile Val
385                 390                 395                 400 act ggt gcc ctc gac aga ggt cta gat gaa aac aag tat cta gtt cca     1248
Thr Gly Ala Leu Asp Arg Gly Leu Asp Glu Asn Lys Tyr Leu Val Pro
                405                 410                 415 ggg ttg ggt gac ttt ggt gac aga tac tac tgt gtt taa                 1287
Gly Leu Gly Asp Phe Gly Asp Arg Tyr Tyr Cys Val
            420                 425

<210> SEQ ID NO 14
<211> LENGTH: 428
<212> TYPE: PRT
<213> ORGANISM: Artificial Sequence
<220> FEATURE:
<223> OTHER INFORMATION: Synthetic Construct

<400> SEQUENCE: 14

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ser Gly
145                 150                 155                 160

Gly Gly Ala Ser Gly Gly Gly Ala Ser Gly Gly Ala Ser Gly Gly
                165                 170                 175

Gly Ala Asn Pro Leu Phe Phe Leu Ala Ser Pro Phe Leu Tyr Leu Thr
            180                 185                 190
```

```
Tyr Leu Ile Tyr Tyr Pro Asn Lys Gly Ser Phe Val Ser Lys Pro Arg
            195                 200                 205

Asn Leu Gln Lys Met Ser Ser Glu Pro Phe Lys Asn Val Tyr Leu Leu
        210                 215                 220

Pro Gln Thr Asn Gln Leu Leu Gly Leu Tyr Thr Ile Ile Arg Asn Lys
225                 230                 235                 240

Asn Thr Thr Arg Pro Asp Phe Ile Phe Tyr Ser Asp Arg Ile Ile Arg
                245                 250                 255

Leu Leu Val Glu Glu Gly Leu Asn His Leu Pro Val Gln Lys Gln Ile
            260                 265                 270

Val Glu Thr Asp Thr Asn Glu Asn Phe Glu Gly Val Ser Phe Met Gly
        275                 280                 285

Lys Ile Cys Gly Val Ser Ile Val Arg Ala Gly Glu Ser Met Glu Gln
290                 295                 300

Gly Leu Arg Asp Cys Cys Arg Ser Val Arg Ile Gly Lys Ile Leu Ile
305                 310                 315                 320

Gln Arg Asp Glu Glu Thr Ala Leu Pro Lys Leu Phe Tyr Glu Lys Leu
                325                 330                 335

Pro Glu Asp Ile Ser Glu Arg Tyr Val Phe Leu Leu Asp Pro Met Leu
            340                 345                 350

Ala Thr Gly Gly Ser Ala Ile Met Ala Thr Glu Val Leu Ile Lys Arg
        355                 360                 365

Gly Val Lys Pro Glu Arg Ile Tyr Phe Leu Asn Leu Ile Cys Ser Lys
370                 375                 380

Glu Gly Ile Glu Lys Tyr His Ala Ala Phe Pro Glu Val Arg Ile Val
385                 390                 395                 400

Thr Gly Ala Leu Asp Arg Gly Leu Asp Glu Asn Lys Tyr Leu Val Pro
                405                 410                 415

Gly Leu Gly Asp Phe Gly Asp Arg Tyr Tyr Cys Val
            420                 425

<210> SEQ ID NO 15
<211> LENGTH: 1200
<212> TYPE: DNA
<213> ORGANISM: Artificial Sequence
<220> FEATURE:
<223> OTHER INFORMATION: Fusion Construct - CDopt3 - OPRT
<220> FEATURE:
<221> NAME/KEY: CDS
<222> LOCATION: (1)..(1200)

<400> SEQUENCE: 15 atg gtg acc ggc ggc atg gcc tcc aag tgg gat caa aag ggc atg gat      48
Met Val Thr Gly Gly Met Ala Ser Lys Trp Asp Gln Lys Gly Met Asp
1               5                   10                  15 atc gct tac gag gag gcc ctg ctg ggc tac aag gag ggc ggc gtg cct      96
Ile Ala Tyr Glu Glu Ala Leu Leu Gly Tyr Lys Glu Gly Gly Val Pro
            20                  25                  30 atc ggc ggc tgt ctg atc aac aac aag gac ggc agt gtg ctg ggc agg     144
Ile Gly Gly Cys Leu Ile Asn Asn Lys Asp Gly Ser Val Leu Gly Arg
        35                  40                  45 ggc cac aac atg agg ttc cag aag ggc tcc gcc acc ctg cac ggc gag     192
Gly His Asn Met Arg Phe Gln Lys Gly Ser Ala Thr Leu His Gly Glu
    50                  55                  60 atc tcc acc ctg gag aac tgt ggc agg ctg gag ggc aag gtg tac aag     240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc     288
```

```
            Asp Thr Thr Leu Tyr Thr Thr Leu Ser Pro Cys Asp Met Cys Thr Gly
                            85              90              95 gct atc atc atg tac ggc atc cct agg tgt gtg atc ggc gag aac gtg         336
Ala Ile Ile Met Tyr Gly Ile Pro Arg Cys Val Ile Gly Glu Asn Val
                100             105             110 aac ttc aag tcc aag ggc gag aag tac ctg caa acc agg ggc cac gag         384
Asn Phe Lys Ser Lys Gly Glu Lys Tyr Leu Gln Thr Arg Gly His Glu
            115             120             125 gtg gtg gtt gtt gac gat gag agg tgt aag aag ctg atg aag cag ttc         432
Val Val Val Val Asp Asp Glu Arg Cys Lys Lys Leu Met Lys Gln Phe
130             135             140 atc gac gag agg cct cag gac tgg ttc gag gat atc ggc gag gcg gtc         480
Ile Asp Glu Arg Pro Gln Asp Trp Phe Glu Asp Ile Gly Glu Ala Val
145             150             155             160 gct cgt gca gct ttg ggg cca ttg gtg acg ggt ctg tac gac gtg cag         528
Ala Arg Ala Ala Leu Gly Pro Leu Val Thr Gly Leu Tyr Asp Val Gln
                165             170             175 gct ttc aag ttt ggg gac ttc gtg ctg aag agc ggg ctt tcc tcc ccc         576
Ala Phe Lys Phe Gly Asp Phe Val Leu Lys Ser Gly Leu Ser Ser Pro
            180             185             190 atc tac atc gat ctg cgg ggc atc gtg tct cga ccg cgt ctt ctg agt         624
Ile Tyr Ile Asp Leu Arg Gly Ile Val Ser Arg Pro Arg Leu Leu Ser
        195             200             205 cag gtt gca gat att tta ttc caa act gcc caa aat gca ggc atc agt         672
Gln Val Ala Asp Ile Leu Phe Gln Thr Ala Gln Asn Ala Gly Ile Ser
210             215             220 ttt gac acc gtg tgt gga gtg cct tat aca gct ttg cca ttg gct aca         720
Phe Asp Thr Val Cys Gly Val Pro Tyr Thr Ala Leu Pro Leu Ala Thr
225             230             235             240 gtt atc tgt tca acc aat caa att cca atg ctt att aga agg aaa gaa         768
Val Ile Cys Ser Thr Asn Gln Ile Pro Met Leu Ile Arg Arg Lys Glu
                245             250             255 aca aag gat tat gga act aag cgt ctt gta gaa gga act att aat cca         816
Thr Lys Asp Tyr Gly Thr Lys Arg Leu Val Glu Gly Thr Ile Asn Pro
            260             265             270 gga gaa acc tgt tta atc att gaa gat gtt gtc acc agt gga tct agt         864
Gly Glu Thr Cys Leu Ile Ile Glu Asp Val Val Thr Ser Gly Ser Ser
        275             280             285 gtt ttg gaa act gtt gag gtt ctt cag aag gag ggc ttg aag gtc act         912
Val Leu Glu Thr Val Glu Val Leu Gln Lys Glu Gly Leu Lys Val Thr
290             295             300 gat gcc ata gtg ctg ttg gac aga gag cag gga ggc aag gac aag ttg         960
Asp Ala Ile Val Leu Leu Asp Arg Glu Gln Gly Gly Lys Asp Lys Leu
305             310             315             320 cag gcg cac ggg atc cgc ctc cac tca gtg tgt aca ttg tcc aaa atg        1008
Gln Ala His Gly Ile Arg Leu His Ser Val Cys Thr Leu Ser Lys Met
                325             330             335 ctg gag att ctc gag cag cag aaa aaa gtt gat gct gag aca gtt ggg        1056
Leu Glu Ile Leu Glu Gln Gln Lys Lys Val Asp Ala Glu Thr Val Gly
            340             345             350 aga gtg aag agg ttt att cag gag aat gtc ttt gtg gca gcg aat cat        1104
Arg Val Lys Arg Phe Ile Gln Glu Asn Val Phe Val Ala Ala Asn His
        355             360             365 aat ggt tct ccc ctt tct ata aag gaa gca ccc aaa gaa ctc agc ttc        1152
Asn Gly Ser Pro Leu Ser Ile Lys Glu Ala Pro Lys Glu Leu Ser Phe
370             375             380 ggt gca cgt gca gag ctg ccc agg atc cac cca gtt gca tcg aag taa        1200
Gly Ala Arg Ala Glu Leu Pro Arg Ile His Pro Val Ala Ser Lys
385             390             395
```

```
<210> SEQ ID NO 16
<211> LENGTH: 399
<212> TYPE: PRT
<213> ORGANISM: Artificial Sequence
<220> FEATURE:
<223> OTHER INFORMATION: Synthetic Construct

<400> SEQUENCE: 16

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ala Val
145                 150                 155                 160

Ala Arg Ala Ala Leu Gly Pro Leu Val Thr Gly Leu Tyr Asp Val Gln
                165                 170                 175

Ala Phe Lys Phe Gly Asp Phe Val Leu Lys Ser Gly Leu Ser Ser Pro
            180                 185                 190

Ile Tyr Ile Asp Leu Arg Gly Ile Val Ser Arg Pro Arg Leu Leu Ser
        195                 200                 205

Gln Val Ala Asp Ile Leu Phe Gln Thr Ala Gln Asn Ala Gly Ile Ser
    210                 215                 220

Phe Asp Thr Val Cys Gly Val Pro Tyr Thr Ala Leu Pro Leu Ala Thr
225                 230                 235                 240

Val Ile Cys Ser Thr Asn Gln Ile Pro Met Leu Ile Arg Arg Lys Glu
                245                 250                 255

Thr Lys Asp Tyr Gly Thr Lys Arg Leu Val Glu Gly Thr Ile Asn Pro
            260                 265                 270

Gly Glu Thr Cys Leu Ile Ile Glu Asp Val Val Thr Ser Gly Ser Ser
        275                 280                 285

Val Leu Glu Thr Val Glu Val Leu Gln Lys Glu Gly Leu Lys Val Thr
    290                 295                 300

Asp Ala Ile Val Leu Leu Asp Arg Glu Gln Gly Gly Lys Asp Lys Leu
305                 310                 315                 320

Gln Ala His Gly Ile Arg Leu His Ser Val Cys Thr Leu Ser Lys Met
                325                 330                 335

Leu Glu Ile Leu Glu Gln Gln Lys Lys Val Asp Ala Glu Thr Val Gly
            340                 345                 350

Arg Val Lys Arg Phe Ile Gln Glu Asn Val Phe Val Ala Ala Asn His
        355                 360                 365
```

```
Asn Gly Ser Pro Leu Ser Ile Lys Glu Ala Pro Lys Glu Leu Ser Phe
    370                 375                 380

Gly Ala Arg Ala Glu Leu Pro Arg Ile His Pro Val Ala Ser Lys
385                 390                 395

<210> SEQ ID NO 17
<211> LENGTH: 1260
<212> TYPE: DNA
<213> ORGANISM: Artificial Sequence
<220> FEATURE:
<223> OTHER INFORMATION: Fusion Construct - CDopt3 - linker - OPRT
<220> FEATURE:
<221> NAME/KEY: CDS
<222> LOCATION: (1)..(1260)

<400> SEQUENCE: 17 atg gtg acc ggc ggc atg gcc tcc aag tgg gat caa aag ggc atg gat      48
Met Val Thr Gly Gly Met Ala Ser Lys Trp Asp Gln Lys Gly Met Asp
1               5                  10                  15 atc gct tac gag gag gcc ctg ctg ggc tac aag gag ggc ggc gtg cct      96
Ile Ala Tyr Glu Glu Ala Leu Leu Gly Tyr Lys Glu Gly Gly Val Pro
            20                  25                  30 atc ggc ggc tgt ctg atc aac aac aag gac ggc agt gtg ctg ggc agg     144
Ile Gly Gly Cys Leu Ile Asn Asn Lys Asp Gly Ser Val Leu Gly Arg
        35                  40                  45 ggc cac aac atg agg ttc cag aag ggc tcc gcc acc ctg cac ggc gag     192
Gly His Asn Met Arg Phe Gln Lys Gly Ser Ala Thr Leu His Gly Glu
    50                  55                  60 atc tcc acc ctg gag aac tgt ggc agg ctg gag ggc aag gtg tac aag     240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc     288
Asp Thr Thr Leu Tyr Thr Thr Leu Ser Pro Cys Asp Met Cys Thr Gly
                85                  90                  95 gct atc atc atg tac ggc atc cct agg tgt gtg atc ggc gag aac gtg     336
Ala Ile Ile Met Tyr Gly Ile Pro Arg Cys Val Ile Gly Glu Asn Val
            100                 105                 110 aac ttc aag tcc aag ggc gag aag tac ctg caa acc agg ggc cac gag     384
Asn Phe Lys Ser Lys Gly Glu Lys Tyr Leu Gln Thr Arg Gly His Glu
        115                 120                 125 gtg gtg gtt gtt gac gat gag agg tgt aag aag ctg atg aag cag ttc     432
Val Val Val Val Asp Asp Glu Arg Cys Lys Lys Leu Met Lys Gln Phe
    130                 135                 140 atc gac gag agg cct cag gac tgg ttc gag gat atc ggc gag tcc ggc     480
Ile Asp Glu Arg Pro Gln Asp Trp Phe Glu Asp Ile Gly Glu Ser Gly
145                 150                 155                 160 ggc ggc gcc tcc ggc ggc ggc gcc tcc ggc ggc ggc gcc tcc ggc ggc     528
Gly Gly Ala Ser Gly Gly Gly Ala Ser Gly Gly Gly Ala Ser Gly Gly
                165                 170                 175 ggc gcc gcg gtc gct cgt gca gct ttg ggg cca ttg gtg acg ggt ctg     576
Gly Ala Ala Val Ala Arg Ala Ala Leu Gly Pro Leu Val Thr Gly Leu
            180                 185                 190 tac gac gtg cag gct ttc aag ttt ggg gac ttc gtg ctg aag agc ggg     624
Tyr Asp Val Gln Ala Phe Lys Phe Gly Asp Phe Val Leu Lys Ser Gly
        195                 200                 205 ctt tcc tcc ccc atc tac atc gat ctg cgg ggc atc gtg tct cga ccg     672
Leu Ser Ser Pro Ile Tyr Ile Asp Leu Arg Gly Ile Val Ser Arg Pro
    210                 215                 220 cgt ctt ctg agt cag gtt gca gat att tta ttc caa act gcc caa aat     720
Arg Leu Leu Ser Gln Val Ala Asp Ile Leu Phe Gln Thr Ala Gln Asn
225                 230                 235                 240
```

```
gca ggc atc agt ttt gac acc gtg tgt gga gtg cct tat aca gct ttg      768
Ala Gly Ile Ser Phe Asp Thr Val Cys Gly Val Pro Tyr Thr Ala Leu
            245                 250                 255 cca ttg gct aca gtt atc tgt tca acc aat caa att cca atg ctt att      816
Pro Leu Ala Thr Val Ile Cys Ser Thr Asn Gln Ile Pro Met Leu Ile
        260                 265                 270 aga agg aaa gaa aca aag gat tat gga act aag cgt ctt gta gaa gga      864
Arg Arg Lys Glu Thr Lys Asp Tyr Gly Thr Lys Arg Leu Val Glu Gly
    275                 280                 285 act att aat cca gga gaa acc tgt tta atc att gaa gat gtt gtc acc      912
Thr Ile Asn Pro Gly Glu Thr Cys Leu Ile Ile Glu Asp Val Val Thr
290                 295                 300 agt gga tct agt gtt ttg gaa act gtt gag gtt ctt cag aag gag ggc      960
Ser Gly Ser Ser Val Leu Glu Thr Val Glu Val Leu Gln Lys Glu Gly
305                 310                 315                 320 ttg aag gtc act gat gcc ata gtg ctg ttg gac aga gag cag gga ggc     1008
Leu Lys Val Thr Asp Ala Ile Val Leu Leu Asp Arg Glu Gln Gly Gly
            325                 330                 335 aag gac aag ttg cag gcg cac ggg atc cgc ctc cac tca gtg tgt aca     1056
Lys Asp Lys Leu Gln Ala His Gly Ile Arg Leu His Ser Val Cys Thr
        340                 345                 350 ttg tcc aaa atg ctg gag att ctc gag cag cag aaa aaa gtt gat gct     1104
Leu Ser Lys Met Leu Glu Ile Leu Glu Gln Gln Lys Lys Val Asp Ala
    355                 360                 365 gag aca gtt ggg aga gtg aag agg ttt att cag gag aat gtc ttt gtg     1152
Glu Thr Val Gly Arg Val Lys Arg Phe Ile Gln Glu Asn Val Phe Val
370                 375                 380 gca gcg aat cat aat ggt tct ccc ctt tct ata aag gaa gca ccc aaa     1200
Ala Ala Asn His Asn Gly Ser Pro Leu Ser Ile Lys Glu Ala Pro Lys
385                 390                 395                 400 gaa ctc agc ttc ggt gca cgt gca gag ctg ccc agg atc cac cca gtt     1248
Glu Leu Ser Phe Gly Ala Arg Ala Glu Leu Pro Arg Ile His Pro Val
            405                 410                 415 gca tcg aag taa                                                     1260
Ala Ser Lys
```

<210> SEQ ID NO 18
<211> LENGTH: 419
<212> TYPE: PRT
<213> ORGANISM: Artificial Sequence
<220> FEATURE:
<223> OTHER INFORMATION: Synthetic Construct

<400> SEQUENCE: 18

```
Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
```

115                 120                 125
Val Val Val Asp Asp Glu Arg Cys Lys Lys Leu Met Lys Gln Phe
        130                 135                 140

Ile Asp Glu Arg Pro Gln Asp Trp Phe Glu Asp Ile Gly Glu Ser Gly
145                 150                 155                 160

Gly Gly Ala Ser Gly Gly Ala Ser Gly Gly Ala Ser Gly Gly
                165                 170                 175

Gly Ala Ala Val Ala Arg Ala Ala Leu Gly Pro Leu Val Thr Gly Leu
            180                 185                 190

Tyr Asp Val Gln Ala Phe Lys Phe Gly Asp Phe Val Leu Lys Ser Gly
                195                 200                 205

Leu Ser Ser Pro Ile Tyr Ile Asp Leu Arg Gly Ile Val Ser Arg Pro
    210                 215                 220

Arg Leu Leu Ser Gln Val Ala Asp Ile Leu Phe Gln Thr Ala Gln Asn
225                 230                 235                 240

Ala Gly Ile Ser Phe Asp Thr Val Cys Gly Val Pro Tyr Thr Ala Leu
                245                 250                 255

Pro Leu Ala Thr Val Ile Cys Ser Thr Asn Gln Ile Pro Met Leu Ile
            260                 265                 270

Arg Arg Lys Glu Thr Lys Asp Tyr Gly Thr Lys Arg Leu Val Glu Gly
                275                 280                 285

Thr Ile Asn Pro Gly Glu Thr Cys Leu Ile Ile Glu Asp Val Val Thr
    290                 295                 300

Ser Gly Ser Ser Val Leu Glu Thr Val Glu Val Leu Gln Lys Glu Gly
305                 310                 315                 320

Leu Lys Val Thr Asp Ala Ile Val Leu Leu Asp Arg Glu Gln Gly Gly
                325                 330                 335

Lys Asp Lys Leu Gln Ala His Gly Ile Arg Leu His Ser Val Cys Thr
            340                 345                 350

Leu Ser Lys Met Leu Glu Ile Leu Glu Gln Gln Lys Lys Val Asp Ala
                355                 360                 365

Glu Thr Val Gly Arg Val Lys Arg Phe Ile Gln Glu Asn Val Phe Val
    370                 375                 380

Ala Ala Asn His Asn Gly Ser Pro Leu Ser Ile Lys Glu Ala Pro Lys
385                 390                 395                 400

Glu Leu Ser Phe Gly Ala Arg Ala Glu Leu Pro Arg Ile His Pro Val
                405                 410                 415

Ala Ser Lys

<210> SEQ ID NO 19
<211> LENGTH: 11892
<212> TYPE: DNA
<213> ORGANISM: Artificial Sequence
<220> FEATURE:
<223> OTHER INFORMATION: RCR Vector - pAC3-yCD2

<400> SEQUENCE: 19
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360

```
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg ggctcgtcc gggatcggga accccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcacccc cttagaggag gatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaacctttt aacgtcggat ggccgcgaga cggcacctttt aaccgagacc   1380
tcatcaccca ggttaagatc aaggtctttt cacctggccc gcatggacac ccagaccagg   1440
tccctacat cgtgacctgg gaagccttgg cttttgaccc ccctccctgg gtcaagccct   1500
ttgtacaccc taagcctccg cctcctcttc tccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtgggggcc gctcatcgac ctacttacag   1680
aagaccccc gccttatagg gacccaagac caccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgttc   1980
tcatcaccca tcagcccacc tgggacgact gtcagcagct gttggggact ctgctgaccg   2040
gagaagaaaa acaacgggtg ctcttagagg ctagaaaggc ggtgcgggc gatgatgggc   2100
gccccactca actgcccaat gaagtcgatg ccgcttttcc cctcgagcgc ccagactggg   2160
attacaccac ccaggcaggt aggaaccacc tagtccacta cgccagttg ctcctagcgg   2220
gtctccaaaa cgcgggcaga agccccacca atttggccaa ggtaaaagga ataacacaag   2280
ggcccaatga gtccccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga gatttaaaa aacaagacgc   2460
ttggagattt ggttagagag gcagaaaaga tctttaataa acgagaaacc ccggaagaaa   2520
gagaggaacg tatcaggaga gaaacagagg aaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
```

```
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc gggggcaac     2880 ccgtcacctt cctggtagat actggggccc aacactccgt gctgacccaa atcctggac     2940 ccctaagtga taagtctgcc tgggtccaag ggctactgg aggaaagcgg tatcgctgga     3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg gcatgggac     3300 tggcagttcg ccaagctcct ctgatcatac ctctgaaagc aacctctacc ccgtgtcca    3360 taaaacaata ccccatgtca caagaagcca gactggggat caagcccac atacagagac    3420 tgttggacca gggaatactg gtaccctgcc agtcccctg gaacacgccc ctgctacccg     3480
ttaagaaacc agggactaat gattataggc ctgtccagga tctgagagaa gtcaacaagc    3540
gggtggaaga catccacccc accgtgccca acccttacaa cctcttgagc gggctccac     3600 cgtcccacca gtggtacact gtgcttgatt taaaggatgc cttttctgc ctgagactcc      3660 accccaccag tcagcctctc ttcgcctttg agtggagaga tccagagatg gaatctcag     3720 gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900 gggcctgtt acaaacccta gggaacctcg ggtatcgggc ctcggccaag aaagcccaaa     3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattgggc ccagaccaac     4200 aaaaggccta tcaagaaatc aagcaagctc ttctaactgc cccagccctg gggttgccag    4260
atttgactaa gccctttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cggacatccc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
```

```
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacccttt tctggctgga   5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttgggat tgattggaaa ttacattgtg      5820
catacagacc ccaaagctca ggccaggtag aaagaatgaa tagaaccatc aaggagactt    5880
taactaaatt aacgcttgca actggctcta gagactgggt gctcctactc cccttagccc     5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccccaccg ccctcaaagt agacggcatc gcagcttgga    6300
tacacgccgc ccacgtgaag gctgccgacc ccggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttg acttttacgt gtgccctggg cataccgtaa agtcggggtg    6720
tgggggacca ggagagggct actgtggtaa atgggggtgt gaaaccaccg gacaggctta    6780
ctggaagccc acatcatcgt gggacctaat ctcccttaag cgcggtaaca cccctggga    6840 cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
```

-continued

```
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
gagagacagc atggccaaat taagagaaag gcttaatcag acacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca tgaacgcgtt actggccgaa    8340
gccgcttgga ataaggccgg tgtgcgtttg tctatatgtt attttccacc atattgccgt    8400
cttttggcaa tgtgagggcc cggaaacctg ccctgtctt cttgacgagc attcctaggg    8460
gtctttcccc tctcgccaaa ggaatgcaag gtctgttgaa tgtcgtgaag gaagcagttc    8520
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgaccggcgg catggcctcc aagtgggatc aaaagggcat ggatatcgct tacgaggagg    8940
ccctgctggg ctacaaggag ggcggcgtgc ctatcggcgg ctgtctgatc aacaacaagg    9000
acggcagtgt gctgggcagg ggccacaaca tgaggttcca gaagggctcc gccaccctgc    9060
acggcgagat ctccaccctg gagaactgtg gcaggctgga gggcaaggtg tacaaggaca    9120
ccaccctgta caccaccctg tccccttgtg acatgtgtac cggcgctatc atcatgtacg    9180
gcatccctag gtgtgtgatc ggcgagaacg tgaacttcaa gtccaagggc gagaagtacc    9240
tgcaaaccag gggccacgag gtggtggttg ttgacgatga gaggtgtaag aagctgatga    9300
agcagttcat cgacgagagg cctcaggact ggttcgagga tatcggcgag taagcggccg    9360
cagataaaat aaaagatttt atttagtctc cagaaaaagg ggggaatgaa agaccccacc    9420
tgtaggtttg gcaagctagc ttaagtaacg ccatttttgca aggcatggaa aaatacataa    9480
ctgagaatag agaagttcag atcaaggtca ggaacagatg gaacagctga atatgggcca    9540
aacaggatat ctgtggtaag cagttcctgc cccggctcag ggccaagaac agatggaaca    9600
gctgaatatg ggccaaacag gatatctgtg gtaagcagtt cctgccccgg ctcagggcca    9660
agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
```

```
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcgggggt ctttcattac atgtgagcaa aaggccagca   10020
aaaggccagg aaccgtaaaa aggccgcgtt gctggcgttt ttccataggc tccgcccccc   10080
tgacgagcat cacaaaaatc gacgctcaag tcagaggtgg cgaaacccga caggactata   10140
aagataccag gcgtttcccc ctggaagctc cctcgtgcgc tctcctgttc cgaccctgcc   10200
gcttaccgga tacctgtccg cctttctccc ttcgggaagc gtggcgcttt ctcaatgctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
cgctcagtgg aacgaaaact cacgttaagg gattttggtc atgagattat caaaaaggat   10740
cttcacctag atccttttaa attaaaaatg aagttttaaa tcaatctaaa gtatatatga   10800
gtaaacttgg tctgacagtt accaatgctt aatcagtgag gcacctatct cagcgatctg   10860
tctatttcgt tcatccatag ttgcctgact ccccgtcgtg tagataacta cgatacggga   10920
gggcttacca tctggcccca gtgctgcaat gataccgcga cccacgct caccggctcc   10980
agatttatca gcaataaacc agccagccgg aagggccgag cgcagaagtg gtcctgcaac   11040
tttatccgcc tccatccagt ctattaattg ttgccgggaa gctagagtaa gtagttcgcc   11100
agttaatagt ttgcgcaacg ttgttgccat tgctgcaggc atcgtggtgt cacgctcgtc   11160
gtttggtatg gcttcattca gctccggttc ccaacgatca aggcgagtta catgatcccc   11220
catgttgtgc aaaaaagcgg ttagctcctt cggtcctccg atcgttgtca gaagtaagtt   11280
ggccgcagtg ttatcactca tggttatggc agcactgcat aattctctta ctgtcatgcc   11340
atccgtaaga tgcttttctg tgactggtga gtactcaacc aagtcattct gagaatagtg   11400
tatgcggcga ccgagttgct cttgcccggc gtcaacacgg gataataccg cgccacatag   11460
cagaacttta aaagtgctca tcattggaaa acgttcttcg gggcgaaaac tctcaaggat   11520
cttaccgctg ttgagatcca gttcgatgta acccactcgt gcacccaact gatcttcagc   11580
atcttttact ttcaccagcg tttctgggtg agcaaaaaca ggaaggcaaa atgccgcaaa   11640
aaagggaata agggcgacac ggaaatgttg aatactcata ctcttccttt ttcaatatta   11700
ttgaagcatt tatcagggtt attgtctcat gagcggatac atatttgaat gtatttagaa   11760
aaataaacaa ataggggttc cgcgcacatt tccccgaaaa gtgccacctg acgtctaaga   11820
aaccattatt atcatgacat taacctataa aaataggcgt atcacgaggc cctttcgtct   11880
tcaagaattc at                                                       11892
```

<210> SEQ ID NO 20
<211> LENGTH: 11892
<212> TYPE: DNA
<213> ORGANISM: Artificial Sequence
<220> FEATURE:
<223> OTHER INFORMATION: RCR Vector - pAC3-yCD

<400> SEQUENCE: 20

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgcc ccattgacgc aaatgggcg gtaggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcggggggtc     720
tttcatttgg ggctcgtcc gggatcggga gaccccctgcc cagggaccac cgacccacca     780
ccgggaggta agctggccag caacttatct gtgtctgtcc gattgtctag tgtctatgac     840
tgattttatg cgcctgcgtc ggtactagtt agctaactag ctctgtatct ggcggacccg     900
tggtggaact gacgagttcg gaacacccgg ccgcaaccct gggagacgtc ccagggactt     960
cggggggccgt ttttgtggcc cgacctgagt ccaaaaatcc cgatcgtttt ggactctttg    1020
gtgcacccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcacccttt aaccgagacc    1380
tcatcaccca ggttaagatc aaggtctttt cacctggccc gcatggacac ccagaccagg    1440
tcccctacat cgtgacctgg gaagccttgg cttttgaccc cctcctgg gtcaagccct    1500
ttgtacaccc taagcctccg cctcctcttc tccatccgc cccgtctctc ccccttgaac    1560
ctcctcgttc gaccccgcct cgatcctccc tttatccagc cctcactcct tctctaggcg    1620
ccaaacctaa acctcaagtt cttttctgaca gtgggggcc gctcatcgac ctacttacag    1680
aagaccccc gccttatagg gacccaagac caccccttc cgacagggac ggaaatggtg    1740
gagaagcgac ccctgcggga gaggcaccgg acccctcccc aatggcatct cgcctacgtg    1800
ggagacggga gcccctgtg ccgactcca ctacctcgca ggcattcccc ctccgcgcag    1860
gaggaaacgg acagcttcaa tactggccgt tctcctcttc tgacctttac aactggaaaa    1920
ataataaccc ttctttttct gaagatccag gtaaactgac agctctgatc gagtctgttc    1980
tcatcaccca tcagcccacc tgggacgact gtcagcagct gttggggact ctgctgaccg    2040
gagaagaaaa acaacgggtg ctcttagagg ctagaaaggc ggtgcgggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
```

```
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg gctaaagat tgtcccaaga   2760 aaccacgagg acctcgggga ccaagacccc agacctccct cctgacccta gatgactagg   2820
gaggtcaggg tcaggagccc cccctgaac ccaggataac cctcaaagtc gggggcaac    2880 ccgtcacctt cctggtagat actggggccc aacactccgt gctgacccaa aatcctggac   2940
ccctaagtga taagtctgcc tgggtccaag ggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag catcggctac atgagacctc aaaagagcca gatgtttctc   3240
tagggtccac atggctgtct gattttcctc aggcctgggc ggaaaccggg gcatgggac    3300 tggcagttcg ccaagctcct ctgatcatac ctctgaaagc aacctctacc ccgtgtcca    3360 taaaacaata ccccatgtca caagaagcca gactggggat caagcccac atacagagac    3420 tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc cttttttctgc ctgagactcc   3660 accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagcc cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt cagaaatgg    4140 cagccccctt gtaccctctc accaaaacg ggactctgtt taattggggc ccagaccaac    4200
aaaaggccta tcaagaaatc aagcaagctc ttctaactgc cccagcctg gggttgccag    4260 atttgactaa gcccttgaa ctctttgtcg acgagaagca gggctacgcc aaaggtgtcc    4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggcccc catgcagtag   4500 aggcactagt caaacaaccc ccgaccgct ggctttccaa cgcccggatg actcactatc    4560
aggccttgct tttggacacg gacccggctcc agttcggacc ggtggtagcc ctgaacccgg   4620
ctacgctgct cccactgcct gaggaagggc tgcaacacaa ctgcccttgat atcctggccg   4680
```

```
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacacgcg cgaggctaga ggcaaccgga tggctgacca agcggcccga aaggcagcca   5160
tcacagagac tccagacacc tctaccctcc tcatagaaaa ttcatcaccc tacacctcag   5220 aacatttttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagttttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggcccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc accccccaccg ccctcaaagt agacggcatc gcagcttgga   6300
tacacgccgc ccacgtgaag gctgccgacc ccggggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccatcagg tctttaatgt   6480 aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg acaggcttta   6780
ctggaagccc acatcatcgt gggacctaat ctcccttaag cgcggtaaca cccccctggga   6840 cacgggatgc tctaaagttg cctgtggccc ctgctacgac ctctccaaag tatccaattc   6900
cttccaaggg gctactcgag ggggcagatg caacccctcta gtcctagaat tcactgatgc   6960 aggaaaaaaag gctaactggg acgggcccaa atcgtgggga ctgagactgt accgacagg   7020 aacagatcct attaccatgt tctccctgac ccggcaggtc cttaatgtgg gaccccgagt   7080
```

```
ccccataggg cccaacccag tattacccga ccaaagactc ccttcctcac caatagagat   7140
tgtaccggct ccacagccac ctagccccct caataccagt taccccoctt ccactaccag   7200
tacaccctca acctcccta caagtccaag tgtcccacag ccaccccag gaactggaga     7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga caatgtgggc ttgcagcac tggattgact ccctgcttgt ccaccacggt    7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggttaccca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtt actggccgaa   8340
gccgcttgga ataaggccgg tgtgcgtttg tctatatgtt attttccacc atattgccgt   8400
cttttggcaa tgtgagggcc cggaaacctg gccctgtctt cttgacgagc attcctaggg   8460
gtctttcccc tctcgccaaa ggaatgcaag gtctgttgaa tgtcgtgaag gaagcagttc   8520
ctctggaagc ttcttgaaga caaacaacgt ctgtagcgac cctttgcagg cagcggaacc   8580
ccccacctgg cgacaggtgc ctctgcggcc aaaagccacg tgtataagat acacctgcaa   8640
aggcggcaca accccagtgc cacgttgtga gttggatagt tgtggaaaga gtcaaatggc   8700
tctcctcaag cgtattcaac aaggggctga aggatgccca gaaggtaccc cattgtatgg   8760
gatctgatct ggggcctcgg tgcacatgct ttacatgtgt ttagtcgagg ttaaaaaaac   8820
gtctaggccc cccgaaccac ggggacgtgg ttttcctttg aaaaacacga ttataaatgg   8880
tgacaggggg aatggcaagc aagtgggatc agaagggtat ggacattgcc tatgaggagg   8940
cggccttagg ttacaaagag ggtggtgttc ctattggcgg atgtcttatc aataacaaag   9000
acggaagtgt tctcggtcgt ggtcacaaca tgagatttca aaagggatcc gccacactac   9060
atggtgagat ctccactttg gaaaactgtg ggagattaga gggcaaagtg tacaaagata   9120
ccactttgta tacgacgctg tctccatgcg acatgtgtac aggtgccatc atcatgtatg   9180
gtattccacg ctgtgttgtc ggtgagaacg ttaatttcaa aagtaagggc gagaaatatt   9240
tacaaactag aggtcacgag gttgttgttg ttgacgatga gaggtgtaaa aagatcatga   9300
aacaatttat cgatgaaaga cctcaggatt ggtttgaaga tattggtgag taggcggccg   9360
cagataaaat aaaagatttt atttagtctc cagaaaaagg ggggaatgaa agaccccacc   9420
```

-continued

```
tgtaggtttg gcaagctagc ttaagtaacg ccattttgca aggcatggaa aaatacataa    9480
ctgagaatag agaagttcag atcaaggtca ggaacagatg gaacagctga atatgggcca    9540
aacaggatat ctgtggtaag cagttcctgc cccggctcag ggccaagaac agatggaaca    9600
gctgaatatg ggccaaacag gatatctgtg gtaagcagtt cctgcccggc tcagggcca    9660
agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcgggggt ctttcattac atgtgagcaa aaggccagca   10020
aaaggccagg aaccgtaaaa aggccgcgtt gctggcgttt ttccataggc tccgcccccc   10080
tgacgagcat cacaaaaatc gacgctcaag tcagaggtgg cgaaacccga caggactata   10140
aagataccag gcgtttcccc ctggaagctc cctcgtgcgc tctcctgttc cgaccctgcc   10200
gcttaccgga tacctgtccg cctttctccc ttcgggaagc gtggcgcttt ctcaatgctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
cgctcagtgg aacgaaaact cacgttaagg attttggtc atgagattat caaaaaggat   10740
cttcacctag atccttttaa attaaaaatg aagttttaaa tcaatctaaa gtatatatga   10800
gtaaacttgg tctgacagtt accaatgctt aatcagtgag gcacctatct cagcgatctg   10860
tctatttcgt tcatccatag ttgcctgact ccccgtcgtg tagataacta cgatacggga   10920
gggcttacca tctggcccca gtgctgcaat gataccgcga acccacgct caccggctcc   10980
agatttatca gcaataaacc agccagccgg aagggccgag cgcagaagtg gtcctgcaac   11040
tttatccgcc tccatccagt ctattaattg ttgccgggaa gctagagtaa gtagttcgcc   11100
agttaatagt ttgcgcaacg ttgttgccat tgctgcaggc atcgtggtgt cacgctcgtc   11160
gtttggtatg gcttcattca gctccggttc ccaacgatca aggcgagtta catgatcccc   11220
catgttgtgc aaaaaagcgg ttagctcctt cggtcctccg atcgttgtca gaagtaagtt   11280
ggccgcagtg ttatcactca tggttatggc agcactgcat aattctctta ctgtcatgcc   11340
atccgtaaga tgcttttctg tgactggtga gtactcaacc aagtcattct gagaatagtg   11400
tatgcggcga ccgagttgct cttgcccggc gtcaacacgg gataataccg cgccacatag   11460
cagaacttta aaagtgctca tcattggaaa acgttcttcg gggcgaaaac tctcaaggat   11520
cttaccgctg ttgagatcca gttcgatgta acccactcgt gcacccaact gatcttcagc   11580
atcttttact ttcaccagcg tttctgggtg agcaaaaaca ggaaggcaaa atgccgcaaa   11640
aaagggaata agggcgacac ggaaatgttg aatactcata ctcttccttt ttcaatatta   11700
ttgaagcatt tatcagggtt attgtctcat gagcggatac atatttgaat gtatttagaa   11760
aaataaacaa ataggggttc cgcgcacatt tccccgaaaa gtgccacctg acgtctaaga   11820
```

```
aaccattatt atcatgacat taacctataa aaataggcgt atcacgaggc cctttcgtct    11880
tcaagaattc at                                                        11892

<210> SEQ ID NO 21
<211> LENGTH: 12007
<212> TYPE: DNA
<213> ORGANISM: Artificial Sequence
<220> FEATURE:
<223> OTHER INFORMATION: RCR Vector - pACE-CD

<400> SEQUENCE: 21
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aatgtcgta acaactccgc cccattgacg caaatgggcg taggcgtgt      540 acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcggggggtc    720 tttcatttgg gggctcgtcc gggatcggga gaccccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg     900
tggtggaact gacgagttcg gaacacccgg ccgcaaccct gggagacgtc ccagggactt    960 cggggggccgt ttttgtggcc cgacctgagt ccaaaaatcc cgatcgtttt ggactctttg    1020 gtgcacccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcaccttt aaccgagacc    1380
tcatcaccca ggttaagatc aaggtctttt cacctggccc gcatggacac ccagaccagg    1440
tcccctacat cgtgacctgg gaagccttgg cttttgaccc cctccctgg gtcaagccct    1500 ttgtacaccc taagcctccg cctcctcttc tccatccgc ccgtctctc cccttgaac     1560 ctcctcgttc gaccccgcct cgatcctccc tttatccagc cctcactcct tctctaggcg    1620
ccaaacctaa acctcaagtt ctttctgaca gtggggggcc gctcatcgac ctacttacag    1680
aagacccccc gccttatagg gacccaagac caccccttc cgacagggac ggaaatggtg    1740
gagaagcgac ccctgcggga gaggcaccgg acccctcccc aatggcatct cgcctacgtg    1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
```

```
ataataaccc ttcttttttct gaagatccag gtaaactgac agctctgatc gagtctgttc    1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatcgac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc gggggcaac    2880
ccgtcacctt cctggtagat actggggccc aacactccgt gctgacccaa atcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg gcatgggac    3300
tggcagttcg ccaagctcct ctgatcatac ctctgaaagc aacctctacc cccgtgtcca    3360
taaaacaata ccccatgtca caagaagcca gactggggat caagcccac atacagagac    3420
tgttggacca gggaatactg gtaccctgcc agtccccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttttctgc ctgagactcc    3660
acccccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagaccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagcctg ggttgccag    4260
atttgactaa gcccttttgaa ctctttgtcg acagaaagca gggctacgcc aaaggtgtcc    4320
```

```
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagttttat agatacctt tctggctgga    5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttgggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000 gggcacccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccaccg ccctcaaagt gacggcatc gcagcttgga    6300 tacacgccgc ccacgtgaag gctgccgacc ccggggggtgg accatcctct agactgacat    6360
ggcgcgttca acgctctcaa aacccccctca agataagatt aacccgtgga agcccttaat    6420
agtcatggga gtcctgttag gagtagggat ggcagagagc cccatcagg tctttaatgt    6480 aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600 gtgggacccct tcagaccagg aaccgtatgt cgggtatggc tgcaagtacc ccgcagggag    6660
```

```
acagcggacc cggactttg acttttacgt gtgccctggg cataccgtaa agtcggggtg    6720
tgggggacca ggagagggct actgtggtaa atggggtgt gaaaccaccg gacaggctta    6780
ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accgacagg    7020
aacagatcct attaccatgt tctccctgac ccggcaggtc cttaatgtgg gaccccgagt    7080
ccccataggg cccaacccag tattacccga ccaaagactc ccttcctcac aatagagat    7140
tgtaccggct ccacagccac ctagccccct caataccagt tacccccctt ccactaccag    7200
tacaccctca acctccccta caagtccaag tgtcccacag ccaccccag gaactggaga    7260
tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgttttttat gcagaccaca cggggctagt    8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgatta gtccaatttg ttaaagacag gatatcagtg gtccaggctc tagttttgac    8280
tcaacaatat caccagctga agcctataga gtacgagcca tgacgtacgt tactggccga    8340
agccgcttgg aataaggccg gtgtgcgttt gtctatatgt tattttccac catattgccg    8400
tcttttggca atgtgagggc ccggaaacct ggccctgtct tcttgacgag cattcctagg    8460
ggtctttccc ctctcgccaa aggaatgcaa ggtctgttga atgtcgtgaa ggaagcagtt    8520
cctctggaag cttcttgaag acaaacaacg tctgtagcga cccttttgcag gcagcggaac    8580
cccccacctg gcgacaggtg cctctgcggc caaaagccac gtgtataaga tacacctgca    8640
aaggcggcac aaccccagtg ccacgttgtg agttggatag ttgtggaaag agtcaaatgg    8700
ctctcctcaa gcgtattcaa caaggggctg aaggatgccc agaaggtacc ccattgtatg    8760
ggatctgatc tggggcctcg gtgcacatgc tttacatgtg tttagtcgag gttaaaaaaa    8820
cgtctaggcc ccccgaacca cggggacgtg gttttccttt gaaaaacacg ataataccat    8880
ggtgacaggg ggaatggcaa gcaagtggga tcagaagggt atggacattg cctatgagga    8940
ggcggcctta ggttacaaag agggtggtgt tcctattggc ggatgtctta tcaataacaa    9000
agacggaagt gttctcggtc gtggtcacaa catgagattt caaaagggat ccgccacact    9060
```

```
acatggtgag atctccactt tggaaaactg tgggagatta gagggcaaag tgtacaaaga    9120
taccactttg tatacgacgc tgtctccatg cgacatgtgt acaggtgcca tcatcatgta    9180
tggtattcca cgctgtgttg tcggtgagaa cgttaatttc aaaagtaagg gcgagaaata    9240
tttacaaact agaggtcacg aggttgttgt tgttgacgat gagaggtgta aaagatcat     9300 gaaacaattt atcgatgaaa gacctcagga ttggtttgaa gatattggtg agtaggcggc    9360
cgcgccatag ataaaataaa agattttatt tagtctccag aaaaaggggg gaatgaaaga    9420
ccccacctgt aggtttggca agctagctta agtaacgcca ttttgcaagg catggaaaaa    9480
tacataactg agaatagaga agttcagatc aaggtcagga acagatggaa cagctgaata    9540
tgggccaaac aggatatctg tggtaagcag ttcctgcccc ggctcagggc caagaacaga    9600
tggaacagct gaatatgggc caaacaggat atctgtggta agcagttcct gcccggctc     9660 agggccaaga acagatggtc cccagatgcg gtccagccct cagcagtttc tagagaacca    9720
tcagatgttt ccagggtgcc ccaaggacct gaaatgaccc tgtgccttgt ttaaactaac    9780
caatcagttc gcttctcgct tctgttcgcg cgcttctgct ccccgagctc aataaaagag    9840
cccacaaccc ctcactcggg gcgccagtcc tccgattgac tgagtcgccc gggtacccgt    9900
gtatccaata aaccctcttg cagttgcatc cgacttgtgg tctcgctgtt ccttgggagg    9960
gtctcctctg agtgattgac tacccgtcag cgggggtctt tcatttgggg gctcgtccgg    10020
gatcgggaga cccctgccca gggaccaccg acccaccacc gggaggtaag ctggctgcct    10080
cgcgcgtttc ggtgatgacg gtgaaaacct ctgacatgtg agcaaaaggc cagcaaaagg    10140
ccaggaaccg taaaaaggcc gcgttgctgg cgttttttcca taggctccgc ccccctgacg    10200
agcatcacaa aaatcgacgc tcaagtcaga ggtggcgaaa cccgacagga ctataaagat    10260
accaggcgtt cccccctgga agctccctcg tgcgctctcc tgttccgacc ctgccgctta    10320
ccggatacct gtccgccttt ctcccttcgg gaagcgtggc gctttctcaa tgctcacgct    10380
gtaggtatct cagttcggtg taggtcgttc gctccaagct gggctgtgtg cacgaacccc    10440
ccgttcagcc cgaccgctgc gccttatccg gtaactatcg tcttgagtcc aacccggtaa    10500
gacacgactt atcgccactg gcagcagcca ctggtaacag gattagcaga gcgaggtatg    10560
taggcggtgc tacagagttc ttgaagtggt ggcctaacta cggctacact agaaggacag    10620
tatttggtat ctgcgctctg ctgaagccag ttaccttcgg aaaaagagtt ggtagctctt    10680
gatccggcaa acaaaccacc gctggtagcg gtggtttttt tgtttgcaag cagcagatta    10740
cgcgcagaaa aaaaggatct caagaagatc ctttgatctt ttctacgggg tctgacgctc    10800
agtggaacga aaactcacgt taagggattt tggtcatgag attatcaaaa aggatcttca    10860
cctagatcct tttaaattaa aaatgaagtt ttaaatcaat ctaaagtata tatgagtaaa    10920
cttggtctga cagttaccaa tgcttaatca gtgaggcacc tatctcagcg atctgtctat    10980
ttcgttcatc catagttgcc tgactccccg tcgtgtagat aactacgata cgggagggct    11040
taccatctgg ccccagtgct gcaatgatac cgcgagaccc acgctcaccg gctccagatt    11100
tatcagcaat aaaccagcca gccggaaggg ccgagcgcag aagtggtcct gcaactttat    11160
ccgcctccat ccagtctatt aattgttgcc gggaagctag agtaagtagt tcgccagtta    11220
atagtttgcg caacgttgtt gccattgctg caggcatcgt ggtgtcacgc tcgtcgtttg    11280
gtatggcttc attcagctcc ggttcccaac gatcaaggcg agttacatga tcccccatgt    11340
tgtgcaaaaa agcggttagc tccttcggtc ctccgatcgt tgtcagaagt aagttggccg    11400
```

```
cagtgttatc actcatggtt atggcagcac tgcataattc tcttactgtc atgccatccg   11460
taagatgctt ttctgtgact ggtgagtact caaccaagtc attctgagaa tagtgtatgc   11520
ggcgaccgag ttgctcttgc ccggcgtcaa cacgggataa taccgcgcca catagcagaa   11580
ctttaaaagt gctcatcatt ggaaaacgtt cttcggggcg aaaactctca aggatcttac   11640
cgctgttgag atccagttcg atgtaaccca ctcgtgcacc caactgatct tcagcatctt   11700
ttactttcac cagcgtttct gggtgagcaa aaacaggaag gcaaaatgcc gcaaaaaagg   11760
gaataagggc gacacggaaa tgttgaatac tcatactctt ccttttcaa tattattgaa    11820 gcatttatca gggttattgt ctcatgagcg gatacatatt tgaatgtatt tagaaaaata   11880
aacaaatagg ggttccgcgc acatttcccc gaaaagtgcc acctgacgtc taagaaacca   11940
ttattatcat gacattaacc tataaaaata ggcgtatcac gaggccctt cgtcttcaag    12000 aattcat                                                             12007

<210> SEQ ID NO 22
<211> LENGTH: 11893
<212> TYPE: DNA
<213> ORGANISM: Artificial Sequence
<220> FEATURE:
<223> OTHER INFORMATION: RCR Vector - pAC3-yCD2

<400> SEQUENCE: 22
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgcc ccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga gaccctgcc cagggaccac cgacccacca    780
ccgggaggta agctggccag caacttatct gtgtctgtcc gattgtctag tgtctatgac    840 tgatttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaaa   1200
atatgggcca gactgttacc actcccttaa gtttgacctt aggtcactgg aaagatgtcg   1260
agcggatcgc tcacaaccag tcggtagatg tcaagaagag cgttgggtt accttctgct   1320 ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
```

```
tcccctacat cgtgacctgg gaagccttgg cttttgaccc ccctccctgg gtcaagccct    1500
ttgtacaccc taagcctccg cctcctcttc ctccatccgc cccgtctctc cccttgaac    1560
ctcctcgttc gaccccgcct cgatcctccc tttatccagc cctcactcct tctctaggcg    1620
ccaaacctaa acctcaagtt ctttctgaca gtgggggggcc gctcatcgac ctacttacag    1680
aagaccccc gccttatagg acccaagac cacccccttc cgacagggac ggaaatggtg      1740
gagaagcgac ccctgcggga gaggcaccgg acccctcccc aatggcatct cgcctacgtg    1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttct gaagatccag gtaaactgac agctctgatc gagtctgtcc     1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc ggggggcaac    2880
ccgtcacctt cctggtagat actggggccc aacactccgt gctgacccaa atcctggac    2940
ccctaagtga taagtctgcc tgggtccaag gggctactgg aggaaagcgg tatcgctgga   3000
ccacggatcg caaagtacat ctagctaccg gtaaggtcac ccactctttc ctccatgtac    3060
cagactgtcc ctatcctctg ttaggaagag attggctgac taaactaaaa gcccaaatcc    3120
actttgaggg atcaggagcc caggttatgg gaccaatggg gcagccctg caagtgttga     3180
ccctaaatat agaagatgag tatcggctac atgagacctc aaaagagcca gatgtttctc    3240
tagggtccac atggctgtct gattttcctc aggcctgggc ggaaaccggg gcatgggac     3300
tggcagttcg ccaagctcct ctgatcatac ctctgaaagc aacctctacc cccgtgtcca    3360
taaaacaata cccatgtca caagaagcca gactggggat caagcccac atacagagac      3420
tgttggacca gggaatactg gtaccctgcc agtcccctg gaacacgccc ctgctacccg     3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc ctttttctgc ctgagactcc    3660
accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
```

```
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccca gggaacctcg ggtatcgggc ctcggccaag aaagcccaaa     3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140 cagcccctt gtaccctctc accaaaacgg ggactctgtt taattggggc ccagaccaac     4200
aaaaggccta tcaagaaatc aagcaagctc ttctaactgc cccagccctg ggttgccag     4260 atttgactaa gccctttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca gcggcccga aaggcagcca    5160 tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580 agccccggatt gtatggctat aaatatcttc tagtttttat agataccttt tctggctgga    5640
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttgggat tgattggaaa ttacattgtg      5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
ggcacccccc gcccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
```

```
gcgacacagt gtgggtccgc cgacaccaga ctaagaacct agaacctcgc tggaaaggac    6240
cttacacagt cctgctgacc accccaccg ccctcaaagt agacggcatc gcagcttgga    6300
tacacgccgc ccacgtgaag gctgccgacc ccggggtgg accatcctct agactgacat    6360
ggcgcgttca acgctctcaa aacccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcaggag    6660 acagcggacc cggacttttg acttttacgt gtgccctggg cataccgtaa agtcggggtg    6720
tgggggacca ggagagggct actgtggtaa atggggggtgt gaaaccaccg gacaggctta    6780
ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca cacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680 ctccccgat tatatgtatg gtcagcttga acagcgtacc aaatataaaa gagagccagt    7740
atcattgacc ctgccccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgttttttat gcagaccaca cggggctagt    8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca tgaacgcgtt actgccgaa    8340 gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
```

```
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgaccggcgg catggcctcc aagtgggatc aaaagggcat ggatatcgct tacgaggagg    8940
ccctgctggg ctacaaggag ggcggcgtgc ctatcggcgg ctgtctgatc aacaacaagg    9000
acggcagtgt gctgggcagg ggccacaaca tgaggttcca gaagggctcc gccaccctgc    9060
acggcgagat ctccaccctg gagaactgtg caggctgga gggcaaggtg tacaaggaca    9120
ccaccctgta caccaccctg tcccttgtg acatgtgtac cggcgctatc atcatgtacg    9180
gcatccctag gtgtgtgatc ggcgagaacg tgaacttcaa gtccaagggc gagaagtacc    9240
tgcaaaccag ggggccacgag gtggtggttg ttgacgatga gaggtgtaag aagctgatga    9300
agcagttcat cgacgagagg cctcaggact ggttcgagga tatcggcgag taagcggccg    9360
cagataaaat aaaagatttt atttagtctc cagaaaaagg ggggaatgaa agaccccacc    9420
tgtaggtttg gcaagctagc ttaagtaacg ccattttgca aggcatggaa aatacataa    9480
ctgagaatag agaagttcag atcaaggtca ggaacagatg gaacagctga atatgggcca    9540
aacaggatat ctgtggtaag cagttcctgc cccggctcag gccaagaac agatggaaca    9600
gctgaatatg gccaaacag gatatctgtg gtaagcagtt cctgcccgg ctcagggcca    9660
agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcgggggt ctttcattac atgtgagcaa aaggccagca   10020
aaaggccagg aaccgtaaaa aggccgcgtt gctggcgttt ttccataggc tccgcccccc   10080
tgacgagcat cacaaaaatc gacgctcaag tcagaggtgg cgaaacccga caggactata   10140
aagataccag gcgtttcccc ctggaagctc cctcgtgcgc tctcctgttc cgaccctgcc   10200
gcttaccgga tacctgtccg cctttctccc ttcgggaagc gtggcgcttt ctcatagctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
cgctcagtgg aacgaaaact cacgttaagg gattttggtc atgagattat caaaaaggat   10740
cttcacctag atcctttaa attaaaaatg aagttttaaa tcaatctaaa gtatatatga   10800
gtaaacttgg tctgacagtt accaatgctt aatcagtgag gcacctatct cagcgatctg   10860
tctatttcgt tcatccatag ttgcctgact ccccgtcgtg tagataacta cgatacggga   10920
```

```
gggcttacca tctggcccca gtgctgcaat gataccgcga gacccacgct caccggctcc    10980
agatttatca gcaataaacc agccagccgg aagggccgag cgcagaagtg gtcctgcaac    11040
tttatccgcc tccatccagt ctattaattg ttgccgggaa gctagagtaa gtagttcgcc    11100
agttaatagt ttgcgcaacg ttgttgccat tgctgcaggc atcgtggtgt cacgctcgtc    11160
gtttggtatg gcttcattca gctccggttc ccaacgatca aggcgagtta catgatcccc    11220
catgttgtgc aaaaaagcgg ttagctcctt cggtcctccg atcgttgtca gaagtaagtt    11280
ggccgcagtg ttatcactca tggttatggc agcactgcat aattctctta ctgtcatgcc    11340
atccgtaaga tgcttttctg tgactggtga gtactcaacc aagtcattct gagaatagtg    11400
tatgcggcga ccgagttgct cttgcccggc gtcaacacgg ataataccg cgccacatag     11460 cagaacttta aaagtgctca tcattggaaa acgttcttcg gggcgaaaac tctcaaggat    11520
cttaccgctg ttgagatcca gttcgatgta acccactcgt gcacccaact gatcttcagc    11580
atcttttact ttcaccagcg tttctgggtg agcaaaaaca ggaaggcaaa atgccgcaaa    11640
aaagggaata agggcgacac ggaaatgttg aatactcata ctcttccttt tcaatatta    11700 ttgaagcatt tatcagggtt attgtctcat gagcggatac atatttgaat gtatttagaa    11760
aaataaacaa atagggttc cgcgcacatt tccccgaaaa gtgccacctg acgtctaaga    11820
aaccattatt atcatgacat taacctataa aaataggcgt atcacgaggc cctttcgtct    11880
tcaagaattc cat                                                        11893

<210> SEQ ID NO 23
<211> LENGTH: 4473
<212> TYPE: DNA
<213> ORGANISM: Homo sapiens
<220> FEATURE:
<221> NAME/KEY: CDS
<222> LOCATION: (175)..(3942)

<400> SEQUENCE: 23
aaggggaggt aaccctggcc cctttggtcg ggcccccggg cagccgcgcg ccccttccca     60 cggggcccctt tactgcgccg cgcgcccggc ccccaccccct cgcagcaccc cgcgccccgc   120
gccctcccag ccgggtccag ccggagccat ggggccggag ccgcagtgag cacc atg      177
                                                             Met
                                                             1
```

```
gag ctg gcg gcc ttg tgc cgc tgg ggg ctc ctc ctc gcc ctc ttg ccc       225
Glu Leu Ala Ala Leu Cys Arg Trp Gly Leu Leu Leu Ala Leu Leu Pro
        5                   10                  15 ccc gga gcc gcg agc acc caa gtg tgc acc ggc aca gac atg aag ctg       273
Pro Gly Ala Ala Ser Thr Gln Val Cys Thr Gly Thr Asp Met Lys Leu
    20                  25                  30 cgg ctc cct gcc agt ccc gag acc cac ctg gac atg ctc cgc cac ctc       321
Arg Leu Pro Ala Ser Pro Glu Thr His Leu Asp Met Leu Arg His Leu
35                  40                  45 tac cag ggc tgc cag gtg gtg cag gga aac ctg gaa ctc acc tac ctg       369
Tyr Gln Gly Cys Gln Val Val Gln Gly Asn Leu Glu Leu Thr Tyr Leu
 50                  55                  60                  65 ccc acc aat gcc agc ctg tcc ttc ctg cag gat atc cag gag gtg cag       417
Pro Thr Asn Ala Ser Leu Ser Phe Leu Gln Asp Ile Gln Glu Val Gln
                70                  75                  80 ggc tac gtg ctc atc gct cac aac caa gtg agg cag gtc cca ctg cag       465
Gly Tyr Val Leu Ile Ala His Asn Gln Val Arg Gln Val Pro Leu Gln
            85                  90                  95 agg ctg cgg att gtg cga ggc acc cag ctc ttt gag gac aac tat gcc       513
```

```
              Arg Leu Arg Ile Val Arg Gly Thr Gln Leu Phe Glu Asp Asn Tyr Ala
                          100                 105                 110 ctg gcc gtg cta gac aat gga gac ccg ctg aac aat acc acc cct gtc         561
Leu Ala Val Leu Asp Asn Gly Asp Pro Leu Asn Asn Thr Thr Pro Val
115                 120                 125 aca ggg gcc tcc cca gga ggc ctg cgg gag ctg cag ctt cga agc ctc         609
Thr Gly Ala Ser Pro Gly Gly Leu Arg Glu Leu Gln Leu Arg Ser Leu
130                 135                 140                 145 aca gag atc ttg aaa gga ggg gtc ttg atc cag cgg aac ccc cag ctc         657
Thr Glu Ile Leu Lys Gly Gly Val Leu Ile Gln Arg Asn Pro Gln Leu
                150                 155                 160 tgc tac cag gac acg att ttg tgg aag gac atc ttc cac aag aac aac         705
Cys Tyr Gln Asp Thr Ile Leu Trp Lys Asp Ile Phe His Lys Asn Asn
            165                 170                 175 cag ctg gct ctc aca ctg ata gac acc aac cgc tct cgg gcc tgc cac         753
Gln Leu Ala Leu Thr Leu Ile Asp Thr Asn Arg Ser Arg Ala Cys His
        180                 185                 190 ccc tgt tct ccg atg tgt aag ggc tcc cgc tgc tgg gga gag agt tct         801
Pro Cys Ser Pro Met Cys Lys Gly Ser Arg Cys Trp Gly Glu Ser Ser
195                 200                 205 gag gat tgt cag agc ctg acg cgc act gtc tgt gcc ggt ggc tgt gcc         849
Glu Asp Cys Gln Ser Leu Thr Arg Thr Val Cys Ala Gly Gly Cys Ala
210                 215                 220                 225 cgc tgc aag ggg cca ctg ccc act gac tgc tgc cat gag cag tgt gct         897
Arg Cys Lys Gly Pro Leu Pro Thr Asp Cys Cys His Glu Gln Cys Ala
                230                 235                 240 gcc ggc tgc acg ggc ccc aag cac tct gac tgc ctg gcc tgc ctc cac         945
Ala Gly Cys Thr Gly Pro Lys His Ser Asp Cys Leu Ala Cys Leu His
            245                 250                 255 ttc aac cac agt ggc atc tgt gag ctg cac tgc cca gcc ctg gtc acc         993
Phe Asn His Ser Gly Ile Cys Glu Leu His Cys Pro Ala Leu Val Thr
        260                 265                 270 tac aac aca gac acg ttt gag tcc atg ccc aat ccc gag ggc cgg tat        1041
Tyr Asn Thr Asp Thr Phe Glu Ser Met Pro Asn Pro Glu Gly Arg Tyr
275                 280                 285 aca ttc ggc gcc agc tgt gtg act gcc tgt ccc tac aac tac ctt tct        1089
Thr Phe Gly Ala Ser Cys Val Thr Ala Cys Pro Tyr Asn Tyr Leu Ser
290                 295                 300                 305 acg gac gtg gga tcc tgc acc ctc gtc tgc ccc ctg cac aac caa gag        1137
Thr Asp Val Gly Ser Cys Thr Leu Val Cys Pro Leu His Asn Gln Glu
                310                 315                 320 gtg aca gca gag gat gga aca cag cgg tgt gag aag tgc agc aag ccc        1185
Val Thr Ala Glu Asp Gly Thr Gln Arg Cys Glu Lys Cys Ser Lys Pro
            325                 330                 335 tgt gcc cga gtg tgc tat ggt ctg ggc atg gag cac ttg cga gag gtg        1233
Cys Ala Arg Val Cys Tyr Gly Leu Gly Met Glu His Leu Arg Glu Val
        340                 345                 350 agg gca gtt acc agt gcc aat atc cag gag ttt gct ggc tgc aag aag        1281
Arg Ala Val Thr Ser Ala Asn Ile Gln Glu Phe Ala Gly Cys Lys Lys
355                 360                 365 atc ttt ggg agc ctg gca ttt ctg ccg gag agc ttt gat ggg gac cca        1329
Ile Phe Gly Ser Leu Ala Phe Leu Pro Glu Ser Phe Asp Gly Asp Pro
370                 375                 380                 385 gcc tcc aac act gcc ccg ctc cag cca gag cag ctc caa gtg ttt gag        1377
Ala Ser Asn Thr Ala Pro Leu Gln Pro Glu Gln Leu Gln Val Phe Glu
                390                 395                 400 act ctg gaa gag atc aca ggt tac cta tac atc tca gca tgg ccg gac        1425
Thr Leu Glu Glu Ile Thr Gly Tyr Leu Tyr Ile Ser Ala Trp Pro Asp
            405                 410                 415
```

| | | | | | | | | | | | | | | | | |
|---|---|---|---|---|---|---|---|---|---|---|---|---|---|---|---|---|
| agc | ctg | cct | gac | ctc | agc | gtc | ttc | cag | aac | ctg | caa | gta | atc | cgg | gga | 1473 |
| Ser | Leu | Pro | Asp | Leu | Ser | Val | Phe | Gln | Asn | Leu | Gln | Val | Ile | Arg | Gly | |
| | | 420 | | | | 425 | | | | | 430 | | | | | |

| | | | | | | | | | | | | | | | | |
|---|---|---|---|---|---|---|---|---|---|---|---|---|---|---|---|---|
| cga | att | ctg | cac | aat | ggc | gcc | tac | tcg | ctg | acc | ctg | caa | ggg | ctg | ggc | 1521 |
| Arg | Ile | Leu | His | Asn | Gly | Ala | Tyr | Ser | Leu | Thr | Leu | Gln | Gly | Leu | Gly | |
| | | 435 | | | | 440 | | | | | 445 | | | | | |

| | | | | | | | | | | | | | | | | |
|---|---|---|---|---|---|---|---|---|---|---|---|---|---|---|---|---|
| atc | agc | tgg | ctg | ggg | ctg | cgc | tca | ctg | agg | gaa | ctg | ggc | agt | gga | ctg | 1569 |
| Ile | Ser | Trp | Leu | Gly | Leu | Arg | Ser | Leu | Arg | Glu | Leu | Gly | Ser | Gly | Leu | |
| 450 | | | | | 455 | | | | | 460 | | | | | 465 | |

| | | | | | | | | | | | | | | | | |
|---|---|---|---|---|---|---|---|---|---|---|---|---|---|---|---|---|
| gcc | ctc | atc | cac | cat | aac | acc | cac | ctc | tgc | ttc | gtg | cac | acg | gtg | ccc | 1617 |
| Ala | Leu | Ile | His | His | Asn | Thr | His | Leu | Cys | Phe | Val | His | Thr | Val | Pro | |
| | | | 470 | | | | | 475 | | | | | 480 | | | |

| | | | | | | | | | | | | | | | | |
|---|---|---|---|---|---|---|---|---|---|---|---|---|---|---|---|---|
| tgg | gac | cag | ctc | ttt | cgg | aac | ccg | cac | caa | gct | ctg | ctc | cac | act | gcc | 1665 |
| Trp | Asp | Gln | Leu | Phe | Arg | Asn | Pro | His | Gln | Ala | Leu | Leu | His | Thr | Ala | |
| | | | 485 | | | | | 490 | | | | | 495 | | | |

| | | | | | | | | | | | | | | | | |
|---|---|---|---|---|---|---|---|---|---|---|---|---|---|---|---|---|
| aac | cgg | cca | gag | gac | gag | tgt | gtg | ggc | gag | ggc | ctg | gcc | tgc | cac | cag | 1713 |
| Asn | Arg | Pro | Glu | Asp | Glu | Cys | Val | Gly | Glu | Gly | Leu | Ala | Cys | His | Gln | |
| | | 500 | | | | 505 | | | | | 510 | | | | | |

| | | | | | | | | | | | | | | | | |
|---|---|---|---|---|---|---|---|---|---|---|---|---|---|---|---|---|
| ctg | tgc | gcc | cga | ggg | cac | tgc | tgg | ggt | cca | ggg | ccc | acc | cag | tgt | gtc | 1761 |
| Leu | Cys | Ala | Arg | Gly | His | Cys | Trp | Gly | Pro | Gly | Pro | Thr | Gln | Cys | Val | |
| | 515 | | | | | 520 | | | | | 525 | | | | | |

| | | | | | | | | | | | | | | | | |
|---|---|---|---|---|---|---|---|---|---|---|---|---|---|---|---|---|
| aac | tgc | agc | cag | ttc | ctt | cgg | ggc | cag | gag | tgc | gtg | gag | gaa | tgc | cga | 1809 |
| Asn | Cys | Ser | Gln | Phe | Leu | Arg | Gly | Gln | Glu | Cys | Val | Glu | Glu | Cys | Arg | |
| 530 | | | | | 535 | | | | | 540 | | | | | 545 | |

| | | | | | | | | | | | | | | | | |
|---|---|---|---|---|---|---|---|---|---|---|---|---|---|---|---|---|
| gta | ctg | cag | ggg | ctc | ccc | agg | gag | tat | gtg | aat | gcc | agg | cac | tgt | ttg | 1857 |
| Val | Leu | Gln | Gly | Leu | Pro | Arg | Glu | Tyr | Val | Asn | Ala | Arg | His | Cys | Leu | |
| | | | | 550 | | | | | 555 | | | | | 560 | | |

| | | | | | | | | | | | | | | | | |
|---|---|---|---|---|---|---|---|---|---|---|---|---|---|---|---|---|
| ccg | tgc | cac | cct | gag | tgt | cag | ccc | cag | aat | ggc | tca | gtg | acc | tgt | ttt | 1905 |
| Pro | Cys | His | Pro | Glu | Cys | Gln | Pro | Gln | Asn | Gly | Ser | Val | Thr | Cys | Phe | |
| | | | 565 | | | | | 570 | | | | | 575 | | | |

| | | | | | | | | | | | | | | | | |
|---|---|---|---|---|---|---|---|---|---|---|---|---|---|---|---|---|
| gga | ccg | gag | gct | gac | cag | tgt | gtg | gcc | tgt | gcc | cac | tat | aag | gac | cct | 1953 |
| Gly | Pro | Glu | Ala | Asp | Gln | Cys | Val | Ala | Cys | Ala | His | Tyr | Lys | Asp | Pro | |
| | | | | 580 | | | | | 585 | | | | | 590 | | |

| | | | | | | | | | | | | | | | | |
|---|---|---|---|---|---|---|---|---|---|---|---|---|---|---|---|---|
| ccc | ttc | tgc | gtg | gcc | cgc | tgc | ccc | agc | ggt | gtg | aaa | cct | gac | ctc | tcc | 2001 |
| Pro | Phe | Cys | Val | Ala | Arg | Cys | Pro | Ser | Gly | Val | Lys | Pro | Asp | Leu | Ser | |
| | 595 | | | | | 600 | | | | | 605 | | | | | |

| | | | | | | | | | | | | | | | | |
|---|---|---|---|---|---|---|---|---|---|---|---|---|---|---|---|---|
| tac | atg | ccc | atc | tgg | aag | ttt | cca | gat | gag | gag | ggc | gca | tgc | cag | cct | 2049 |
| Tyr | Met | Pro | Ile | Trp | Lys | Phe | Pro | Asp | Glu | Glu | Gly | Ala | Cys | Gln | Pro | |
| 610 | | | | | 615 | | | | | 620 | | | | | 625 | |

| | | | | | | | | | | | | | | | | |
|---|---|---|---|---|---|---|---|---|---|---|---|---|---|---|---|---|
| tgc | ccc | atc | aac | tgc | acc | cac | tcc | tgt | gtg | gac | ctg | gat | gac | aag | ggc | 2097 |
| Cys | Pro | Ile | Asn | Cys | Thr | His | Ser | Cys | Val | Asp | Leu | Asp | Asp | Lys | Gly | |
| | | | 630 | | | | | 635 | | | | | 640 | | | |

| | | | | | | | | | | | | | | | | |
|---|---|---|---|---|---|---|---|---|---|---|---|---|---|---|---|---|
| tgc | ccc | gcc | gag | cag | aga | gcc | agc | cct | ctg | acg | tcc | atc | atc | tct | gcg | 2145 |
| Cys | Pro | Ala | Glu | Gln | Arg | Ala | Ser | Pro | Leu | Thr | Ser | Ile | Ile | Ser | Ala | |
| | | | | 645 | | | | | 650 | | | | | 655 | | |

| | | | | | | | | | | | | | | | | |
|---|---|---|---|---|---|---|---|---|---|---|---|---|---|---|---|---|
| gtg | gtt | ggc | att | ctg | ctg | gtc | gtg | gtc | ttg | ggg | gtg | gtc | ttt | ggg | atc | 2193 |
| Val | Val | Gly | Ile | Leu | Leu | Val | Val | Val | Leu | Gly | Val | Val | Phe | Gly | Ile | |
| | | | 660 | | | | | 665 | | | | | 670 | | | |

| | | | | | | | | | | | | | | | | |
|---|---|---|---|---|---|---|---|---|---|---|---|---|---|---|---|---|
| ctc | atc | aag | cga | cgg | cag | cag | aag | atc | cgg | aag | tac | acg | atg | cgg | aga | 2241 |
| Leu | Ile | Lys | Arg | Arg | Gln | Gln | Lys | Ile | Arg | Lys | Tyr | Thr | Met | Arg | Arg | |
| | | 675 | | | | | 680 | | | | | 685 | | | | |

| | | | | | | | | | | | | | | | | |
|---|---|---|---|---|---|---|---|---|---|---|---|---|---|---|---|---|
| ctg | ctg | cag | gaa | acg | gag | ctg | gtg | gag | ccg | ctg | aca | cct | agc | gga | gcg | 2289 |
| Leu | Leu | Gln | Glu | Thr | Glu | Leu | Val | Glu | Pro | Leu | Thr | Pro | Ser | Gly | Ala | |
| 690 | | | | | 695 | | | | | 700 | | | | | 705 | |

| | | | | | | | | | | | | | | | | |
|---|---|---|---|---|---|---|---|---|---|---|---|---|---|---|---|---|
| atg | ccc | aac | cag | gcg | cag | atg | cgg | atc | ctg | aaa | gag | acg | gag | ctg | agg | 2337 |
| Met | Pro | Asn | Gln | Ala | Gln | Met | Arg | Ile | Leu | Lys | Glu | Thr | Glu | Leu | Arg | |
| | | | | 710 | | | | | 715 | | | | | 720 | | |

| | | | | | | | | | | | | | | | | |
|---|---|---|---|---|---|---|---|---|---|---|---|---|---|---|---|---|
| aag | gtg | aag | gtg | ctt | gga | tct | ggc | gct | ttt | ggc | aca | gtc | tac | aag | ggc | 2385 |
| Lys | Val | Lys | Val | Leu | Gly | Ser | Gly | Ala | Phe | Gly | Thr | Val | Tyr | Lys | Gly | |
| | | | | 725 | | | | | 730 | | | | | 735 | | |

```
atc tgg atc cct gat ggg gag aat gtg aaa att cca gtg gcc atc aaa    2433
Ile Trp Ile Pro Asp Gly Glu Asn Val Lys Ile Pro Val Ala Ile Lys
        740                 745                 750 gtg ttg agg gaa aac aca tcc ccc aaa gcc aac aaa gaa atc tta gac    2481
Val Leu Arg Glu Asn Thr Ser Pro Lys Ala Asn Lys Glu Ile Leu Asp
755                 760                 765 gaa gca tac gtg atg gct ggt gtg ggc tcc cca tat gtc tcc cgc ctt    2529
Glu Ala Tyr Val Met Ala Gly Val Gly Ser Pro Tyr Val Ser Arg Leu
770                 775                 780                 785 ctg ggc atc tgc ctg aca tcc acg gtg cag ctg gtg aca cag ctt atg    2577
Leu Gly Ile Cys Leu Thr Ser Thr Val Gln Leu Val Thr Gln Leu Met
                790                 795                 800 ccc tat ggc tgc ctc tta gac cat gtc cgg gaa aac cgc gga cgc ctg    2625
Pro Tyr Gly Cys Leu Leu Asp His Val Arg Glu Asn Arg Gly Arg Leu
            805                 810                 815 ggc tcc cag gac ctg ctg aac tgg tgt atg cag att gcc aag ggg atg    2673
Gly Ser Gln Asp Leu Leu Asn Trp Cys Met Gln Ile Ala Lys Gly Met
        820                 825                 830 agc tac ctg gag gat gtg cgg ctc gta cac agg gac ttg gcc gct cgg    2721
Ser Tyr Leu Glu Asp Val Arg Leu Val His Arg Asp Leu Ala Ala Arg
835                 840                 845 aac gtg ctg gtc aag agt ccc aac cat gtc aaa att aca gac ttc ggg    2769
Asn Val Leu Val Lys Ser Pro Asn His Val Lys Ile Thr Asp Phe Gly
850                 855                 860                 865 ctg gct cgg ctg ctg gac att gac gag aca gag tac cat gca gat ggg    2817
Leu Ala Arg Leu Leu Asp Ile Asp Glu Thr Glu Tyr His Ala Asp Gly
                870                 875                 880 ggc aag gtg ccc atc aag tgg atg gcg ctg gag tcc att ctc cgc cgg    2865
Gly Lys Val Pro Ile Lys Trp Met Ala Leu Glu Ser Ile Leu Arg Arg
            885                 890                 895 cgg ttc acc cac cag agt gat gtg tgg agt tat ggt gtg act gtg tgg    2913
Arg Phe Thr His Gln Ser Asp Val Trp Ser Tyr Gly Val Thr Val Trp
        900                 905                 910 gag ctg atg act ttt ggg gcc aaa cct tac gat ggg atc cca gcc cgg    2961
Glu Leu Met Thr Phe Gly Ala Lys Pro Tyr Asp Gly Ile Pro Ala Arg
915                 920                 925 gag atc cct gac ctg ctg gaa aag ggg gag cgg ctg ccc cag ccc ccc    3009
Glu Ile Pro Asp Leu Leu Glu Lys Gly Glu Arg Leu Pro Gln Pro Pro
930                 935                 940                 945 atc tgc acc att gat gtc tac atg atc atg gtc aaa tgt tgg atg att    3057
Ile Cys Thr Ile Asp Val Tyr Met Ile Met Val Lys Cys Trp Met Ile
                950                 955                 960 gac tct gaa tgt cgg cca aga ttc cgg gag ttg gtg tct gaa ttc tcc    3105
Asp Ser Glu Cys Arg Pro Arg Phe Arg Glu Leu Val Ser Glu Phe Ser
            965                 970                 975 cgc atg gcc agg gac ccc cag cgc ttt gtg gtc atc cag aat gag gac    3153
Arg Met Ala Arg Asp Pro Gln Arg Phe Val Val Ile Gln Asn Glu Asp
        980                 985                 990 ttg ggc cca gcc agt ccc ttg gac agc acc ttc tac cgc tca ctg ctg    3201
Leu Gly Pro Ala Ser Pro Leu Asp Ser Thr Phe Tyr Arg Ser Leu Leu
        995                 1000                1005 gag gac gat gac atg ggg gac ctg gtg gat gct gag gag tat ctg       3246
Glu Asp Asp Asp Met Gly Asp Leu Val Asp Ala Glu Glu Tyr Leu
1010                1015                1020 gta ccc cag cag ggc ttc ttc tgt cca gac cct gcc ccg ggc gct       3291
Val Pro Gln Gln Gly Phe Phe Cys Pro Asp Pro Ala Pro Gly Ala
1025                1030                1035 ggg ggc atg gtc cac cac agg cac cgc agc tca tct acc agg agt       3336
Gly Gly Met Val His His Arg His Arg Ser Ser Ser Thr Arg Ser
```

| | | | | | | | | | | |
|---|---|---|---|---|---|---|---|---|---|---|
| | | | 1040 | | | 1045 | | | 1050 | |
| ggc | ggt | ggg | gac | ctg | aca | cta | ggg | ctg | gag | ccc | tct | gaa | gag | gag | 3381 |
| Gly | Gly | Gly | Asp | Leu | Thr | Leu | Gly | Leu | Glu | Pro | Ser | Glu | Glu | Glu | |
| 1055 | | | | 1060 | | | | | 1065 | | | | | | |

| gcc | ccc | agg | tct | cca | ctg | gca | ccc | tcc | gaa | ggg | gct | ggc | tcc | gat | 3426 |
|---|---|---|---|---|---|---|---|---|---|---|---|---|---|---|---|
| Ala | Pro | Arg | Ser | Pro | Leu | Ala | Pro | Ser | Glu | Gly | Ala | Gly | Ser | Asp | |
| 1070 | | | | 1075 | | | | | 1080 | | | | | | |

| gta | ttt | gat | ggt | gac | ctg | gga | atg | ggg | gca | gcc | aag | ggg | ctg | caa | 3471 |
|---|---|---|---|---|---|---|---|---|---|---|---|---|---|---|---|
| Val | Phe | Asp | Gly | Asp | Leu | Gly | Met | Gly | Ala | Ala | Lys | Gly | Leu | Gln | |
| 1085 | | | | 1090 | | | | | 1095 | | | | | | |

| agc | ctc | ccc | aca | cat | gac | ccc | agc | cct | cta | cag | cgg | tac | agt | gag | 3516 |
|---|---|---|---|---|---|---|---|---|---|---|---|---|---|---|---|
| Ser | Leu | Pro | Thr | His | Asp | Pro | Ser | Pro | Leu | Gln | Arg | Tyr | Ser | Glu | |
| 1100 | | | | 1105 | | | | | 1110 | | | | | | |

| gac | ccc | aca | gta | ccc | ctg | ccc | tct | gag | act | gat | ggc | tac | gtt | gcc | 3561 |
|---|---|---|---|---|---|---|---|---|---|---|---|---|---|---|---|
| Asp | Pro | Thr | Val | Pro | Leu | Pro | Ser | Glu | Thr | Asp | Gly | Tyr | Val | Ala | |
| 1115 | | | | 1120 | | | | | 1125 | | | | | | |

| ccc | ctg | acc | tgc | agc | ccc | cag | cct | gaa | tat | gtg | aac | cag | cca | gat | 3606 |
|---|---|---|---|---|---|---|---|---|---|---|---|---|---|---|---|
| Pro | Leu | Thr | Cys | Ser | Pro | Gln | Pro | Glu | Tyr | Val | Asn | Gln | Pro | Asp | |
| 1130 | | | | 1135 | | | | | 1140 | | | | | | |

| gtt | cgg | ccc | cag | ccc | cct | tcg | ccc | cga | gag | ggc | cct | ctg | cct | gct | 3651 |
|---|---|---|---|---|---|---|---|---|---|---|---|---|---|---|---|
| Val | Arg | Pro | Gln | Pro | Pro | Ser | Pro | Arg | Glu | Gly | Pro | Leu | Pro | Ala | |
| 1145 | | | | 1150 | | | | | 1155 | | | | | | |

| gcc | cga | cct | gct | ggt | gcc | act | ctg | gaa | agg | ccc | aag | act | ctc | tcc | 3696 |
|---|---|---|---|---|---|---|---|---|---|---|---|---|---|---|---|
| Ala | Arg | Pro | Ala | Gly | Ala | Thr | Leu | Glu | Arg | Pro | Lys | Thr | Leu | Ser | |
| 1160 | | | | 1165 | | | | | 1170 | | | | | | |

| cca | ggg | aag | aat | ggg | gtc | gtc | aaa | gac | gtt | ttt | gcc | ttt | ggg | ggt | 3741 |
|---|---|---|---|---|---|---|---|---|---|---|---|---|---|---|---|
| Pro | Gly | Lys | Asn | Gly | Val | Val | Lys | Asp | Val | Phe | Ala | Phe | Gly | Gly | |
| 1175 | | | | 1180 | | | | | 1185 | | | | | | |

| gcc | gtg | gag | aac | ccc | gag | tac | ttg | aca | ccc | cag | gga | gga | gct | gcc | 3786 |
|---|---|---|---|---|---|---|---|---|---|---|---|---|---|---|---|
| Ala | Val | Glu | Asn | Pro | Glu | Tyr | Leu | Thr | Pro | Gln | Gly | Gly | Ala | Ala | |
| 1190 | | | | 1195 | | | | | 1200 | | | | | | |

| cct | cag | ccc | cac | cct | cct | cct | gcc | ttc | agc | cca | gcc | ttc | gac | aac | 3831 |
|---|---|---|---|---|---|---|---|---|---|---|---|---|---|---|---|
| Pro | Gln | Pro | His | Pro | Pro | Pro | Ala | Phe | Ser | Pro | Ala | Phe | Asp | Asn | |
| 1205 | | | | 1210 | | | | | 1215 | | | | | | |

| ctc | tat | tac | tgg | gac | cag | gac | cca | cca | gag | cgg | ggg | gct | cca | ccc | 3876 |
|---|---|---|---|---|---|---|---|---|---|---|---|---|---|---|---|
| Leu | Tyr | Tyr | Trp | Asp | Gln | Asp | Pro | Pro | Glu | Arg | Gly | Ala | Pro | Pro | |
| 1220 | | | | 1225 | | | | | 1230 | | | | | | |

| agc | acc | ttc | aaa | ggg | aca | cct | acg | gca | gag | aac | cca | gag | tac | ctg | 3921 |
|---|---|---|---|---|---|---|---|---|---|---|---|---|---|---|---|
| Ser | Thr | Phe | Lys | Gly | Thr | Pro | Thr | Ala | Glu | Asn | Pro | Glu | Tyr | Leu | |
| 1235 | | | | 1240 | | | | | 1245 | | | | | | |

| ggt | ctg | gac | gtg | cca | gtg | tga accagaaggc caagtccgca gaagccctga | 3972 |
|---|---|---|---|---|---|---|---|
| Gly | Leu | Asp | Val | Pro | Val | | |
| 1250 | | | | 1255 | | | |

| tgtgtcctca gggagcaggg aaggcctgac ttctgctggc atcaagaggt gggagggccc | 4032 |
|---|---|
| tccgaccact tccaggggaa cctgccatgc caggaacctg tcctaaggaa ccttccttcc | 4092 |
| tgcttgagtt cccagatggc tggaaggggt ccagcctcgt tggaagagga acagcactgg | 4152 |
| ggagtctttg tggattctga ggccctgccc aatgagactc tagggtccag tggatgccac | 4212 |
| agcccagctt ggccctttcc ttccagatcc tgggtactga aagccttagg gaagctggcc | 4272 |
| tgagagggga agcggcccta agggagtgtc taagaacaaa agcgacccat tcagagactg | 4332 |
| tccctgaaac ctagtactgc cccccatgag gaaggaacag caatggtgtc agtatccagg | 4392 |
| cttttgtacag agtgcttttc tgtttagttt ttacttttttt tgtttttgttt tttttaaagat | 4452 |
| gaaataaaga cccaggggga g | 4473 |

<210> SEQ ID NO 24
<211> LENGTH: 1255

<212> TYPE: PRT
<213> ORGANISM: Homo sapiens

<400> SEQUENCE: 24

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400
```

```
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
```

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro

```
                1220                 1225                 1230
Pro Ser Thr Phe Lys Gly Thr Pro Thr Ala Glu Asn Pro Glu Tyr
    1235                 1240                 1245

Leu Gly Leu Asp Val Pro Val
    1250                 1255

<210> SEQ ID NO 25
<211> LENGTH: 1212
<212> TYPE: DNA
<213> ORGANISM: Homo sapiens
<220> FEATURE:
<221> NAME/KEY: CDS
<222> LOCATION: (1)..(1212)

<400> SEQUENCE: 25 atg aca gcc atc atc aaa gag atc gtt agc aga aac aaa agg aga tat    48
Met Thr Ala Ile Ile Lys Glu Ile Val Ser Arg Asn Lys Arg Arg Tyr
1               5                   10                  15 caa gag gat gga ttc gac tta gac ttg acc tat att tat cca aac att    96
Gln Glu Asp Gly Phe Asp Leu Asp Leu Thr Tyr Ile Tyr Pro Asn Ile
                20                  25                  30 att gct atg gga ttt cct gca gaa aga ctt gaa ggc gta tac agg aac   144
Ile Ala Met Gly Phe Pro Ala Glu Arg Leu Glu Gly Val Tyr Arg Asn
            35                  40                  45 aat att gat gat gta gta agg ttt ttg gat tca aag cat aaa aac cat   192
Asn Ile Asp Asp Val Val Arg Phe Leu Asp Ser Lys His Lys Asn His
        50                  55                  60 tac aag ata tac aat ctt tgt gct gaa aga cat tat gac acc gcc aaa   240
Tyr Lys Ile Tyr Asn Leu Cys Ala Glu Arg His Tyr Asp Thr Ala Lys
65                  70                  75                  80 ttt aat tgc aga gtt gca caa tat cct ttt gaa gac cat aac cca cca   288
Phe Asn Cys Arg Val Ala Gln Tyr Pro Phe Glu Asp His Asn Pro Pro
                85                  90                  95 cag cta gaa ctt atc aaa ccc ttt tgt gaa gat ctt gac caa tgg cta   336
Gln Leu Glu Leu Ile Lys Pro Phe Cys Glu Asp Leu Asp Gln Trp Leu
            100                 105                 110 agt gaa gat gac aat cat gtt gca gca att cac tgt aaa gct gga aag   384
Ser Glu Asp Asp Asn His Val Ala Ala Ile His Cys Lys Ala Gly Lys
        115                 120                 125 gga cga act ggt gta atg ata tgt gca tat tta tta cat cgg ggc aaa   432
Gly Arg Thr Gly Val Met Ile Cys Ala Tyr Leu Leu His Arg Gly Lys
    130                 135                 140 ttt tta aag gca caa gag gcc cta gat ttc tat ggg gaa gta agg acc   480
Phe Leu Lys Ala Gln Glu Ala Leu Asp Phe Tyr Gly Glu Val Arg Thr
145                 150                 155                 160 aga gac aaa aag gga gta act att ccc agt cag agg cgc tat gtg tat   528
Arg Asp Lys Lys Gly Val Thr Ile Pro Ser Gln Arg Arg Tyr Val Tyr
                165                 170                 175 tat tat agc tac ctg tta aag aat cat ctg gat tat aga cca gtg gca   576
Tyr Tyr Ser Tyr Leu Leu Lys Asn His Leu Asp Tyr Arg Pro Val Ala
            180                 185                 190 ctg ttg ttt cac aag atg atg ttt gaa act att cca atg ttc agt ggc   624
Leu Leu Phe His Lys Met Met Phe Glu Thr Ile Pro Met Phe Ser Gly
        195                 200                 205 gga act tgc aat cct cag ttt gtg gtc tgc cag cta aag gtg aag ata   672
Gly Thr Cys Asn Pro Gln Phe Val Val Cys Gln Leu Lys Val Lys Ile
    210                 215                 220 tat tcc tcc aat tca gga ccc aca cga cgg gaa gac aag ttc atg tac   720
Tyr Ser Ser Asn Ser Gly Pro Thr Arg Arg Glu Asp Lys Phe Met Tyr
225                 230                 235                 240
```

-continued

| | | |
|---|---|---|
| ttt gag ttc cct cag ccg tta cct gtg tgt ggt gat atc aaa gta gag<br>Phe Glu Phe Pro Gln Pro Leu Pro Val Cys Gly Asp Ile Lys Val Glu<br>                              245                              250                            255 | 768 |
| ttc ttc cac aaa cag aac aag atg cta aaa aag gac aaa atg ttt cac<br>Phe Phe His Lys Gln Asn Lys Met Leu Lys Lys Asp Lys Met Phe His<br>                              260                              265                            270 | 816 |
| ttt tgg gta aat aca ttc ttc ata cca gga cca gag gaa acc tca gaa<br>Phe Trp Val Asn Thr Phe Phe Ile Pro Gly Pro Glu Glu Thr Ser Glu<br>        275                              280                              285 | 864 |
| aaa gta gaa aat gga agt cta tgt gat caa gaa atc gat agc att tgc<br>Lys Val Glu Asn Gly Ser Leu Cys Asp Gln Glu Ile Asp Ser Ile Cys<br>                290                              295                            300 | 912 |
| agt ata gag cgt gca gat aat gac aag gaa tat cta gta ctt act tta<br>Ser Ile Glu Arg Ala Asp Asn Asp Lys Glu Tyr Leu Val Leu Thr Leu<br>305                            310                              315                            320 | 960 |
| aca aaa aat gat ctt gac aaa gca aat aaa gac aaa gcc aac cga tac<br>Thr Lys Asn Asp Leu Asp Lys Ala Asn Lys Asp Lys Ala Asn Arg Tyr<br>                        325                              330                            335 | 1008 |
| ttt tct cca aat ttt aag gtg aag ctg tac ttc aca aaa aca gta gag<br>Phe Ser Pro Asn Phe Lys Val Lys Leu Tyr Phe Thr Lys Thr Val Glu<br>        340                              345                              350 | 1056 |
| gag ccg tca aat cca gag gct agc agt tca act tct gta aca cca gat<br>Glu Pro Ser Asn Pro Glu Ala Ser Ser Ser Thr Ser Val Thr Pro Asp<br>                355                              360                            365 | 1104 |
| gtt agt gac aat gaa cct gat cat tat aga tat tct gac acc act gac<br>Val Ser Asp Asn Glu Pro Asp His Tyr Arg Tyr Ser Asp Thr Thr Asp<br>370                            375                              380 | 1152 |
| tct gat cca gag aat gaa cct ttt gat gaa gat cag cat aca caa att<br>Ser Asp Pro Glu Asn Glu Pro Phe Asp Glu Asp Gln His Thr Gln Ile<br>385                            390                            395                            400 | 1200 |
| aca aaa gtc tga<br>Thr Lys Val | 1212 |

<210> SEQ ID NO 26
<211> LENGTH: 403
<212> TYPE: PRT
<213> ORGANISM: Homo sapiens

<400> SEQUENCE: 26

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ile His Cys Lys Ala Gly Lys
            115                 120                 125

Gly Arg Thr Gly Val Met Ile Cys Ala Tyr Leu Leu His Arg Gly Lys
        130                 135                 140

Phe Leu Lys Ala Gln Glu Ala Leu Asp Phe Tyr Gly Glu Val Arg Thr

```
                145                 150                 155                 160
Arg Asp Lys Lys Gly Val Thr Ile Pro Ser Gln Arg Arg Tyr Val Tyr
                    165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val

<210> SEQ ID NO 27
<211> LENGTH: 597
<212> TYPE: DNA
<213> ORGANISM: Homo sapiens
<220> FEATURE:
<221> NAME/KEY: CDS
<222> LOCATION: (1)..(597)

<400> SEQUENCE: 27 atg tca aac gtg cga gtg tct aac ggg agc cct agc ctg gag cgg atg      48
Met Ser Asn Val Arg Val Ser Asn Gly Ser Pro Ser Leu Glu Arg Met
1               5                   10                  15 gac gcc agg cag gcg gag cac ccc aag ccc tcg gcc tgc agg aac ctc      96
Asp Ala Arg Gln Ala Glu His Pro Lys Pro Ser Ala Cys Arg Asn Leu
            20                  25                  30 ttc ggc ccg gtg gac cac gaa gag tta acc cgg gac ttg gag aag cac     144
Phe Gly Pro Val Asp His Glu Glu Leu Thr Arg Asp Leu Glu Lys His
        35                  40                  45 tgc aga gac atg gaa gag gcg agc cag cgc aag tgg aat ttc gat ttt     192
Cys Arg Asp Met Glu Glu Ala Ser Gln Arg Lys Trp Asn Phe Asp Phe
    50                  55                  60 cag aat cac aaa ccc cta gag ggc aag tac gag tgg caa gag gtg gag     240
Gln Asn His Lys Pro Leu Glu Gly Lys Tyr Glu Trp Gln Glu Val Glu
65                  70                  75                  80
```

```
aag ggc agc ttg ccc gag ttc tac tac aga ccc ccg cgg ccc ccc aaa    288
Lys Gly Ser Leu Pro Glu Phe Tyr Tyr Arg Pro Pro Arg Pro Pro Lys
             85                  90                  95 ggt gcc tgc aag gtg ccg gcg cag gag agc cag gat gtc agc ggg agc    336
Gly Ala Cys Lys Val Pro Ala Gln Glu Ser Gln Asp Val Ser Gly Ser
            100                 105                 110 cgc ccg gcg gcg cct tta att ggg gct ccg gct aac tct gag gac acg    384
Arg Pro Ala Ala Pro Leu Ile Gly Ala Pro Ala Asn Ser Glu Asp Thr
        115                 120                 125 cat ttg gtg gac cca aag act gat ccg tcg gac agc cag acg ggg tta    432
His Leu Val Asp Pro Lys Thr Asp Pro Ser Asp Ser Gln Thr Gly Leu
    130                 135                 140 gcg gag caa tgc gca gga ata agg aag cga cct gca acc gac gat tct    480
Ala Glu Gln Cys Ala Gly Ile Arg Lys Arg Pro Ala Thr Asp Asp Ser
145                 150                 155                 160 tct act caa aac aaa aga gcc aac aga aca gaa gaa aat gtt tca gac    528
Ser Thr Gln Asn Lys Arg Ala Asn Arg Thr Glu Glu Asn Val Ser Asp
                165                 170                 175 ggt tcc cca aat gcc ggt tct gtg gag cag acg ccc aag aag cct ggc    576
Gly Ser Pro Asn Ala Gly Ser Val Glu Gln Thr Pro Lys Lys Pro Gly
            180                 185                 190 ctc aga aga cgt caa acg taa                                        597
Leu Arg Arg Arg Gln Thr
            195
```

<210> SEQ ID NO 28
<211> LENGTH: 198
<212> TYPE: PRT
<213> ORGANISM: Homo sapiens

<400> SEQUENCE: 28

```
Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
            195
```

```
<210> SEQ ID NO 29
<211> LENGTH: 894
<212> TYPE: DNA
<213> ORGANISM: Homo sapiens
<220> FEATURE:
<221> NAME/KEY: CDS
<222> LOCATION: (1)..(894)

<400> SEQUENCE: 29 atg aca aca ccc aga aat tca gta aat ggg act ttc ccg gca gag cca        48
Met Thr Thr Pro Arg Asn Ser Val Asn Gly Thr Phe Pro Ala Glu Pro
1               5                   10                  15 atg aaa ggc cct att gct atg caa tct ggt cca aaa cca ctc ttc agg        96
Met Lys Gly Pro Ile Ala Met Gln Ser Gly Pro Lys Pro Leu Phe Arg
            20                  25                  30 agg atg tct tca ctg gtg ggc ccc acg caa agc ttc ttc atg agg gaa       144
Arg Met Ser Ser Leu Val Gly Pro Thr Gln Ser Phe Phe Met Arg Glu
        35                  40                  45 tct aag act ttg ggg gct gtc cag att atg aat ggg ctc ttc cac att       192
Ser Lys Thr Leu Gly Ala Val Gln Ile Met Asn Gly Leu Phe His Ile
    50                  55                  60 gcc ctg ggg ggt ctt ctg atg atc cca gca ggg atc tat gca ccc atc       240
Ala Leu Gly Gly Leu Leu Met Ile Pro Ala Gly Ile Tyr Ala Pro Ile
65                  70                  75                  80 tgt gtg act gtg tgg tac cct ctc tgg gga ggc att atg tat att att       288
Cys Val Thr Val Trp Tyr Pro Leu Trp Gly Gly Ile Met Tyr Ile Ile
                85                  90                  95 tcc gga tca ctc ttg gca gca acg gag aaa aac tct agg aag tgt ttg       336
Ser Gly Ser Leu Leu Ala Ala Thr Glu Lys Asn Ser Arg Lys Cys Leu
            100                 105                 110 gtc aaa gga aaa atg ata atg aat tca ttg agc ctc ttt gct gcc att       384
Val Lys Gly Lys Met Ile Met Asn Ser Leu Ser Leu Phe Ala Ala Ile
        115                 120                 125 tct gga atg att ctt tca atc atg gac ata ctt aat att aaa att tcc       432
Ser Gly Met Ile Leu Ser Ile Met Asp Ile Leu Asn Ile Lys Ile Ser
    130                 135                 140 cat ttt tta aaa atg gag agt ctg aat ttt att aga gct cac aca cca       480
His Phe Leu Lys Met Glu Ser Leu Asn Phe Ile Arg Ala His Thr Pro
145                 150                 155                 160 tat att aac ata tac aac tgt gaa cca gct aat ccc tct gag aaa aac       528
Tyr Ile Asn Ile Tyr Asn Cys Glu Pro Ala Asn Pro Ser Glu Lys Asn
                165                 170                 175 tcc cca tct acc caa tac tgt tac agc ata caa tct ctg ttc ttg ggc       576
Ser Pro Ser Thr Gln Tyr Cys Tyr Ser Ile Gln Ser Leu Phe Leu Gly
            180                 185                 190 att ttg tca gtg atg ctg atc ttt gcc ttc ttc cag gaa ctt gta ata       624
Ile Leu Ser Val Met Leu Ile Phe Ala Phe Phe Gln Glu Leu Val Ile
        195                 200                 205 gct ggc atc gtt gag aat gaa tgg aaa aga acg tgc tcc aga ccc aaa       672
Ala Gly Ile Val Glu Asn Glu Trp Lys Arg Thr Cys Ser Arg Pro Lys
    210                 215                 220 tct aac ata gtt ctc ctg tca gca gaa gaa aaa aaa gaa cag act att       720
Ser Asn Ile Val Leu Leu Ser Ala Glu Glu Lys Lys Glu Gln Thr Ile
225                 230                 235                 240 gaa ata aaa gaa gaa gtg gtt ggg cta act gaa aca tct tcc caa cca       768
Glu Ile Lys Glu Glu Val Val Gly Leu Thr Glu Thr Ser Ser Gln Pro
                245                 250                 255 aag aat gaa gaa gac att gaa att att cca atc caa gaa gag gaa gaa       816
Lys Asn Glu Glu Asp Ile Glu Ile Ile Pro Ile Gln Glu Glu Glu Glu
            260                 265                 270
```

```
gaa gaa aca gag acg aac ttt cca gaa cct ccc caa gat cag gaa tcc    864
Glu Glu Thr Glu Thr Asn Phe Pro Glu Pro Pro Gln Asp Gln Glu Ser
        275                 280                 285 tca cca ata gaa aat gac agc tct cct taa                            894
Ser Pro Ile Glu Asn Asp Ser Ser Pro
        290                 295

<210> SEQ ID NO 30
<211> LENGTH: 297
<212> TYPE: PRT
<213> ORGANISM: Homo sapiens

<400> SEQUENCE: 30

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295
```